United States Patent
Gahler et al.

(10) Patent No.: US 9,669,051 B2
(45) Date of Patent: Jun. 6, 2017

(54) DIETARY FIBER COMPOSITIONS WITH METFORMIN, SITAGLIPTIN, OR A COMBINATION THEREOF FOR THE TREATMENT OF METABOLIC DISEASE

(71) Applicant: Inovobiologic Inc., Calgary (CA)

(72) Inventors: Roland Jacques Gahler, Burnaby (CA); Michael Robert Lyon, Nanaimo (CA); Simon Wood, Victoria (CA)

(73) Assignee: InovoBiologic Inc., Calgary (CA)

( * ) Notice: Subject to any disclaimer, the term of this patent is extended or adjusted under 35 U.S.C. 154(b) by 0 days.

(21) Appl. No.: 14/394,337

(22) PCT Filed: Apr. 22, 2013

(86) PCT No.: PCT/CA2013/000392
§ 371 (c)(1),
(2) Date: Oct. 14, 2014

(87) PCT Pub. No.: WO2013/159190
PCT Pub. Date: Oct. 31, 2013

(65) Prior Publication Data
US 2015/0086621 A1    Mar. 26, 2015

Related U.S. Application Data

(60) Provisional application No. 61/638,147, filed on Apr. 25, 2012.

(51) Int. Cl.
*A61K 47/36* (2006.01)
*A61K 31/734* (2006.01)
(Continued)

(52) U.S. Cl.
CPC ............ *A61K 31/734* (2013.01); *A23L 33/40* (2016.08); *A61K 9/1652* (2013.01);
(Continued)

(58) Field of Classification Search
CPC .......... A23V 2200/02; A23V 2200/328; A23V 2200/3262; A23V 2250/5026; A23V 2250/505; A23V 2250/5086; A23L 1/296
See application file for complete search history.

(56) References Cited

U.S. PATENT DOCUMENTS

2006/0228397 A1    10/2006   Gahler

FOREIGN PATENT DOCUMENTS

| CA | 2 633 167 A1 | 7/2007 |
| CA | 2 791 418 A1 | 9/2011 |

(Continued)

OTHER PUBLICATIONS

First Examination Report mailed Jul. 21, 2015, issued in corresponding New Zealand Application No. 630970, filed Apr. 22, 2013, 2 pages.

(Continued)

*Primary Examiner* — Carlos Azpuru
(74) *Attorney, Agent, or Firm* — Christensen O'Connor Johnson Kindness PLLC

(57) ABSTRACT

A pharmaceutical composition composed of a dietary fiber composition composed of from about 48% to about 90% (w/w) glucomannan, from about 5% to about 20% (w/w) xanthan gum, and from about 5% to about 30% (w/w) alginate in combination with at least one of metformin or sitagliptin or a combination thereof is described. The pharmaceutical composition is effective to lower elevated blood glucose levels and total blood cholesterol levels in a subject significantly more than the dietary fiber composition alone or a composition consisting of at least one of metformin or sitagliptin or a combination thereof.

48 Claims, 29 Drawing Sheets

(51) Int. Cl.
A61K 31/155 (2006.01)
A61K 31/4985 (2006.01)
A61K 31/723 (2006.01)
A61K 31/736 (2006.01)
A61K 9/16 (2006.01)
A61K 9/48 (2006.01)
A23L 33/00 (2016.01)

(52) U.S. Cl.
CPC .......... *A61K 9/4866* (2013.01); *A61K 31/155* (2013.01); *A61K 31/4985* (2013.01); *A61K 31/723* (2013.01); *A61K 31/736* (2013.01); *A23V 2200/02* (2013.01); *A23V 2200/328* (2013.01); *A23V 2200/3262* (2013.01); *A23V 2250/505* (2013.01); *A23V 2250/5026* (2013.01); *A23V 2250/5086* (2013.01)

(56) References Cited

FOREIGN PATENT DOCUMENTS

JP 2010-521492 A 6/2010
WO 2008/113000 A1 9/2008

OTHER PUBLICATIONS

"As Seen on Dr. Oz, With John Gray . . . PGX; It Will Change Your Life Even if You Don't!" Mar. 29, 2012, <http://www.naturesfare.com/blog/as-seen-on-dr-oz-with-john-gray%E2%80%A6-pgx-it-will-change-your-life-event-you-don%E2%80%99t/> [retrieved Jul. 19, 2013], 1 page.
Grover, G.J., et al., "Effects of the Soluble Fiber Complex PolyGlycopleX® on Glucose Homeostasis and Body Weight in Young Zucker Diabetic Rats," Frontiers in Pharmacology 2(47):1-10, Sep. 2011.
International Search Report and Written Opinion mailed Jul. 30, 2013, in corresponding International Application No. PCT/CA2013/000392, filed Apr. 22, 2013, 13 pages.
"PGX Supplement and Metformin," Jun. 29, 2010, <http://www.diabetesforums.com/forum/ dieting-and-nutrition-diabetes/53598-pgx-supplement-and-metformin.html> [retrieved Jul. 19, 2013], 1 page.
"Question," May 7, 2008, <http://www.diabetesforums.com/forum/type-2-diabetes/28308-question.html> [retrieved Jul. 19, 2013], 1 page.
"Question," Mar. 8, 2012, <http://www.justanswer.com/medical/6cuht-taking-pgx-diabetes-pre-diabetic.html> [retrieved Jul. 19, 2013], 1 page.
Reimer, R.A., et al., "Sitagliptin Reduces Hyperglycemia and Increases Satiety Hormone Secretion More Effectively When Used With a Novel Polysaccharide in Obese Zucker Rats," Journal of Nutrition 142(10):1812-1820, Oct. 2012.
Office Action mailed Apr. 30, 2015, issued in corresponding Canadian Application No. 2,870,813, filed Apr. 22, 2013, 4 pages.
Office Action mailed Oct. 1, 2015, issued in corresponding Canadian Application No. 2870813, filed Apr. 22, 2013, 5 pages.
Office Action mailed Jan. 6, 2015, issued in corresponding Canadian Application No. 2,870,813, filed Apr. 22, 2013, 5 pages.
Extended European Search Report mailed Dec. 21, 2015, issued in corresponding European Application No. 13780590.9, filed Apr. 22, 2013, 9 pages.
Pyra, K.A., et al., "Prebiotic Fiber Increases Hepatic Acetyl CoA Carboxylase Phosphorylation and Suppresses Glucose-Dependent Insulinotropic Polypeptide Secretion More Effectively When Used with Metformin in Obese Rats," Journal of Nutrition, 142(2): 213-220, Feb. 2012.
Notice of Reasons for Rejection mailed Feb. 3, 2017, issued in JP Application No. 2015-507308, filed Apr. 22, 2013, 11 pages

DIETARY FIBER COMPOSITIONS WITH METFORMIN, SITAGLIPTIN, OR A COMBINATION THEREOF FOR THE TREATMENT OF METABOLIC DISEASE

BACKGROUND

Obesity and metabolic syndrome, conditions that may lead to the development of type II diabetes, have become more and more common. An increase in visceral obesity, serum glucose, and insulin levels, along with hypertension and dyslipidemia are a group of clinical conditions that are collectively known as metabolic syndrome (E. J. Gallagher, et al., *Endocrinol. Metab. Clin. North Am.* 37:559-19 (2008)). It has been found that these conditions are due to increasing insulin resistance of the cells, and in some cases, these symptoms are a precursor to type II diabetes. Type II diabetes is typically managed with various pharmaceuticals to regulate blood sugar, and in more severe cases, insulin injections. However, diet and weight loss play a major role in correcting many metabolic abnormalities associated with both metabolic syndrome and type II diabetes (Yip et al., *Obesity Res.* 9:341S-347S (2001)). Research has shown that those who have metabolic syndrome have a 50% greater risk of experiencing a major coronary event (D. E., Moller et al., *Annu Rev Med* 56:45-62 (2005)). As such, any reductions in weight, fasting insulin and glucose would confer significant health benefits on those individuals so afflicted.

Typically, subjects suffering from type II diabetes are also likely to have dyslipidemia (i.e., diabetic dyslipidemia), where the subjects have abnormally low levels of HDL (i.e., <40 mg/dL) and/or abnormally high levels of low density lipoprotein (LDL) (i.e., >100 mg/dL), cholesterol, and/or abnormally high levels of triglycerides, which increase the risk of atherosclerosis and the risk for developing cardiovascular disease (see *Circulation* 110:227-239 (2004)).

Intake of foods with a high glycemic index is known to lead to overeating and obesity (Ludwig et al., *Pediatrics* 103(3):E26 (1999)). Therefore, it is preferable that any agent used in the management of diabetic or pre-diabetic conditions as well as weight loss be low in glycemic index. It is most preferable if such agents reduce the glycemic index of foods.

A reduction in carbohydrate intake is also required in successful management of diabetic conditions. Diet counseling is helpful, but diabetics experience more food cravings as they experience more frequent states of hypoglycemia (Strachan et al., *Physiol. Behav.* 80(5):675-82 (2004)). Additionally, therapies lowering blood glucose levels in diabetic patients are often associated with the undesirable side effect of body weight gain (Schultes et al., *J. Clin. Endocrinol. Metabol.* 88(3):1133-41 (2003)). It has been reported that diets high in soluble fiber may reduce the risk of diabetes through increased insulin sensitivity (Ylonen et al., *Diabetes Care* 26:1979-85 (2003)). This may result from the possible role of dietary fiber in blood sugar regulation. It has also been reported that high viscosity meals produce a greater sense of fullness compared to low viscosity meals (Marciani et al., *Am. J. Physiol. Gastrointest. Liver Physiol.* 280:G1227-33 (2001)).

Thus, there is a need for compositions that assist in the management of metabolic disease and disorders and associated metabolic syndrome, including diabetic conditions, by lowering blood sugar levels and promoting satiety. The present invention addresses this need and others.

SUMMARY

In one aspect, the invention provides a pharmaceutical composition comprising (i) a dietary fiber composition comprising from about 48% to about 90% (w/w) glucomannan, from about 5% to about 20% (w/w) xanthan gum, and from about 5% to about 30% (w/w) alginate; and (ii) at least one of metformin, sitagliptin, or a combination thereof. In some embodiments, the pharmaceutical composition comprises a combination of a dietary fiber composition and metformin. In some embodiments, the pharmaceutical composition comprises a combination of a dietary fiber composition and sitagliptin. In some embodiments, the pharmaceutical composition comprises a combination of a dietary fiber composition, metformin and sitagliptin.

In another aspect, the invention provides a method for preventing, treating, or ameliorating one or more symptoms associated with a metabolic disease or disorder. The method according to this aspect of the invention comprises co-administering to a human subject in need thereof (i) a dietary fiber composition comprising from about 48% to about 90% (w/w) glucomannan, from about 5% to about 20% (w/w) xanthan gum, and from about 5% to about 30% (w/w) alginate; and (ii) an effective amount of at least one of metformin, sitagliptin, or a combination thereof. In some embodiments, the method comprises administering the dietary fiber composition to the subject in an amount of from about 5 g to about 100 g per day.

In some embodiments, the metabolic disease or disorder is metabolic syndrome or type II diabetes. In some embodiments, the dietary fiber composition is administered to the subject before the administration of metformin and/or sitagliptin. In some embodiments, the dietary fiber composition is administered to the subject simultaneously with the administration of metformin and/or sitagliptin. In some embodiments, the dietary fiber composition and metformin are co-administered in a single pharmaceutical composition. In some embodiments, the dietary fiber and sitagliptin are co-administered in a single pharmaceutical composition. In some embodiments, the dietary fiber, metformin and sitagliptin are co-administered in a single pharmaceutical composition. In some embodiments, at least one of the metformin and/or sitagliptin is administered to the subject before the dietary fiber composition.

In some embodiments, the methods of the invention are effective in lowering elevated blood glucose levels in a subject by administering the dietary fiber composition and metformin, sitagliptin, or a combination thereof.

In some embodiments, the methods of the invention are effective in preserving pancreatic islet function by preserving islet cell mass and/or reducing pancreatic cell damage in a subject by administering the dietary fiber composition and metformin, sitagliptin, or a combination thereof.

In some embodiments, the methods of the invention are effective in increasing lean body mass in a subject by administering the dietary fiber composition and sitagliptin.

In some embodiments, the methods of the invention are effective in lowering total blood cholesterol in a subject by administering the dietary fiber composition sitagliptin.

In some embodiments, the methods of the invention are effective in preserving liver function and/or reducing liver damage in a subject by administering the dietary fiber composition and sitagliptin.

In some embodiments, the methods of the invention are effective in preserving renal function and/or reducing kidney damage in a subject by administering the dietary fiber composition and sitagliptin.

In another aspect, the invention provides a kit for preventing, treating, or ameliorating one or more symptoms associated with a metabolic disease or disorder, the kit comprising: (i) a dietary fiber composition comprising from about 48% to about 90% (w/w) glucomannan, from about 5% to about 20% (w/w) xanthan gum, and from about 5% to about 30% (w/w) alginate; and (ii) at least one of metformin, sitagliptin, or a combination thereof. In some embodiments, the kit comprises a pharmaceutical composition comprising a combination of the dietary fiber composition and metformin. In some embodiments, the kit comprises a pharmaceutical composition comprising a combination of the dietary fiber composition and sitagliptin. In some embodiments, the kit comprises a pharmaceutical composition comprising a combination of the dietary fiber composition, metformin and sitagliptin.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
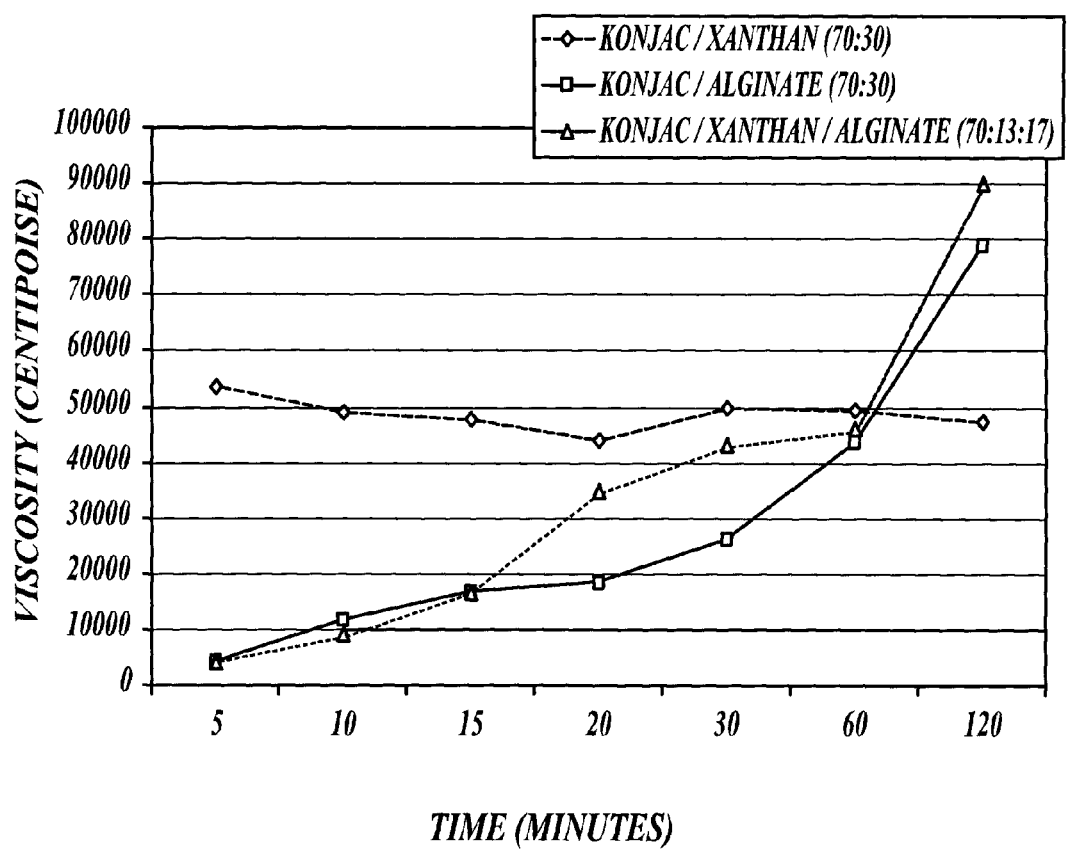
FIG. 1 graphically illustrates the viscosity profile of various fiber blends over time in distilled water, as described in EXAMPLE 1.

The present invention provides compositions and methods effective to delay the onset, slow the progression, and/or ameliorate at least one of the symptoms of a metabolic disease or disorder, such as metabolic syndrome or type II diabetes.

As used herein, the term "metabolic syndrome" refers to one or more of the following symptoms: an increase in visceral obesity, serum glucose, and insulin levels, along with hypertension and dyslipidemia (E. J. Gallagher et al., *Endocrinol. Metab. Clin. North Am.* 37:559-79 (2008)). Elevated serum glucose and elevated insulin levels are sometimes referred to as hyperglycemia and hyperinulinemia, respectively. Metabolic syndrome is a name for a group of symptoms that occur together and are associated with the increased risk of developing coronary artery disease, stroke, and type II diabetes. The symptoms of metabolic syndrome include extra weight around the waist (central or abdominal obesity), high blood pressure, high triglycerides, insulin resistance, low HDL cholesterol, and tissue damage caused by high glucose. It is believed that insulin resistance is the main cause of metabolic syndrome.

As used herein, the term "ameliorate at least one of the symptoms of metabolic disease or disorder," includes symptomatic therapy to lessen, alleviate, or mask the symptoms of the disease or disorder, as well as therapy for preventing, lowering, stopping, or reversing the progression of severity of the condition or symptoms being treated. As such, the term "treatment" includes both medical therapeutic treatment of an established condition or symptoms and/or prophylactic administration, as appropriate.

As used herein, the term "treating" also encompasses, depending on the condition of the subject in need thereof, preventing the metabolic disease or disorder, or preventing one or more symptoms associated with the pathology of the metabolic disease or disorder, including onset of the metabolic disease or disorder or of any symptoms associated therewith, as well as reducing the severity of the metabolic disease or disorder or preventing a recurrence of one or more symptoms associated with the metabolic disease or disorder.

As used herein, the term "dyslipidemia" refers to abnormally high levels of LDL (i.e., LDL over 100 mg/dL) and/or abnormally low levels of HDL (i.e., HDL lower than 40 mg/dL), which encompasses hyperlipidemia, hypolipidemia, elevated triglycerides, hypercholesterolemia, hyperglyceridemia and hypertriglyceridemia.

As used herein, the terms "combination therapy," "co-administration", "co-administering", "administration with", "administering", "combination" and/or "co-therapy", are intended to encompass administration of each agent in a sequential manner in a regimen that will provide beneficial effects of the drug combination, and is also intended to encompass co-administration of these agents in a substantially simultaneous manner.

As used herein, the term "therapeutically effective amount" refers to the amount of the subject compound or pharmaceutical composition that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the metabolic disease or condition being treated. The therapeutically effective amount will vary depending on the compound, the disease and its severity and the age, weight, etc., of the mammal to be treated.

As used herein, the term "glucomannan" refers to a water-soluble dietary fiber with β-(1,4)-linked-D-mannose and β-(1,4)-linked-D-glucose residues in approximately 3:1 ratio and various α-linked galactose end groups. It is most commonly isolated from konjac root (Amorphophallus konjac), but can also be isolated from other plant sources.

As used herein, the term "xanthan gum" refers to a heteropolysaccharide containing glucose, mannose, potassium or sodium glucuronate, acetate, and pyruvate.

As used herein, the term "alginate" refers to a mixed polymer of mannuronic acid and guluronic acid.

As used herein, the term "fiber blend" refers to a mixture of fibers.

As used herein, the term "viscous fiber blend" ("VFB") refers to a mixture of glucomannan, xanthan gum, and alginate.

As used herein, the term "viscous fiber complex" ("VFC") refers to an interlocking matrix of the three components glucomannan, xanthan gum, and alginate, in which the components have been processed in a manner (e.g., granulation) that allows them to interact to form a novel ingredient rather than a mixture of three separate components by forming secondary and tertiary interactions (junction zones and networks) between the raw ingredients that prevent the individual components from exhibiting the properties that they would each show in their pure state.

As used herein, the term "synergistic" refers to the combination of the dietary fiber composition and at least one of metformin, sitagliptin, or a combination thereof, which are used in the treatment of a metabolic disease or disorder such as metabolic syndrome or type II diabetes, either in the form of a pharmaceutical composition, combination product, or kit according to the invention, having an efficacy for the treatment of the metabolic disease or disorder that is greater than would be expected from the sum of their individuals effects. The synergistic effects of the embodiments of the present invention encompass additional unexpected advantages for the treatment of metabolic syndrome or disease. Such additional advantages may include, but are not limited to, lowering the required dose of one or more of the active compounds of the combination, reducing the side effects of one or more of the active compounds of the combination, or rendering one or more of the active compounds more tolerable to the patient in need of metabolic syndrome or disease therapy.

In one aspect, the invention provides a pharmaceutical composition compounded for the prevention, treatment or amelioration of one or more symptoms associated with a metabolic disease or disorder, such as metabolic syndrome or type II diabetes. The pharmaceutical composition according to this aspect of the invention comprises (i) a dietary fiber composition; and (ii) at least one of metformin, sitagliptin, or a combination thereof. In some embodiments, the pharmaceutical composition comprises a combination of a dietary fiber composition and metformin. In some embodiments, the pharmaceutical composition comprises a combination of a dietary fiber composition and sitagliptin. In some embodiments, the pharmaceutical composition comprises a combination of a dietary fiber composition, metformin and sitagliptin.

Dietary Fiber Composition

The pharmaceutical composition for use in the compositions, kits and methods of the invention comprises a highly viscous polysaccharide dietary fiber composition comprising from about 48% to about 90% (w/w) glucomannan, from about 5% to about 20% (w/w) xanthan gum, and from about 5% to about 30% (w/w) alginate.

As described in pending U.S. patent application Ser. No. 11/400,768, filed on Apr. 7, 2006, pending U.S. patent application Ser. No. 11/830,615, filed on Jul. 30, 2007, pending U.S. patent application Ser. No. 13/045,285, filed on Mar. 10, 2011, and pending U.S. patent application Ser. No. 13/277,038, filed on Oct. 19, 2011, each of which is hereby incorporated by reference, a highly viscous polysaccharide dietary fiber composition comprising a fiber blend (VFB), or complex thereof (VFC), produced by combining from about 48% to about 90% (w/w) glucomannan, from about 5% to about 20% (w/w) xanthan gum, and from about 5% to about 30% (w/w) alginate, has been developed, commercially referred to as "PolyGlycopleX®" or "PGX®," that possesses a very high water hold capacity and gel-forming property. The constituent polysaccharide components of this fiber composition are complementary to each other and act synergistically to form strong interactions that lead to a level of viscosity that is three to five times higher than any other currently known polysaccharide. As described in Example 6 of U.S. patent application Ser. No. 13/045,285, it has been determined that when processed (e.g., granulated), the three components glucomannan, xanthan gum, and alginate interact to form a novel ingredient (complex ("VFC")) rather than a mixture of 3 separate components by forming secondary and tertiary interactions (junction zones and networks) between the raw ingredients that prevent the individual components from exhibiting the properties that they would each show in their pure state.

This highly viscous dietary fiber composition imparts a significant increase in the viscosity of gastrointestinal contents at a lower gravimetric quantity than that which would be required with other soluble fibers. This highly concentrated property allows this fiber composition to impart substantial physiological effects at doses that are significantly lower than other soluble fibers, thus making it easier to incorporate meaningful quantities of this material into pharmaceutical compositions.

In one embodiment, the dietary fiber composition contained in the pharmaceutical composition is processed via granulation to produce an interlocking matrix of the three components (i.e., a complex (VFC)). As used herein, "granulation" refers to any process of size enlargement in which small particles are gathered together into larger, permanent aggregates. Granulation may be accomplished by agitation in mixing equipment, by compaction, extrusion, or globulation. The dietary fiber compositions may be granulated using various mesh sizes. The term "mesh" refers to the size of the particle as determined by its ability to pass through a screen having holes of defined dimensions. The mesh sizes used herein are Tyler equivalents, as set forth in Table 21-12 of the *Chemical Engineers Handbook* (5th ed., Perry & Chilton, eds.). The larger the granulation (i.e., the smaller the mesh size) of the dietary fiber composition/complex, the longer it takes for a desired viscosity to be attained. In some embodiments, the dietary fiber composition/complex is granulated using a combined mesh size by separating granulated materials by their particle size, then recombining the particle-size separated granules to give the desired viscosity profile. For example, a combined mesh size of 30 to 60 is obtained by combining granules of 30 mesh (about 600 microns), granules of about 40 mesh (about 400 microns), granules of about 50 mesh, and granules of about 60 mesh (250 microns).

The proportions of glucomannan, xanthan gum, and alginate in the viscous dietary fiber blend/complex (VFB/C) contained in the dietary fiber composition may be from about 48% to about 90% of glucomannan (such as from about 60% to about 80%, or from about 60% to about 90%, or from about 65% to about 75%, or from about 50% to about 80%, or from about 50% to about 70%, or about 70%), from about 5% to about 20% of xanthan gum (such as from about 10% to about 20% or from about 11% to about 13%, or from about 13% to about 17%, or about 13%, or about 17%), and from about 5% to about 30% of alginate (such as from about 10% to about 20% or from about 13% to about 17%, or about 13%, or about 17%). In some embodiments, proportions of glucomannan, xanthan gum, and alginate in the dietary compositions contained in the pharmaceutical compositions are about 70% glucomannan, from about 13% to about 17% xanthan gum, and from about 13% to about 17% alginate.

Metformin

As used herein, "metformin" refers to metformin hydrochloride, (systematic (IUPAC) name N,N-dimethylimidodicarbonimidic diamide hydrochloride), which is an oral antihyperglycemic drug in the biguanide class used in the management of type II diabetes. Metformin hydrochloride, USP is a white crystalline compound with a molecular formula of $C_4H_{11}N_5$+HCl and a molecular weight of 165.63, and is freely soluble in water.

Metformin is sold under several trade names, including GLUCOPHAGE, RIOMET, FORTAMET, GLUMETZA, OBITMET, GLUFORMIN, DIANBEN, DIABEX AND DIAFORMIN.

Metformin IR (immediate release) is available in available 500 mg, 850 mg, and 1000 mg tablets. The maximum recommended daily dosage of metformin hydrochloride tablets is 2550 mg in adults and 2000 mg in pediatric patients (10-16 years old). Typically adult dosing is 500 mg twice a day as a minimum up to a total of 2000 mg/day, given in divided doses. Dosing is determined on an individual basis, wherein fasting plasma glucose may be used to determine the therapeutic response to identify the minimum effective dose for the patient. Thereafter, glycosylated hemoglobin may be measured at intervals of approximately three months. The therapeutic goal is to decrease both fasting plasma glucose and glycosylated hemoglobin levels to normal or near normal by using the lowest effective dose, either when used as monotherapy or in combination with a dietary fiber composition of the invention.

Metformin improves hyperglycemia by suppressing glucose production by the liver (Kirpichnikov, D., et al., *Ann Intern Med* 137(1):25-33 (2002)). In addition to suppressing hepatic glucose production, metformin increases insulin sensitivity, enhances peripheral glucose uptake, increases fatty acid oxidation and decreases absorption of glucose from the gastrointestinal tract (Collier, C., et al., *Am J Physiol Endorinol Metab* 291(1):E182-189 (2006)). Metformin is not metabolized and is cleared from the body by tubular secretion and excreted unchanged in the urine. The average half-life in plasma is 6.2 hours. See Bristol-Myers Squibb GLUCOPHAGE Label information, Aug. 27, 2008 (www.accessdata.fda.gov).

The usual synthesis of metformin involves the reaction of dimethylamine hydrochloride and 2-cyanoguanidine (dicyandiamide) with heating, as described in Werner, E., et al., *J Chem Soc Transactions* 121:1790-5 (1921); Shapiro, S., et al., *J Am Chem Soc* 81(9):2220-5 (1959), both of which are hereby incorporated herein by reference. As described in Patent FR 2322860 (1975) and Pharmaceutical Manufacturing Encyclopedia Vol. 3, Norwich, N.Y., p. 2208 (2007), both of which are hereby incorporated herein by reference, equimolar amounts of dimethylamine and 2-cyanoguanidine are dissolved in toluene with cooling to make a concentrated solution, and an equimolar amount of hydrogen chloride is slowly added. The mixture begins to boil on its own, and after cooling, metformin hydrochloride precipitates with a 96% yield.

Sitagliptin

As used herein, "sitagliptin" refers to sitagliptin, and pharmaceutically acceptable salts thereof, e.g., sitagliptin phosphate. Sitagliptin (systematic IUPAC name (R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine) is an oral antihyperglycemic of the dipeptidyl peptidase-4 (DPP-4) inhibitor class, marketed under the trade name JANUVIA. This drug is used either alone or in combination with other oral antihyperglycemic agents such as metformin for the treatment of type II diabetes. There have been reports of pancreatitis (some fatal) in people treated with sitagliptin. See Olansky, L., et al., *J Diabetes Sci Technol* 4(1):228-9 (2010); Merck & Co. (www.januvia.com). There have also been reports of worsening renal function after taking JANUVIA, including acute renal failure, sometimes requiring dialysis.

Sitagliptin was approved by the FDA in 2006 and is marketed in the U.S. as JANUVIA by Merck & Co. In 2007, the FDA approved an oral combination of sitagliptin and metformin marketed in the U.S. as JANUMET.

Sitagliptin works to competitively inhibit the enzyme dipeptidyl peptidase 4 (DPP-4), which breaks down the gluco-incretins GLP-1 (glucopgen-like peptide 1) and GIP (gastric inhibitory peptide), gastrointestinal hormones released in response to a meal (Herma, G., et al., *J Clin Pharmacol* 46(8):876-86 (2006)). By preventing GLP-1 and GIP inactivation, DPP-4 inhibitors increase the secretion of insulin, causing glucose uptake by cells, which decreases serum glucose levels, and suppress the release of glucagon by the pancreas which drives blood glucose levels towards normal.

The recommended dosage of sitagliptin for an adult human subject is 100 mg once daily. Decreased dosages are recommended for patients with moderate to severe renal insufficiency.

JANUVIA tablets contain 25, 50 or 100 mg sitagliptin phosphate, which is described chemically as 7-[(3R)-3-amino-1-oxo-4-(2,4,5-trifluorophenyl)buty]-5,6,7,8-tetrahydro-3-(trifluoromethyl)-1,2,4-triazolo[4,3-a]pyrazine phosphate (1:1) monohydrate. The empirical formula is $C_{16}H_{15}F_6N_5O$—$H_3PO_4$—$H_2O$ and the molecular weight is 523.32. Sitagliptin phosphate monohydrate is a white crystalline non-hygroscopic powder. It is soluble in water. Synthesis of sitagliptin phosphate is described, e.g., in U.S. Pat. No. 6,699,871, incorporated herein by reference.

Pharmaceutical Compositions

In some embodiments of the invention, the pharmaceutical composition comprises a combination of (i) a dietary fiber composition comprising from about 48% to about 90% (w/w) glucomannan, from about 5% to about 20% (w/w) xanthan gum, and from about 5% to about 30% (w/w) alginate; and (ii) at least one of metformin, sitagliptin, or a combination thereof. In some embodiments, the pharmaceutical composition comprises the dietary fiber composition and metformin. In some embodiments, the pharmaceutical composition comprises the dietary fiber composition and sitagliptin. In some embodiments, the pharmaceutical composition comprises the dietary fiber composition, metformin, and sitagliptin.

In addition to the active ingredients, the pharmaceutical compositions of the invention may include suitable carriers and excipients.

In some embodiments, the dietary fiber composition comprises from about 50% to about 80% (w/w) glucomannan, from about 10% to about 20% (w/w) xanthan gum, and from about 10% to about 20% (w/w) alginate. In some embodiments, the dietary fiber composition is granulated. In some embodiments, the pharmaceutical composition further comprises at least one lipid or blend thereof, wherein the lipid or blend thereof comprises at least 20% (w/w) of the total dietary fiber composition. In some embodiments, the pharmaceutical composition is contained in an outer soft gelatin capsule. In some embodiments, the pharmaceutical composition is compounded in a tablet. In some embodiments, the pharmaceutical composition is formulated into a powder.

As described herein, the pharmaceutical compositions of the invention may be used in the methods and kits of the invention. In some embodiments, the pharmaceutical composition of the invention is administered to a subject in need thereof at least once per day. In some embodiments, the pharmaceutical composition of the invention is administered twice a day, preferably once in the morning and once in the afternoon/evening. A typical treatment regime for the pharmaceutical composition will continue from at least two weeks to eight weeks or longer.

The pharmaceutical compositions of the present invention may be prepared by any of the methods well known in the art of pharmacy. The pharmaceutical compositions may be prepared by combining an effective amount of a dietary fiber composition comprising a viscous fiber blend (VFB), or complex thereof (VFC) comprising glucomannan, xanthan gum, and alginate, with an effective amount of at least one of metformin, sitagliptin, or a combination thereof. In some embodiments, the method of preparing a pharmaceutical composition comprises the step of combining an effective amount of a dietary fiber composition comprising a fiber complex (VFC) formed from a viscous fiber blend (VFB) comprising glucomannan, xanthan gum, and alginate with metformin. In some embodiments, the method of preparing a pharmaceutical composition comprises the step of combining an effective amount of a dietary fiber composition comprising a fiber complex (VFC) formed from a viscous fiber blend (VFB) comprising glucomannan, xanthan gum, and alginate with sitagliptin. In some embodiments, the method of preparing a pharmaceutical composition comprises the step of combining an effective amount of a dietary fiber composition comprising a fiber complex (VFC) formed from a viscous fiber blend (VFB) comprising glucomannan, xanthan gum, and alginate, with metformin and sitagliptin.

In some embodiments, the pharmaceutical composition is compounded for the prevention, treatment, or amelioration of one or more symptoms associated with a metabolic disease or disorder. In some embodiments, the dietary fiber composition added to the pharmaceutical composition comprises a fiber blend (VFB), or a fiber complex (VFC) formed from the fiber blend (e.g., granulated VFB), comprising from about 48% to about 90% (w/w) glucomannan (such as from about 60% to about 80%, or from about 60% to about 90%, or from about 65% to about 75%, or from about 50% to about 80%, or from about 50% to about 70%, or about 70%), from about 5% to about 20% (w/w) xanthan gum (such as from about 10% to about 20%, or from about 11% to about 13%, or from about 13% to about 17%, or about 13%, or about 17%), and from about 5% to about 30% (w/w) alginate (such as from about 10% to about 20% or from about 13% to about 17%, or about 13%, or about 17%). In some embodiments, proportions of glucomannan, xanthan gum, and alginate in the fiber blend, or in the fiber complex formed from the fiber blend, contained in the dietary fiber composition are about 70% glucomannan, from about 13% to about 17% xanthan gum, and from about 13% to about 17% alginate.

Formulations

The combinations according to the invention may be administered by any suitable route. In some embodiments, the pharmaceutical compositions according to this invention are formulated for oral administration. Tablets, coated tablets (dragees), pills, cachets, capsules (caplets), granules, solutions, emulsions and suspensions are e.g. suitable for oral administration. In particular, said formulations can be adapted so as to represent, for example, an enteric form, an immediate release form, a delayed release form, a repeated dose release form, a prolonged release form or a sustained release form. Said forms can be obtained, for example, by coating tablets, by dividing tablets into several compartments separated by layers disintegrating under different conditions (e.g., pH conditions) or by coupling the active compound to a biodegradable polymer.

The pharmaceutical compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules, lozenges or the like in the case of solid compositions.

Suitable excipients or carriers and methods for preparing administrable compositions are known or apparent to those skilled in the art and are described in more detail in such publications as Remington's Pharmaceutical Science, Mack Publishing Co, NJ (1991).

The amount administered depends on the formulation, route of administration, etc. and is generally empirically determined in routine trials, and variations will necessarily occur depending on the target, the host, and the route of administration, etc. In a particular embodiment, unit dosage forms are packaged in a multipack adapted for sequential use, such as blister pack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the active ingredient. Thereafter, the dosage is increased by small amounts until the optimum effect under the circumstances is reached. For convenience, the total daily dosage may be divided and administered in portions during the day if desired.

Kits

In another aspect, the invention provides kits for preventing, treating, or ameliorating one or more symptoms associated with a metabolic disease or disorder, the kit comprising: (i) a dietary fiber composition comprising from about 48% to about 90% (w/w) glucomannan, from about 5% to about 20% (w/w) xanthan gum, and from about 5% to about 30% (w/w) alginate; and (ii) at least one of metformin, sitagliptin, or a combination thereof. In some embodiments, the kit comprises a pharmaceutical composition comprising a combination of a dietary fiber composition and metformin. In some embodiments, the kit comprises a pharmaceutical composition comprising a combination of a dietary fiber composition and sitagliptin. In some embodiments, the kit comprises a pharmaceutical composition comprising a combination of a dietary fiber composition, metformin and sitagliptin. In some embodiments, the kit comprises a dietary fiber composition and a pharmaceutical composition comprising a combination of metformin and sitagliptin.

In some embodiments, the kit comprises a unit dosage comprising a dietary fiber composition, and a separate unit dosage comprising at least one of metformin, sitagliptin, or a combination thereof.

Methods for Preventing, Treating or Ameliorating One or More Symptoms Associated with a Metabolic Disease or Disorder In another aspect, the present invention provides a method for preventing, treating, or ameliorating one or more symptoms associated with a metabolic disease or disorder, such as metabolic syndrome or type II diabetes.

Metabolic disease and disorders generally adversely affects the way the body uses sugars and starches which, during digestion, are converted into glucose. Insulin, a hormone produced by the pancreas, makes the glucose available to the body's cells for energy. The net effect of insulin is to promote the storage and use of carbohydrates, protein and fat. Insulin secretion from the pancreas is predominantly controlled by blood glucose levels. In type II diabetes, e.g., the pancreas retains the ability to produce insulin and in fact may produce higher than normal amounts of insulin, but the amount of insulin is less than fully effective, due to cellular resistance to insulin.

Metabolic disease and disorders are marked by hyperglycemia (high serum glucose levels). Uncontrolled hyperglycemia can damage the cells of the pancreas, which produce insulin (the β-islet cells), the liver, and the kidney, and in the long term create greater insulin deficiencies.

In metabolic disease and disorders, there are widespread abnormalities caused by (1) a reduced entry of glucose into various "peripheral" tissues and (2) an increased liberation of glucose into the circulation from the liver, which results in an extracellular glucose excess (hyperglycemia) and an intracellular glucose deficiency. There is also a decrease in the entry of amino acids into muscle and an increase in lipolysis. Dyslipidemia is also a complication of metabolic disease and disorders.

The present invention provides methods for preventing, treating, or ameliorating one or more symptoms associated with a metabolic disease or disorder through modification and regulation of glucose and lipid metabolism, generally reducing insulin resistance, hyperglycemia, hyperinsulinemia, obesity, hyperlipidemia, hyperlipoproteinemia (such as chylomicrons, VLDL and LDL), and regulating body fat and, more generally, lipid stores.

As described in the Examples, the methods of the invention are effective in lowering and stabilizing blood glucose levels, and as a result, are effective in preserving pancreatic, liver, and kidney function and reducing damage to the pancreas, liver, and kidneys.

The methods according to this aspect of the invention comprises co-administering to a human subject in need thereof (i) a dietary fiber composition comprising from about 48% to about 90% (w/w) glucomannan from about 5% to about 20% (w/w) xanthan gum, and from about 5% to about 30% (w/w) alginate; and (ii) an effective amount of at least one of metformin, sitagliptin, or a combination thereof.

In some embodiments, the method comprises administering a dietary fiber composition comprising a viscous fiber blend (VFB) or complex thereof (VFC, such as, for example, granulated VFB), comprising from about 48% to about 90% (w/w) glucomannan, from about 5% to about 20% (w/w) xanthan gum, and from about 5% to about 30% (w/w) alginate to a human subject in need thereof at a dosage of from 1.0 g to 50 g VFB/C per day, such as from about 2.5 g to about 50 g VFB/C per day, from about 5 g to about 50 g VFB/C per day, from about 10 g to about 35 g VFB/C per day, from about 12 g to 35 g VFB/C per day, or such as from about 15 g to 35 g VFB/C per day, such as from about 20 g to 35 g VFB/C per day, such as from about 12 g to about 25 g VFB/C per day, such as from about 15 g to about 25 g VFB/C per day, in combination with metformin, sitagliptin, or a combination thereof, for a time period effective to prevent, treat or ameliorate one or more symptoms associated with the metabolic disease or disorder in the subject.

In some embodiments, the dietary fiber composition comprises from about 50% to about 80% (w/w) glucomannan, from about 10% to about 20% (w/w) xanthan gum, and from about 10% to about 20% (w/w) alginate. In some embodiments, the dietary fiber composition is granulated.

In some embodiments, the method comprises administering the dietary fiber composition to the subject in an amount from about 1 g to about 50 g per day for a time period of at least two weeks.

In some embodiments, the method comprises co-administering the dietary fiber composition with metformin. In some embodiments, the metformin is administered to the subject in an amount from about 50 mg to 2000 mg per day for a time period of at least two weeks.

In some embodiments, the method comprises co-administering the dietary fiber composition with sitagliptin. In some embodiments, the sitagliptin is administered to the subject in an amount from about 5 mg to 100 mg per day for a time period of at least two weeks.

In some embodiments, the method comprises co-administering the dietary fiber composition with metformin and sitagliptin. In some embodiments, the method comprises administering metformin in an amount from about 50 mg to 2000 mg per day, and administering sitagliptin in an amount from about 5 mg to 100 mg per day for a time period of at least two weeks.

The dietary fiber composition may be co-administered with metformin and/or sitagliptin by simultaneous dosing of the individual components, or separate dosing. The individual components may be administered sequentially, in any order. The individual components may be administered in a single composition comprising the individual components.

The dietary fiber composition may be administered to the subject before the administration of metformin, simultaneously with the administration of metformin, or after the administration of metformin. In some embodiments, the dietary fiber composition and metformin are co-administered in a single pharmaceutical composition.

The dietary fiber composition may be administered to the subject before the administration of sitagliptin, simultaneously with the administration of sitagliptin, or after the administration of sitagliptin. In some embodiments, the dietary fiber composition and sitagliptin are co-administered in a single pharmaceutical composition.

In some embodiments, the dietary fiber composition, metformin, and sitagliptin are co-administered in a single pharmaceutical composition. In some embodiments, metformin and sitagliptin are administered in a single pharmaceutical composition, and the dietary fiber composition is administered separately.

In some embodiments the methods of the invention comprise lowering elevated blood glucose levels in the subject by administering the dietary fiber composition and metformin, sitagliptin, or a combination thereof.

In some embodiments the methods of the invention comprise preserving pancreatic islet function by preserving islet cell mass and/or reducing pancreatic cell damage in the subject by administering the dietary fiber composition and metformin, sitagliptin, or a combination thereof.

In some embodiments the methods of the invention comprise increasing lean body mass in the subject by administering the dietary fiber composition and sitagliptin.

In some embodiments the methods of the invention comprise lowering the total blood cholesterol in the subject by administering the dietary fiber composition and sitagliptin.

In some embodiments the methods of the invention comprise preserving liver function and/or reducing liver damage in the subject by administering the dietary fiber composition and sitagliptin.

In some embodiments the methods of the invention comprise preserving renal function and/or reducing kidney damage in the subject by administering the dietary fiber composition and sitagliptin.

In some embodiments the subject has type II diabetes.

Metformin, sitagliptin, and metformin combined with sitagliptin, are known pharmaceutical compositions used to treat or control the symptoms of type II diabetes by lowering elevated blood glucose levels. However, applicants have unexpectedly discovered, as illustrated in the following examples, that the administration of the dietary fiber compositions of the invention, in combination with metformin, or in combination with sitagliptin, or in combination with both metformin and sitagliptin, results in a statistically significant beneficial effect, when compared to the administration of each active ingredient (dietary fiber composition, metformin, or sitagliptin) alone, or when compared to administration of the combination of metformin and sitagliptin.

The invention will be more readily understood by reference to the following examples, which are included merely for purposes of illustration of certain aspects and embodiments of the present invention and are not intended to limit the invention.

EXAMPLE 1

This Example describes the selection of fibers in an exemplary dietary fiber composition, referred to as a viscous fiber blend (VFB), and granulation thereof to form a viscous fiber complex (VFC), which provides desirable viscosity profiles under gastric and intestinal conditions.

Background/Rationale:

In formulating VFB, the main objective was to produce a fiber blend that would increase in viscosity substantially over a 15- to 60-minute time period. To enhance palatability, it is desirable for the initial viscosity of the fiber blend to be thinner and for the maximum thickness of the fiber blend to occur in the stomach and intestines of the subject. Therefore, in selecting fibers, the blend also had to maintain or, more desirably, increase in viscosity under both gastric (acidic) and intestinal conditions. The high viscosity at this point in the digestive system would contribute to a feeling of fullness and also help with blood sugar regulation by modulating carbohydrate absorption.

After a significant amount of experimentation (data not shown), a fiber blend was developed that comprises glucomannan, alginate, and xanthan gum. It was determined that glucomannan was a desirable ingredient for the fiber blend due to its high viscosity property. It also had a very smooth texture that enhanced palatability. Alginate helped moderate the strong thickening characteristic of glucomannan and it also achieved a more palatable viscosity during the initial stages of ingestion. Xanthan, too, was selected as part of the blend since it was the only fiber that seemed to curb and thin out glucomannan near the end of the viscosity test (30-60 minutes).

Figure 2:
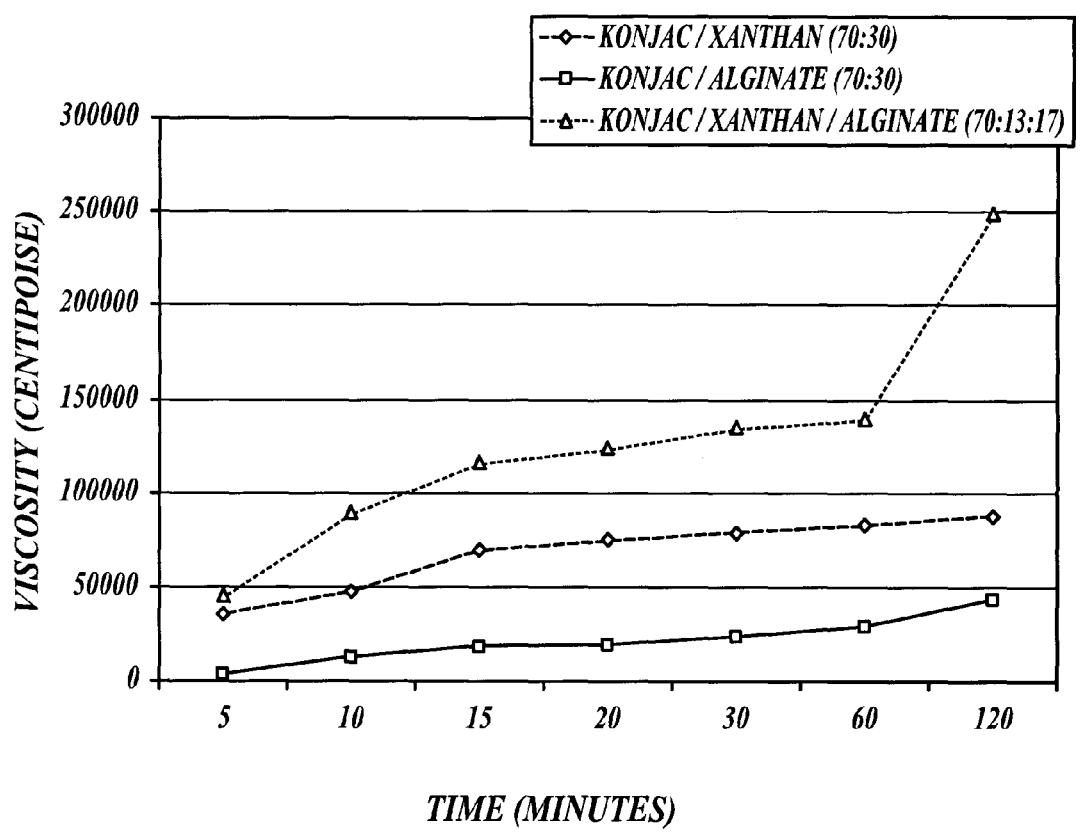
FIG. 2 graphically illustrates the viscosity profile of various fiber blends over time under gastric conditions, as described in EXAMPLE 1.

The final composition of VFB created was from 48%-90% glucomannan, from 5%-20% xanthan gum, and from 5%-30% alginate. When glucomannan, xanthan, and alginate are combined at these ratios to produce VFB, this composition exhibits unexpectedly high viscosity values after 120 minutes when blended with water, as shown in FIG. 1 and described in EXAMPLE 2. The VFB also produces unexpectedly high viscosity values after 10 minutes when blended with gastric juice, as shown in FIG. 2 and described in EXAMPLE 2.

At a lower glucomannan ratio, the product would not reach desired thickness. At a higher xanthan ratio, the product also did not reach the desired thickness. At a lower xanthan ratio, the fiber blend thickened too quickly. Alginate also had an important role in enhancing palatability by decreasing viscosity during the initial stages of the product.

In a preferred embodiment, VFB compositions were produced that contained 60%-80% glucomannan, 10%-20% xanthan gum, and 10%-20% alginate that had the desirable characteristics mentioned above. For example, a VFB composition was produced that contained 70% glucomannan, 13% xanthan gum, and 17% alginate with desirable characteristics as described herein. Another VFB composition was produced that contained 70% glucomannan, 17% xanthan gum, and 13% alginate with similar desirable properties.

The viscosity profile of VFB (70% glucomannan, 13% xanthan gum, and 17% alginate) in comparison to a competing commercial fiber is presented in TABLE 1.

TABLE 1

Viscosity Profile of VFB vs. Commercial Fiber Blend

| | Viscosity (centipoise) at Different Time Points (minutes) | | | | | | | | | |
|---|---|---|---|---|---|---|---|---|---|---|
| | 5 | 10 | 15 | 20 | 25 | 30 | 45 | 60 | 75 | 90 |
| VFB | 600 | 900 | 1,000 | 1100 | 1250 | 1300 | 1500 | 1650 | 1750 | 1850 |
| Commercial Fiber | 550 | 800 | 1,000 | 1100 | 1150 | | 1350 | 1550 | 1550 | 1750 |

One of the differences between VFB and the commercial fiber is how they react under simulated digestive conditions. As shown in TABLE 2, VFB has the ability to increase in thickness under gastric conditions. TABLE 2 compares the viscosity profiles of VFB (70% glucomannan, 13% xanthan gum, and 17% alginate) and the commercial fiber when 2 g of fiber are added to 200 g of distilled water with 10 drops of phosphoric acid.

TABLE 2

Viscosity Comparison of VFB and Commercial Fiber Under Gastric Conditions

| | Viscosity (centipoise) at Different Time Points (minutes) | | | | | | |
|---|---|---|---|---|---|---|---|
| | 5 | 10 | 15 | 20 | 25 | 30 | 45 |
| VFB | 1000 | 2800 | 4100 | 5100 | 6150 | 6500 | 7150 |
| Commercial Fiber | 400 | 800 | | 2400 | 3500 | 4450 | 6750 |

TABLE 3 compares the viscosity profile of VFB (70% glucomannan, 13% xanthan gum, and 17% alginate) compared with the commercial fiber under intestinal conditions. Two grams of fiber were added to 200 g of intestinal fluid. Intestinal fluid was made by dissolving 6.8 g of monobasic potassium phosphate in 250 mL of water, mixing, and adding 190 mL of 0.2 N NaOH and 400 mL of water. Ten grams of pancreatin was added, followed by mixing and adjusting the pH with 0.2 N NaOH to a pH of 7.5±0.1. The solution was diluted with water to 1,000 mL (United States Pharmacopoeia).

TABLE 3

Viscosity Profile Comparison of VFB and Commercial Fiber Under Intestinal Conditions

| | Viscosity (centipoise) at Different Time Points (minutes) | | | | | | | | |
|---|---|---|---|---|---|---|---|---|---|
| | 3 | 5 | 10 | 15 | 20 | 25 | 30 | 45 | 60 |
| VFB | 2600 | 6600 | 15000 | 35000 | 39250 | 41000 | 66500 | 69500 | 72000 |
| Commercial Fiber | 1150 | 1350 | 1700 | 2250 | 2600 | 3000 | 3000 | 5850 | 7900 |

These test results show that under simulated gastric and intestinal conditions, the VFB fiber blend thickened more than the commercial fiber blend, indicating that VFB has a higher viscosity than the commercial fibers in the stomach and may continue to thicken under intestinal conditions.

In order to create a product that is more appealing to the consumer, granulated VFB was used to further delay viscosity during the initial stages of ingestion. Granulation is achieved through addition of 30-60% (w/w) water to the VFB blend and then drying off the added water. This process is typically performed through mechanical granulators, fluid-bed granulator/dryers, mechanical agglomerators, or simple mixing followed by oven or vacuum drying.

Non-granulated VFB is quite fine and tends to clump when added with water. It absorbs moisture so quickly that the water actually encapsulates the powder. However, granulated VFB avoids this problem as the larger granules remain separated from each other when wet. Slowly the slurry thickens as the VFB granules gradually dissolve into water.

Determining the proper mesh size of VFB is important in the granulation process. Thirty mesh particles are about 600 microns in diameter, 40 mesh particles are about 400 microns in diameter, 50 mesh particles are about 300 microns in diameter, 60 mesh particles are about 250 microns in diameter, and 80 mesh particles are about 180 microns in diameter. Although it slows viscosity increase, the granulated VFB product still increases to the desirable thickness responsible for generating that full feeling and also regulating blood sugar levels by slowing down absorption of carbohydrates in the intestines. The larger the granulation (i.e., the smaller the mesh size), the more the increase in viscosity is delayed, as shown in TABLE 4.

TABLE 4

Viscosity Comparison of VFB Granulated Using Different Mesh Sizes

| | Viscosity (centipoise) at Different Time Points (minutes) | | | | | | |
|---|---|---|---|---|---|---|---|
| | 5 | 10 | 15 | 20 | 30 | 60 | 120 |
| Granulated VFB mesh size 30 (stirred) | 0 | 35 | 100 | 195 | 425 | 3760 | 45240 |
| Granulated VFB mesh size 40 (stirred) | 55 | 220 | 490 | 2095 | 6545 | 28780 | >90000 |
| Granulated VFB mesh size 60 (stirred) | 590 | 4295 | 12090 | 28755 | 53035 | 82630 | >90000 |
| Non-granulated VFB (blended) | 612.5 | 1126 | 2356 | 3367.5 | 7880 | 19400 | 48860 |
| Non-granulated VFB (stirred) | 190 | 620 | 5073 | 7150 | 15380 | 56990 | >90000 |
| Granulated VFB combined mesh size 30-60 | 95 | 315 | 1115 | 4330 | 11215 | 48800 | >90000 |

A combination of 30- to 60-mesh size granulated VFB product consisting of a 1:1:1 combination of 30-, 40-, and 60-mesh size granules is desirable. A larger proportion of the smaller mesh will delay the increase in viscosity even more.

EXAMPLE 2

This example describes a comparison of the viscosity profile of an exemplary fiber blend (VFB) to other fiber blends under various conditions.

Methods:

A formulation of viscous fiber blend (VFB) was created which included 70% glucomannan (konjac), 13% xanthan gum, and 17% alginate, as described in EXAMPLE 1. The VFB was compared with a konjac/xanthan (70:30) fiber blend and a konjac/alginate (70:30) fiber blend in distilled water, gastric conditions and intestinal conditions as follows.

Compositions Tested:
(1) VFB: konjac (70%)/xanthan (13%)/alginate (17%)
(2) KX: konjac (70%)/xanthan (30%)
(3) KA: konjac (70%)/alginate (30%)

Viscosity Profile Experiments:

Five grams of test material was mixed with 350 g of fluid (either distilled water, gastric, or intestinal juice). The sample was blended for 30 seconds on low speed 2 on a Proctor/Silex blender. Viscosity readings were taken at 5, 10, 15, 20, 30, 45, 60, and 120 minutes. Gastric and intestinal fluids were prepared according to Universal Sample Preparation (USP) methodology.

Results

Figure 3:
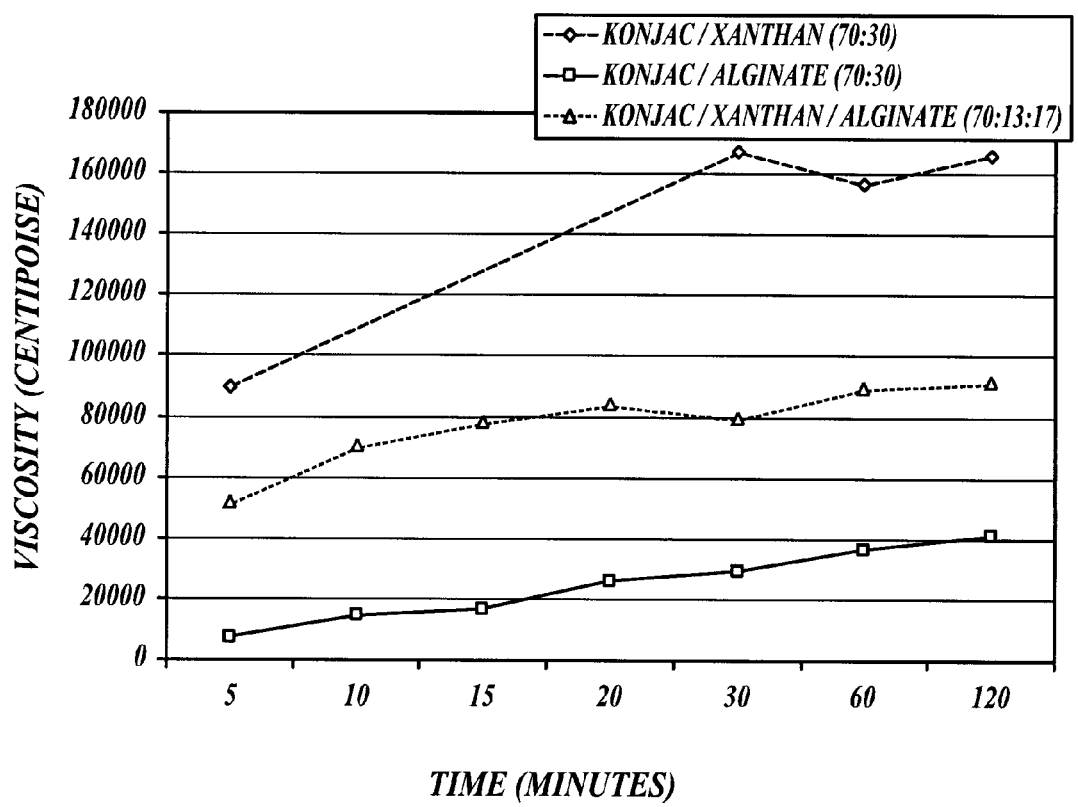
FIG. 3 graphically illustrates the viscosity profile of various fiber blends over time under intestinal conditions, as described in EXAMPLE 2.

TABLE 5 and FIG. 1 compare the viscosity profile of VFB compared with KX and KA under normal conditions (distilled water). TABLE 6 and FIG. 2 compare the viscosity profile of VFB compared with KX and KA under gastric conditions. TABLE 7 and FIG. 3 compare the viscosity profile of VFB compared with KX and KA under intestinal conditions. As shown in FIGS. 1, 2, and 3, the KA (konjac/alginate 70:30) fiber blend consistently has the lowest viscosity of the three fiber blends tested. Under neutral and gastric conditions the KX (konjac/xanthan 70:30) reaches maximum viscosity quickly (e.g., within about 15-20 minutes). The VFB blend (konjac (70%)/xanthan (13%)/alginate (17%)) starts at about the same viscosity as KA under neutral conditions, increases in viscosity over time under both gastric and intestinal conditions and eventually reaches a greater viscosity than KX under neutral and gastric conditions. This combination also produces unexpectedly high viscosity values after 10 minutes when blended with gastric juice. Therefore, the addition of alginate to the KX combination unexpectedly provides a decrease in viscosity of VFB at neutral conditions and results in a greater viscosity than KX alone over time.

TABLE 5

Viscosity Profile Comparison of VFB and Various Fiber Blends in Distilled Water

| Fiber Blend | 5 min | 10 min | 15 min | 20 min | 30 min | 60 min | 120 min | avg temp | pH |
|---|---|---|---|---|---|---|---|---|---|
| KX: konjac/xanthan (70:30) | 53380 | 49080 | 47870 | 43950 | 49810 | 49251 | 47440 | 20.2 | 6.05 |
| KA: konjac/alginate (70:30) | 3960 | 11470 | 16730 | 18420 | 25940 | 43530 | 78850 | 20.2 | 6.35 |
| VFB (konjac/xanthan/alginate (70:13:17)) | 4230 | 9230 | 16700 | 34970 | 43170 | 46010 | 90000 | 20.8 | 6.17 |

TABLE 6

Viscosity Profile Comparison of VFB and Various Fiber Blends Under Gastric Conditions

| Fiber Blend | 5 min | 10 min | 15 min | 20 min | 30 min | 60 min | 120 min | avg temp | pH |
|---|---|---|---|---|---|---|---|---|---|
| KX: konjac/xanthan (70:30) | 35500 | 48020 | 70150 | 75400 | 78720 | 83290 | 87680 | 20.3 | 1.46 |

TABLE 6-continued

Viscosity Profile Comparison of VFB and Various Fiber Blends Under Gastric Conditions

| Fiber Blend | 5 min | 10 min | 15 min | 20 min | 30 min | 60 min | 120 min | avg temp | pH |
|---|---|---|---|---|---|---|---|---|---|
| KA: konjac/alginate (70:30) | 3210 | 11820 | 17664 | 18820 | 23580 | 29130 | 43460 | 20.2 | 3.85 |
| VFB (konjac/xanthan/alginate (70:13:17)) | 44880 | 90000 | 116500 | 123600 | 135200 | 139600 | 249000 | 20.5 | 3.69 |

TABLE 7

Viscosity Profile Comparison of VFB and Various Fiber Blends Under Intestinal Conditions

| Fiber Blend | 5 min | 10 min | 15 min | 20 min | 30 min | 60 min | 120 min | avg temp | pH |
|---|---|---|---|---|---|---|---|---|---|
| KX: konjac/xanthan (70:30) | 90000 | nd | nd | nd | 167500 | 156800 | 166200 | 20.2 | 7.88 |
| KA: konjac/alginate (70:30) | 6990 | 14470 | 16350 | 26030 | 29110 | 36600 | 40900 | 20.1 | 7.89 |
| VFB (konjac/xanthan/alginate (70:13:17)) | 51490 | 70180 | 78640 | 84100 | 79480 | 90000 | 91900 | 20.5 | 7.92 |

EXAMPLE 3

This example provides exemplary embodiments of compositions comprising a dietary fiber composition (VFB/C) of the invention, and compositions comprising a dietary fiber composition combined with metformin, sitagliptin, or a combination thereof, formulated as gelatin capsules.

An exemplary dietary fiber composition is formulated as two-piece, hard-gelatin capsules, with each capsule containing 500 mg of the dietary fiber composition as shown in TABLE 8A. TABLES 8B-D provide prophetic examples of the components of pharmaceutical compositions of the invention comprising a dietary fiber composition in combination with metformin (8B), in combination with sitagliptin (8C), and in combination with metformin and sitagliptin (8D).

TABLE 8A

VFB/C Capsule Composition

| Ingredient | Amount |
|---|---|
| Glucomannan | 350 mg |
| Xanthan Gum | 85 mg |
| Alginate | 65 mg |
| Magnesium Stearate | 7 mg |
| Total | 507 mg |

TABLE 8B

VFB/C Capsule Composition with Metformin

| Ingredient | Amount |
|---|---|
| Glucomannan | 350 mg |
| Xanthan Gum | 85 mg |
| Alginate | 65 mg |
| Magnesium Stearate | 7 mg |
| Metformin | 66 mg |
| Total | 573 mg |

TABLE 8C

VFB Capsule Composition with Sitagliptin

| Ingredient | Amount |
|---|---|
| Glucomannan | 350 mg |
| Xanthan Gum | 85 mg |
| Alginate | 65 mg |
| Magnesium Stearate | 7 mg |
| Sitagliptin | 3 mg |
| Total | 510 mg |

TABLE 8D

VFB Capsule Composition with Metformin and Sitagliptin

| Ingredient | Amount |
|---|---|
| Glucomannan | 350 mg |
| Xanthan Gum | 85 mg |
| Alginate | 65 mg |
| Magnesium Stearate | 7 mg |
| Metformin | 66 mg |
| Sitagliptin | 3 mg |
| Total | 576 mg |

EXAMPLE 5

This Example describes the preparation of soft gelatin (softgel) capsules containing a composition comprising Viscous Fiber Blend/Complex mixed with medium chain triglycerides.

Methods

Preparation of a soft gelatin capsule containing Viscous Fiber Blend:

Inner Filling

A soft gelatin capsule was prepared with an inner filling including Viscous Fiber Blend/Complex (konjac/xanthan/alginate (70:13:17)) and an oil (e.g., medium chain triglycerides (MCT) at a ratio of from 0.01:99.99 up to 80:20 (w/w VFB/C:MCT). An example of a ratio of VFB/C:MCT of 52.7:47.3 w/w is shown below in TABLE 9. The MCT can be substituted with any of the following oils: soy bean oil, palm kernel oil, fish oil, and canola oil.

TABLE 9

Exemplary Inner Filling Ingredients for Capsules

| Capsule weight (inner filling) | VFB/C (konjac/xanthan/alginate (70:13:17)) | Medium chain triglycerides (MCT) |
|---|---|---|
| 100 mg | 52.7 mg | 47.3 mg |
| 1500 mg | 790 mg | 710 mg |
| 2,500 mg | 1320 mg | 1180 mg |

Outer Capsule Shell

The outer capsule shell includes a mixture of gelatin, glycerin, and water.

An exemplary softgel capsule was produced as follows:

Inner Filling:
790 mg VFB/C
710 mg MCT

Outer Capsule Shell:
2,130 mg of a mixture consisting of gelatin, glycerin and water was used.

The proportion of outer capsule shell to inner filling may be varied to accommodate various capsule sizes, as shown in TABLE 9.

The softgel capsule containing VFB/C mixed with medium chain triglycerides is effective to delay the VFB/C viscous effects in water, while allowing for maximum viscosity of the VFB/C under gastric conditions, as demonstrated in EXAMPLE 6.

EXAMPLE 6

This Example demonstrates that VFB/C encapsulated in an oil-based softgel capsule is effective to delay its viscous effects in water in order to reduce potential choking hazard, while at the same time quickly reaching maximum viscosity under gastric conditions.

Methods:

The viscosity profile of VFB/C encapsulated in an oil-based softgel capsule was compared in distilled water and gastric juice.

Soft gelatin capsules containing VFB/C mixed with oil were prepared as described in EXAMPLE 5. Each capsule contained 790 mg VFB/C (konjac/xanthan/alginate (70:13:17)). Six capsules (a total of 4.74 g VFB/C) were dissolved in a total volume of either 331.8 distilled $H_2O$ or gastric juice (prepared according to USP guidelines) for a 5 g VFB/C:350 g $H_2O$ ratio.

The samples were placed in the liquid medium in a vessel placed in a 25° C. water bath. After 15 minutes in liquid, the softened capsules were broken open using a spoon. The mixture was then mixed manually for 5 minutes, then put into a blender and mixed mechanically at 4,000 rpm for 30 seconds, followed by mixing at 8,000 rpm for an additional 30 seconds. Viscosity readings were taken at time intervals over a 3-hour period.

Results:

The viscosity profile of VFB/C softgel capsules in distilled water is shown below in TABLE 10.

TABLE 10

Viscosity Profile of VFB/C (Konjac/Xanthan/Alginate (70:13:17)) Plus oil (710 mg MCT) Encapsulated in a Softgel Outer Capsule (2,130 mg of a Mixture Consisting of Gelatin, Glycerin, and water) as Measured in Distilled Water

| Time (a) (minutes elapsed after capsules were added to water) | Time (b) (minutes elapsed after capsules were blended in water) | Spindle: R3 viscosity (centipoise) | RPM |
|---|---|---|---|
| 25 | 5 | 3500 | 10 |
| 48 | 28 | 9350 | 5 |
| 63 | 43 | 19630 | 2.5 |
| 80 | 60 | 39660 | 1 |
| 108 | 88 | 48350 | 1 |
| 139 | 119 | 60180 | 1 |
| 180 | 160 | 63590 | 1 |

The viscosity profile of VFB/C softgel capsules in gastric juice is shown below in TABLE 11.

TABLE 11

Viscosity Profile of VFB/C (Konjac/Xanthan/Alginate (70:13:17)) Plus Oil (710 Mg MCT) Encapsulated in a Softgel Outer Capsule (2130 Mg of a Mixture Consisting of Gelatin, Glycerin, and Water) as Measured in Gastric Juice

| Time (a) (minutes elapsed after capsules were added to gastric juice) | Time (b) (minutes elapsed after capsules were blended in gastric juice) | Spindle: R3 Viscosity (centipoise) | RPM |
|---|---|---|---|
| 25 | 5 | >90000 | 1 |

TABLE 12

Comparison of Viscosity of VFB/C Softgel Capsules in Water and Gastric Juice

| Time (b) (minutes elapsed after capsules were blended (minutes) | Viscosity in Water | Viscosity in Gastric Juice |
|---|---|---|
| 5 | 3,500 | >90000 |
| 28 | 9350 | |
| 43 | 19630 | |
| 60 | 39660 | |
| 88 | 48350 | |
| 119 | 60180 | |
| 160 | 65590 | |

As shown in TABLES 11-12, under gastric conditions, the oil-based VFB/C delivered in softgel capsules thickened quickly (within 5 minutes) after blending, reaching a viscosity of greater than 90,000 centipoise. In contrast, as shown in TABLES 10 and 12, the oil-based VFB/C delivered in softgel capsules thickened slowly in distilled water, resulting in a viscosity level of 3,500 at five minutes after blending and gradually increasing to a maximum of 65,000 centipoise at 160 minutes after blending. As shown in TABLE 10, the VFB/C delivered in softgel capsules took 60 minutes to reach a viscosity of 19,630 cps in distilled water and it did not reach 90,000 cps even after over 3 hours. This result is significantly different from the behavior observed for VFB (non-granulated, without oil-based capsule) when stirred into water, which reached 90,000 cps at 120 minutes, as shown in EXAMPLE 1, TABLE 4 herein. In fact, it is noted that the time delay observed in reaching maximum viscosity for VFB/C delivered in softgel capsules is even more pronounced than that observed for granulated VFB mesh size 40 and mesh size 60, each of which reached 90,000 cps at 120 minutes (see TABLE 4 herein). These results indicate that the addition of oil to VFB/C is effective to delay its viscous effects when mixed with water. Therefore, the combination of VFB/C with oil may be used in order to avoid a potential choking hazard during administration of VFB/C to an individual, since it has been observed that VFB/C alone becomes viscous very quickly in water and could form large clumps.

Moreover, in contrast to the delayed viscosity observed in water, the VFB/C delivered in softgel capsules reached 90,000 cps within 5 minutes after contact with gastric conditions, as shown in TABLES 11 and 12. This high viscosity was maintained over time (data not shown). It was surprising that the combination of VFB/C with oil could reach 90,000 cps within such a short time under gastric conditions. It is important to note that this viscosity profile for VFB/C in softgel capsules was very different from that observed with VFB alone under gastric conditions (shown in TABLE 4 herein), which was not observed to reach such high viscosities even after 60 minutes. As shown in TABLE 4, VFB alone only reached 6500 cps after 30 minutes.

Therefore, the results described in this example that were observed with VFB in softgel capsules, including the delay in viscosity in water, and the rapid high viscosity level reached under gastric conditions, demonstrate that the combination of VFB/C and oil may be used to produce the desired effect of a feeling of fullness in the stomach and reduce the sensation of hunger in an individual while reducing the risk of choking during ingestion.

While not wishing to be bound by theory, the beneficial results described in this example for the combination of VFB/C and oil may be due to the coating of oil over the fiber. With regard to the delayed viscosity observed in water, it is likely that the oil coats and separates the particles such that water does not cause the particles to clump together and limit their dispersion. However, under gastric conditions, the acidity and gastric enzymes would likely strip off at least a portion of the oil coating such that VFB/C fibers could quickly reach maximum viscosity. Moreover, in contrast to dispersion of VFB/C (without oil coating) in water, which yields some clumping, the combination of VFB/C with oil avoids the clumping in water, which leads to lower initial overall viscosity in water, and thereby allows for an eventual higher viscosity over time because of the ability of the VFB/C and oil combination to disperse more evenly to allow more fiber particles to react with water instead of forming clumps.

EXAMPLE 7

This Example demonstrates the effects of PGX and sitagliptin (JANUVIA) in the Zucker FA/FA Rat Model Background/Rationale This study was designed to determine the effects of PGX and sitagliptin, alone or in combination, compared to controls (cellulose and vehicle, respectively), on measures of metabolic disease and disease mechanism (glycemic control, peptide hormones, enzyme activity, histology and histopathology) in the rat model Zucker FA/FA. The ZDF/Crl-Lepr$^{fa/fa}$ rat is considered to be an excellent model of adult-onset obesity with comorbid type II diabetes (C. Daubioul et al., *J. Nutr.* 132:967-973 (2002); J. M. Lenhard et al., *Biochem. & Biophys. Res. Comm.* 324:92-97 (2004); J. N. Wilson, *Atheriosclerosis* 4:147-153 (1984)). ZDFs are mutants that were found to lack brain leptin receptors. Leptin is a protein secreted by adipose tissue that signals appetite suppression. Therefore, in these mutant rats, there is no feedback signaling to reduce appetite or to induce satiety. ZDF rats consume food at very high rates and become obese very rapidly. This model therefore mimics people who are obese through overeating. As the ZDF rats become obese, they rapidly become insensitive to insulin, just as seen in man (also referred to as metabolic syndrome). The ZDF rats are also hyperlipidemic, showing this rat model to be a good model for metabolic syndrome in humans. Over time, the diabetes progresses in the ZDF model, similar to the progression in humans, with loss of pancreatic β cell (insulin secreting cells) population. Proteins become glycosolated by the excess glucose, causing problems in both ZDFs and man with organ function, particularly in the kidneys. High glucose levels cause glycosylation of proteins, causing diabetic nephropathy and vascular damage.

The standard marker of the degree of glucose damage to proteins is glycosylated hemoglobin (HbA1c), which is elevated in ZDFs. Measurement of albumin in the urine is also a standard marker of diabetic injury to the kidney. The FDA guidelines for treatment of diabetes require glycemic control and reduction of tissue damage caused by high glucose.

Methods and Materials

Test Materials

A granulated dietary fiber composition of the invention, referred to herein as PGX, was prepared as described in Example 1. PGX was incorporated into a basic rat chow (D11725) at 5% wt/wt by Research Diets, New Brunswick, N.J. Cellulose fiber was incorporated into a basic rat chow (D11725) at 5% wt/wt as a control.

Sitagliptin was purchased as prescription JANUVIA tablets (60 tablets at 100 mg strength). Sitagliptin dosing solutions were prepared by homogenizing JANUVIA tablets in distilled water and separating particulate matter by centrifugation. Sitagliptin dosing solutions were prepared fresh weekly. Following formulation, sitagliptin was refrigerated.

Quality Control

Before the beginning of the dosing studies, dosing solutions were analyzed. Using JANUVIA as a reference, a well-homogenized sample of fresh dosing solution was analyzed to verify concentration. Samples from the top, middle and bottom of a container of dosing solution were analyzed to verify homogeneity. A well-homogenized sample of 10 day old dosing solution was also analyzed to verify stability.

During the study, an aliquot of each preparation of dosing solution was stored at −80° C. After the conclusion of the study, these stored samples were analyzed to verify the concentration of the test article.

Study Design

Animals 44 young adult (9 week old) male rats (Zucker ZDF/Crl-Lepr$^{fa/fa}$), were obtained from Charles River Laboratories, Kingston, N.Y. The rats weighed an average of 250-350 grams upon test initiation. The rats were housed in cages which conformed to size standards in Guide for the Care and Use of Laboratory Animals (Nat'l Res. Council, 1996). Bedding was changed at least twice per week. The animals were maintained at a temperature range of 18-22° C., humidity 44-68%, and a photoperiod of 12 hour light/dark cycle. The rats were acclimated for 4 days prior to the start of the study. Each animal was given a sequential number and was uniquely identified with a stainless steel ear tag or other appropriate, permanent method. Morbidity and mortality checks were carried out twice daily during the study.

The animals were randomly assigned to one of four groups: (1) Control 5% cellulose fiber/chow [C]; (2) 5% PGX/chow [PGX]; (3) C+sitagliptin (10 mg/kg/day); and (4) PGX+sitagliptin (10 mg/kg/day).

Test Diets

Diets containing 45% fat and either 5% cellulose (w:w) or 5% PGX (w:w) (based on Research Diets formula D12451) were available ad libitum, except for the fasted tests. Filtered tap water was available ad libitum. The test diets were nearly isoenergetic (PGX diet provided 3.98 kcal/g and cellulose diet provided 3.90 kcal/g).

Sitagliptin was prepared in water and given daily by gavage (10 mg/kg as the base in a volume of 10 mL/kg). Sitagliptin was administered in the morning, with samples and data collected after treatment.

Study Phases

The study was divided into an acclimation phase (the days from delivery to first dose; referred to as week 0); a test article administration phase (six full weeks, numbered 1-6 in TABLE 13 below); and a final takedown phase (week 7). TABLE 13 shows the measurements that were carried out during the various phases of the study.

TABLE 13

Study Phases and Measurements

| Week | Phase | Regular Measures | Single Measures |
|---|---|---|---|
| 0 | acclimation | body weight | HbA1c (optional) |
| 1 | test article | body weight; food consumption; fed/fasted glucose testing | none |
| 2 | test article | body weight; food consumption; fed/fasted glucose testing | none |
| 3 | test article | body weight; food consumption; fed/fasted glucose testing | HbA1c (optional) |
| 4 | test article | body weight; food consumption; fed/fasted glucose testing | none |
| 5 | test article | body weight; food consumption; fed/fasted glucose testing | none |
| 6 | test article | body weight; food consumption; fed/fasted glucose testing | HbA1c (optional); oral glucose tolerance test |
| 7 | takedown | body weight; food consumption | glucose-loaded peptide analysis; fasted peptide analysis; lipid analysis; clinical chemistry; necropsy |

Note:
At the sponsor's discretion, rats were monitored for additional time during the test article administration phase. This monitoring included body weight, food consumption, and fed/fasted blood glucose testing.

After acclimation, rats were allocated to treatment groups according to weight (in a stratified random fashion).

TABLE 14

Study Groups

| Group | Fiber (diet) | Gavage |
|---|---|---|
| 1 (control) | Cellulose | Vehicle (Water) |
| 2 (PGX alone) | PGX | Vehicle (Water) |
| 3 (JANUVIA alone) | Cellulose | 10 mg/kg/day sitagliptin |
| 4 (combination) | PGX | 10 mg/kg/day sitagliptin |

Regular Study Measures

Rats were weighed once each week, as shown in TABLE 13. Food was weighed three times per week, and spillage was determined twice per week. These values were used to determine daily average food consumption for each week following acclimation. Glucose concentrations were determined using a hand-held glucose meter (e.g., Bayer Asencia Elite). Blood was collected via tail nick following sitagliptin administration; one sample was collected when food was available for the previous 24 hours (non-fasted), and one sample was collected on another day when food was not available overnight (16 h fasted).

Oral Glucose Tolerance Test (OGTT)

A fasted (16 h) OGTT was conducted after sitagliptin administration. After baseline samples were collected, glucose was administered by gavage (1 g/kg, PO). Blood samples were collected via tail nick at 10, 20, 30, 60, and 120 minutes after glucose administration. Blood glucose concentrations were determined using a hand-held glucose meter. The remainder of the sample was allowed to clot, and centrifuged to separate serum. Serum samples were frozen for insulin analysis.

Glucose-Loaded Peptide Analysis

Rats were fasted overnight and given their regular sitagliptin treatment in the morning. After baseline samples were collected, glucose was administered by gavage (2 g/kg, PO). Blood samples (target volume: 160 µl, for at least 70 µl plasma) were collected via tail nick at 15, 30, 60, and 90 minutes after glucose administration. Peptidase inhibitors (diprotin A, AEBSF and Sigma protease inhibitor cocktail, to final concentrations of 34 µg/ml, 1 mg/ml and 1% v:v, respectively) were used. Plasma was separated by centrifugation and frozen for peptide analysis.

Lipid Determinations, Plasma DPPIV Activity and Clinical Chemistry

A blood sample was collected via retroorbital bleed (under isoflurane anesthesia) during the takedown phase. A portion of this sample was tested for lipid concentrations (total, LDL, and HDL cholesterol and triglycerides) using an analyzer (e.g., Polymer Technology Systems CardioChek PA). Plasma was separated by centrifugation and flash-frozen for DPPIV activity determination. The remainder was prepared for comprehensive clinical chemistry analysis.

Necropsy

Rats were fasted overnight and given their regular sitagliptin treatment in the morning. Following the in-life procedures, rats were anesthetized with isoflurane, and a blood sample was collected via cardiac puncture. No peptidase inhibitors were used. Following sample collection, a limited necropsy was performed. A section of ileum (approximately one inch, collected one inch rostral to the cecum) was rinsed in chilled saline and flash frozen; this sample was analyzed for DPPIV mRNA. One kidney was flash-frozen for DPPIV mRNA analysis; one liver lobe was flash frozen for DPPIV activity and mRNA analysis. The pancreas (collected as a pancreatic pluck, with associated tissue including the remainder of the intestine), one liver lobe and one kidney were post-fixed for staining with hematoxylin and eosin. One liver lobe was snap-frozen for staining with Sudan Black.

The tissue samples were forwarded to Histo-Scientific Research Laboratories Inc. (Mount Jackson, Va.) for histological processing and for pathological evaluation by a board-certified pathologist. The pathology analysis was based on the gross and microscopic evaluation of the liver (two lobes), right kidney and pancreas from 39 male rats.

Hemoglobin Glycosylation Measurements

The extent of hemoglobin glycosylation was determined using a clinical analyzer (e.g., Bayer DCA2000). Blood samples for analysis were collected via tail nick.

Statistical Methods

All data are presented as mean±SEM. Data was analyzed by an appropriate analysis of variance method. A two-way ANOVA was used to determine the main effect of diet (PGX versus cellulose) and drug (sitagliptin versus vehicle), and their interaction. When a significant interaction effect was identified, a one-way ANOVA with Tukey's multiple comparison posthoc test was used to identify differences between groups. For parameters where repeated measurements were taken over time (i.e., body weight, glucose, HbA1c, and satiety hormones), a two-way repeated measure ANOVA was performed with between subject factor (treatment of 4 levels) and within subject factor (time). Non-interval data (e.g. histology scores) were analyzed by Kruskal Wallis test and Dunn's MCT. Significance was set at $P<0.05$.

Results

Body Weight, Body Composition and Food Consumption

Figure 4:
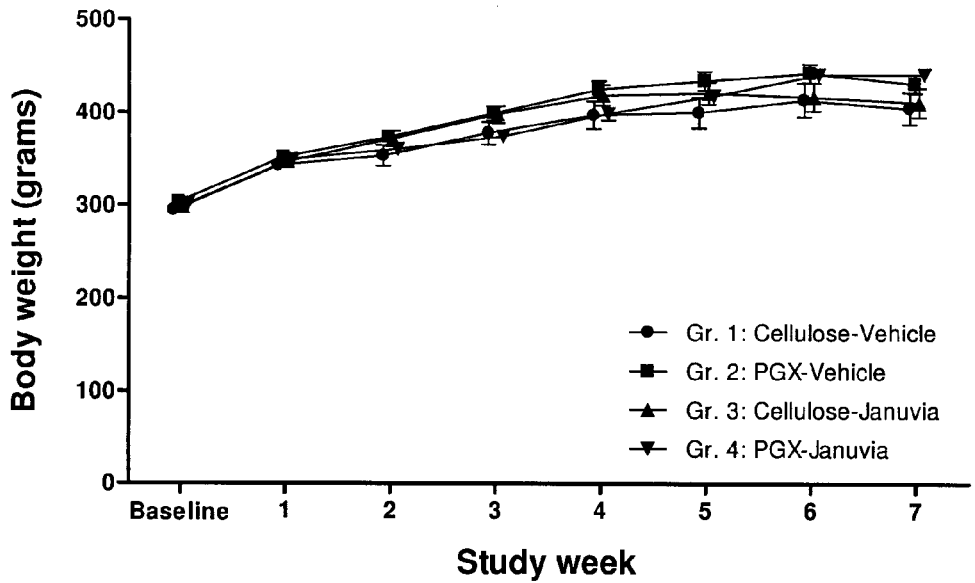
FIG. 4 graphically illustrates the body weight (grams) of the rats in Groups 1-4 measured weekly over the course of the 7 week comparison study comparing the effects of PGX and sitagliptin in the Zucker FA/FA Rat Model, as described in EXAMPLE 7.

FIG. 4 graphically illustrates the body weight (grams) of the rats in Groups 1-4 measured weekly over the course of the 7 week study. All groups gained weight over the course of the study. However, groups fed PGX-containing diet (5% w:w) tended to gain more weight, whether treated with JANUVIA (gavage, 10 mg/kg qd) or vehicle). Group 3 (cellulose control diet with JANUVIA gavage) initially tended to gain more weight than the vehicle-treated group, but ended the study with body weights similar to vehicle-treated rats.

samples). The primary endpoints were fat mass, lean mass and bone mineral density. Tissue composition (i.e., % body fat) and fat free mass were also reported, but the information on these measurements was redundant with other measures.

Figure 5:
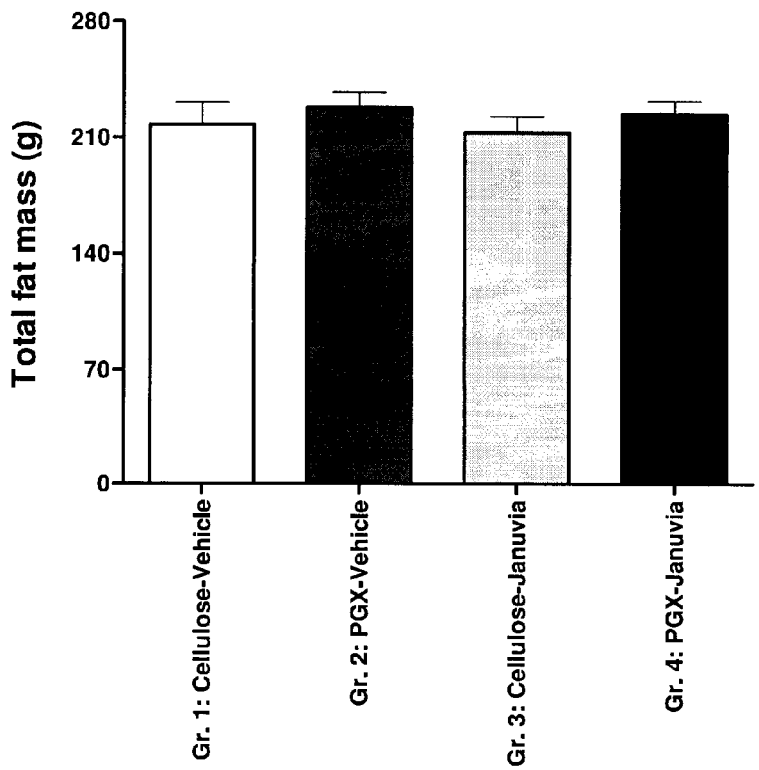
FIG. 5 graphically illustrates the total fat mass (grams) of the rats in Groups 1-4 as measured at week seven of the study, as described in EXAMPLE 7.

FIG. 5 graphically illustrates the total fat mass (grams) of the rats in Groups 1-4 as measured at week seven of the study. As shown in FIG. 5, fat mass tended to be slightly higher in the groups with higher final body weights (Group 2: PGX-vehicle and Group 4: PGX-JANUVIA). However, this did not reach statistical significance.

Figure 6:
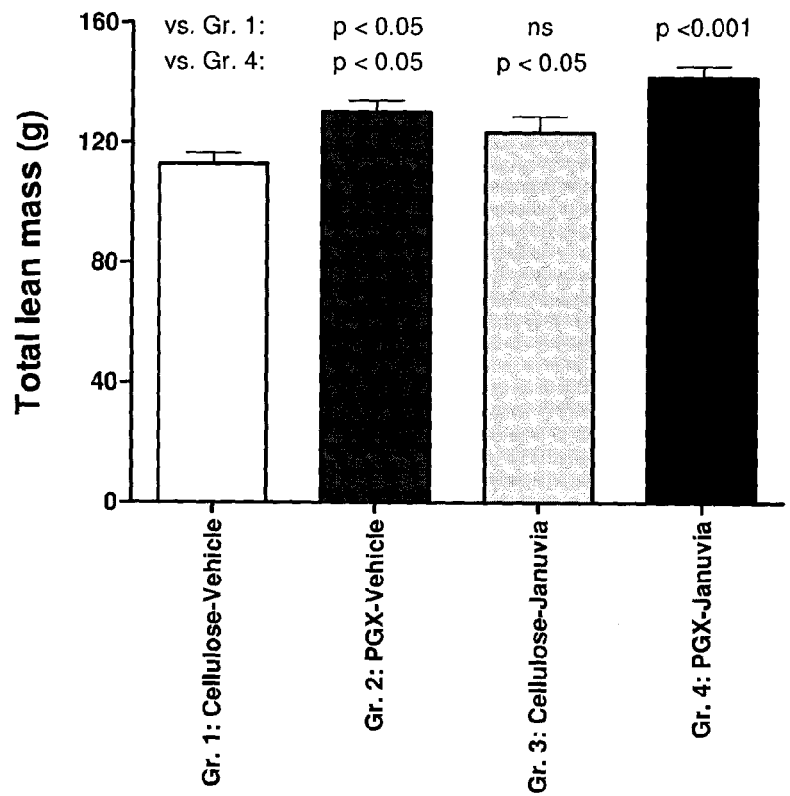
FIG. 6 graphically illustrates the total lean tissue mass (grams) of the rats in Groups 1-4 as measured at week seven of the study, as described in EXAMPLE 7.

FIG. 6 graphically illustrates the total lean tissue mass (grams) of the rats in Groups 1-4 as measured at week seven of the study. As shown in FIG. 6, lean mass differed substantially, with groups that were heavier at week seven showing greater lean mass (compare FIG. 4 with FIG. 6). Advanced diabetes is often associated with cachexia, including loss of lean body mass. The present results are consistent with a reduction of cachexia. The differences in lean tissue mass reached statistical significance ($F(3,38)=7.97$, $p<0.0005$).

Post hoc testing with Group 1 (Cellulose-vehicle) as a reference group showed a significant effect of PGX alone (Group 1 vs. Group 2, PGX-vehicle, $p<0.05$). All post hoc tests were calculated using Newman-Keuls multiple comparison test, unless otherwise indicated. However, JANUVIA alone did not show an effect on lean body mass (Group 1 vs. Group 3: Cellulose-JANUVIA, $p>0.05$). The effect of the combination of PGX and JANUVIA differed from Group 1 and from the effect of either treatment alone (Group 1 vs. Group 4: PGX-JANUVIA, $p<0.001$; Group 4 vs. Groups 2 and 3, both $p<0.05$).

The bone mineral density did not differ between groups (data not shown).

As further shown in TABLE 18, tissue composition (% body fat) did not differ significantly between the groups. The lack of a difference in body composition despite clear differences in lean mass is likely due to the extremely high fat mass in a Zucker rat of this age (compare values in FIG. 5 with those in FIG. 6).

TABLE 15

Body Weight/Composition and Food Consumption

|  | Group 1: Cellulose-Vehicle | Group 2: PGX-Vehicle | Group 3: Cellulose-JANUVIA | Group 4: PGX-JANUVIA |
|---|---|---|---|---|
| Baseline body weight (g) | 294.5 ± 4.4 | 303.0 ± 5.1 | 297.9 ± 3.7 | 301.5 ± 2.2 |
| Week 7 body weight (g) | 404.9 ± 17.4 | 431 ± 9.6 | 411.0 ± 16.1 | 440.8 ± 5.3 |
| Tissue composition (% fat) | 65.6 ± 1.4 | 63.5 ± 1.3 | 63.3 ± 0.9 | 61.1 ± 1.3 |
| Fat free mass (g) | 122.6 ± 3.5 | 140.0 ± 3.8 | 133.0 ± 5.6 | 151.6 ± 4.1 |
| Mean food consumption (g/day) | 26.2 ± 0.5 | 20.3 ± 0.6 | 22.9 ± 0.7 | 18.4 ± 0.5 |

Baseline body weights did not differ significantly between groups ($F(3,43)=0.91$, $p\sim0.45$; all F ratios were calculated using one-way analysis of variance). In absolute terms, all body weights were similar, as shown above in TABLE 15. Although Week 7 body weights tended to differ between groups, these differences did not reach statistical significance.

Body composition was measured using dual-energy X-ray absorptiometry (DEXA) of the carcasses at the end of the study (i.e., after a limited necropsy for histopathology As further shown in TABLE 15, fat-free mass, a composite of lean mass and bone mineral mass, differed significantly between groups ($F(3,38)=7.66$, $p<0.001$). As this parameter is predominantly composed of lean mass, it shows a similar pattern of results (compare values in TABLE 15 with FIG. 6).

Figure 7:
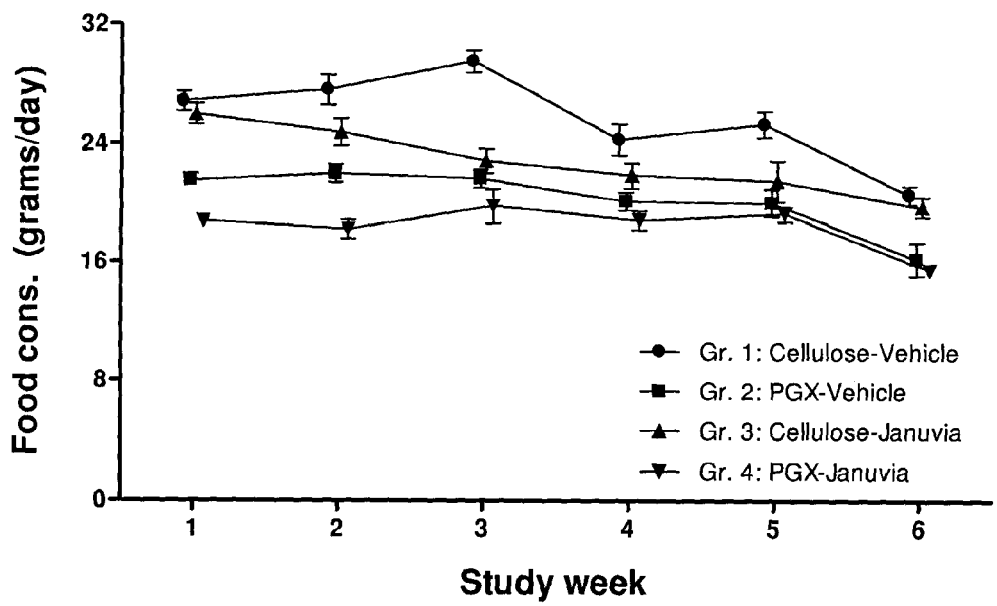
FIG. 7 graphically illustrates the food consumption (grams/day) of the rats in Groups 1-4 measured weekly over the course of the 7 week study, as described in EXAMPLE 7.

FIG. 7 graphically illustrates the food consumption (grams/day) of the rats in Groups 1-4 measured weekly over the course of the 7 week study. As shown in FIG. 7, Groups fed the PGX-containing diet tended to eat less than groups fed the cellulose-containing diet, and groups treated with JANUVIA tended to eat less than groups treated with vehicle.

For analysis, food consumption values were averaged for each rat, as shown in TABLE 15. Statistically significant differences were observed in food consumption between all groups. Groups 2, 3, and 4 all differed significantly from Group 1 (all p<0.001). The effect of the combination of PGX and JANUVIA differed from the effect of either treatment alone (Group 2 vs. Group 4, p<0.05; Group 3 vs. Group 4, p<0.001).

Glucose Homeostatis-Continuing Measures

Figure 8:
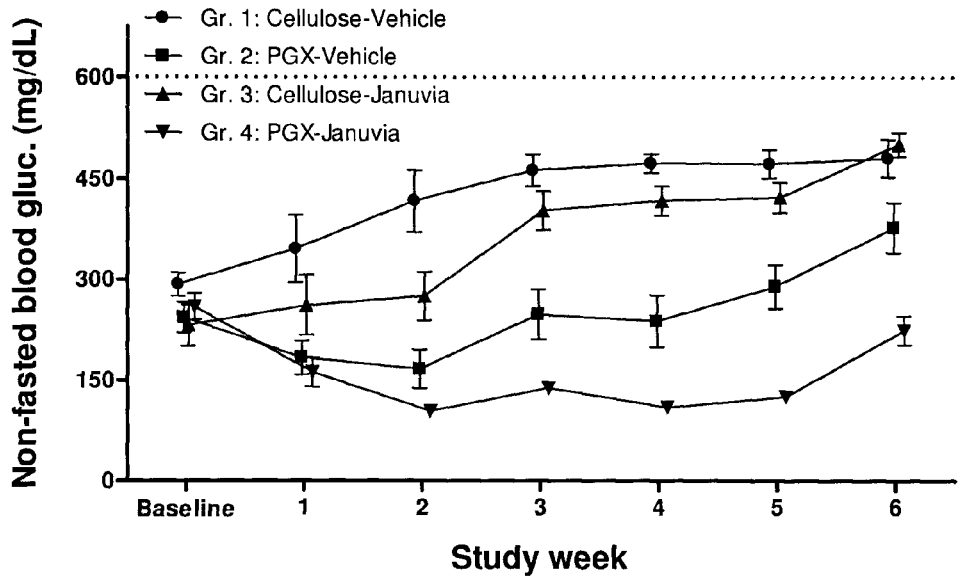
FIG. 8 graphically illustrates the level of non-fasted blood glucose (mg/dL) of the rats in Groups 1-4 measured at weekly intervals over the course of the 7 week study, as described in EXAMPLE 7.

FIG. 8 graphically illustrates the level of non-fasted blood glucose (mg/dL) of the rats in Groups 1-4 measured at weekly intervals over the course of the 7 week study. As shown in FIG. 8, non-fasted blood glucose, as measured at weekly intervals, showed clear differences between groups. Group 1 (cellulose-vehicle) showed increasing blood glucose concentrations. In contrast, Group 4 (PGX-JANUVIA) showed an initial, sustained decrease in blood glucose concentrations, with a slight rise in the last week that measurements were taken (Week 6). Group 2 (PGX-vehicle) and Group 3 (cellulose-JANUVIA) showed an intermediate pattern of results.

A statistical analysis of blood glucose concentrations was conducted using the data from baseline and the last measurement, as was done for body weight. The results are shown below in TABLE 16.

Figure 9:
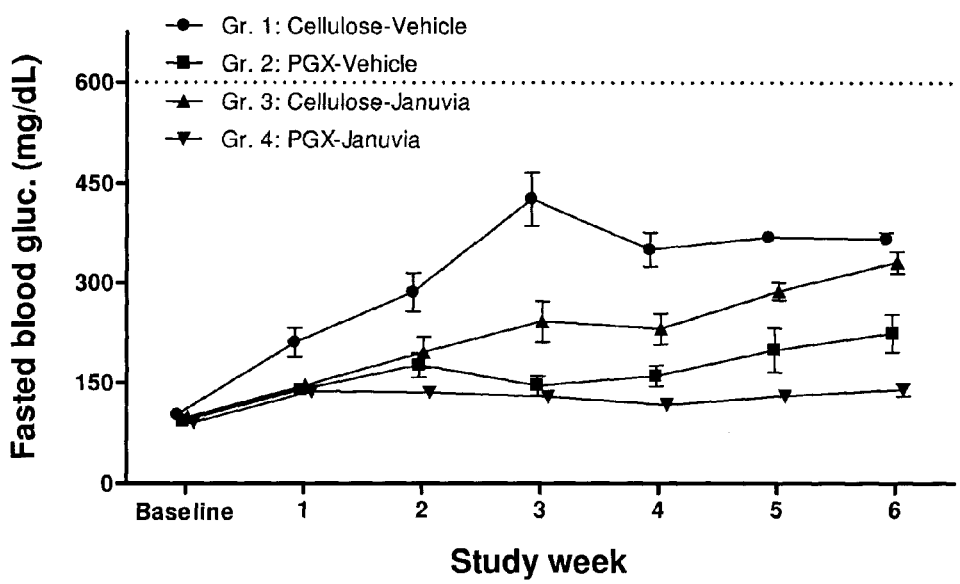
FIG. 9 graphically illustrates the level of fasted blood glucose (mg/dL) of the rats in Groups 1-4 measured at weekly intervals over the course of the 7 week study, as described in EXAMPLE 7.

FIG. 9 graphically illustrates the level of fasted blood glucose (mg/dL) of the rats in Groups 1-4 measured at weekly intervals over the course of the 7 week study. As shown in FIG. 9, blood glucose levels were lower than those observed in non-fasted conditions, and did not decrease for any group; otherwise the group trends were similar (compare FIG. 8 and FIG. 9).

As shown in TABLE 16 and FIG. 9, week 6 fasted blood glucose concentrations differed significantly between groups (F(3,38)29.03, p<0.0001). Compared to Group 1 (cellulose-vehicle), Group 3 (cellulose-JANUVIA) did not differ significantly. However, Group 2 (PGX-vehicle, p<0.05) and Group 4 (PGX-JANUVIA, p<0.001) did differ significantly. The effect of the combination of PGX and JANUVIA differed from the effect of either treatment alone (Group 4 vs. Group 2, p<0.01; Group 4 vs. Group 3, p<0.001).

Figure 10:
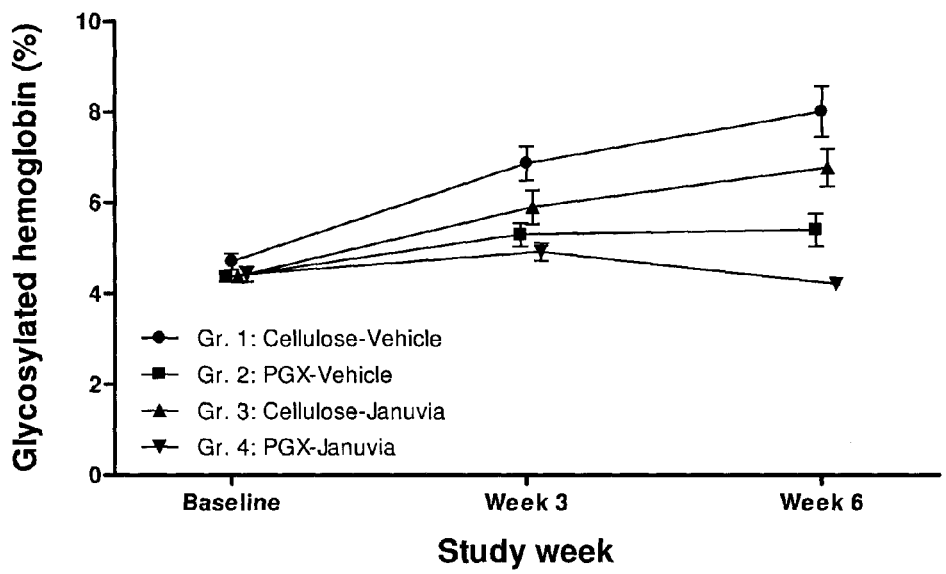
FIG. 10 graphically illustrates the amount (%) of glycosylated hemoglobin in blood samples obtained from the rats in Groups 1-4, as determined at baseline, week 3 and week 6 of the study, as described in EXAMPLE 7.

FIG. 10 graphically illustrates the amount (%) of glycosylated hemoglobin in blood samples obtained from the rats in Groups 1-4, as determined at baseline, week 3 and week 6 of the study. As shown in FIG. 10 and TABLE 19, baseline measurements of hemoglobin glycosylation did not differ significantly between the groups. However, as further shown in TABLE 16 and FIG. 10, hemoglobin glycosylation increased over the course of the study, a result that is consistent with observations of increasing blood glucose concentrations under both fasting and non-fasting conditions. As measured at week 6, hemoglobin glycosylation differed significantly between the groups, as shown in

TABLE 16

| Glucose Homeostasis - continuing measures | | | | | |
|---|---|---|---|---|---|
| | | Group 1: Cellulose-Vehicle | Group 2: PGX-Vehicle | Group 3: Cellulose-JANUVIA | Group 4: PGX-JANUVIA |
| Non-fasted blood glucose (mg/dL) | Baseline | 292.8 ± 17.7 | 243.2 ± 22.9 | 231.8 ± 31.2 | 259.7 ± 20.0 |
| | Week 6 | 480.5 ± 27.9 | 377.1 ± 37.0 | 500.9 ± 17.4 | 224.0 ± 21.8 |
| 16 h fasted blood glucose (mg/dL) | Baseline | 101.9 ± 6.7 | 93.0 ± 4.6 | 98.4 ± 5.4 | 90.6 ± 2.8 |
| | Week 6 | 366.5 ± 9.7 | 224.5 ± 28.4 | 331.1 ± 16.4 | 139.8 ± 9.9 |
| Hemoglobin glycosylation (%) | Baseline | 4.7 ± 0.2 | 4.4 ± 0.1 | 4.4 ± 0.1 | 4.4 ± 0.2 |
| | Week 6 | 8.0 ± 0.6 | 5.4 ± 0.4 | 6.8 ± 0.4 | 4.2 ± 0.1 |

As shown above in TABLE 16, baseline non-fasted blood glucose concentrations did not differ significantly between the groups. However, as further shown in TABLE 16, the week 6 non-fasted blood glucose concentrations did differ significantly between the groups (F(3,38)=20.83, p<0.0001). Compared to Group 1 (cellulose-vehicle), Group 3 (cellulose-JANUVIA) did not differ significantly; however, Group 2 (PGX-vehicle, p<0.05) and Group 4 (PGX-JANUVIA, p<0.001) did differ significantly. The combination of PGX and JANUVIA had a statistically significant effect in lowering blood glucose levels when compared to effect of either treatment alone (Group 4 vs. Group 2 or Group 3, p<0.001).

Fasted blood glucose (food withdrawn the previous night, about 16 h before blood sampling) was also measured at weekly intervals throughout the study. As shown in TABLE 16, baseline fasted blood glucose concentrations did not differ significantly between groups. However, clear differences between groups were apparent in the fasted blood glucose concentrations measured at week 6.

TABLE 16 and FIG. 10 (F(3,34)=21.12, p<0.0001). Compared to Group 1 (cellulose-vehicle), all groups showed significantly lower degrees of hemoglobin glycosylation (Group 2: PGX-vehicle, p<0.001; Group 3: cellulose-JANUVIA, p<0.05; Group 4: PGX-JANUVIA, p<0.001). The effect of the combination of PGX and JANUVIA differed from the effect of either treatment alone (Group 2 vs. Group 4, p<0.05; Group 3 vs. Group 4, p<0.001).

Glucose Homeostasis: Oral Glucose Tolerance Test (OGTT) Measures

Figure 11:
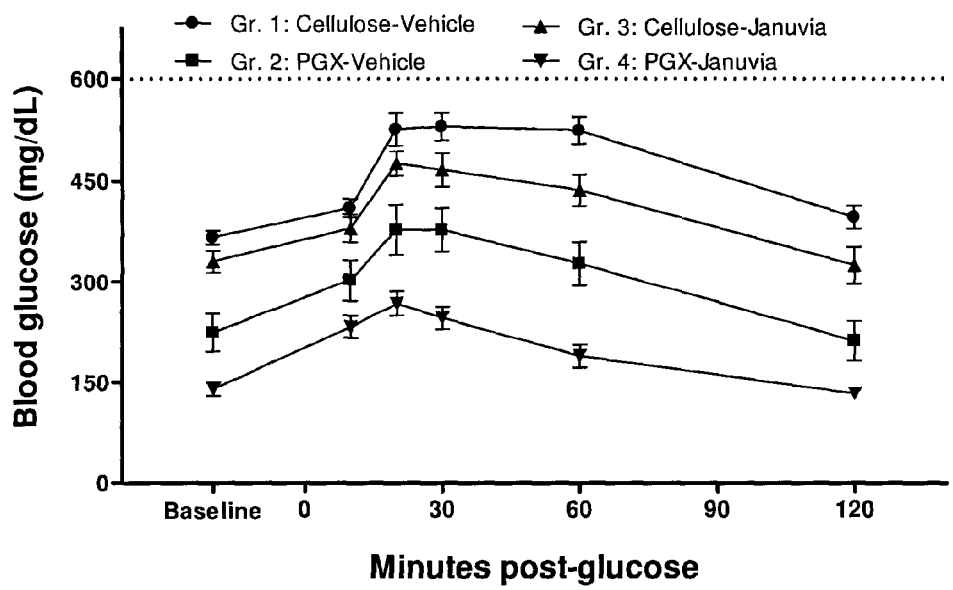
FIG. 11 graphically illustrates the level of blood glucose (mg/dL) measured over a two hour time period post-glucose in a 16 hour fasted oral glucose tolerance test carried out in the rats in Groups 1-4, as described in EXAMPLE 7.

In an oral glucose tolerance test run under overnight fasted conditions at week 6, there were substantial differences observed between groups throughout the observation period, as shown in FIG. 11 and TABLE 17. FIG. 11 graphically illustrates the level of blood glucose (mg/dL) measured over a two hour time period post-glucose in a 16 hour fasted oral glucose tolerance test carried out in the rats in Groups 1-4. TABLE 20 provides the measurements of the OGTT test.

TABLE 17

Glucose Homeostatis-OGTT measures

|  |  | Group 1: Cellulose-Vehicle | Group 2: PGX-Vehicle | Group 3: Cellulose-JANUVIA | Group 4: PGX-JANUVIA |
|---|---|---|---|---|---|
| Blood glucose | Baseline (μg/dL) | 366.5 ± 9.7 | 224.5 ± 28.4 | 331.1 ± 16.4 | 139.8 ± 9.9 |
|  | AUC(0-120) (μg * h/dL, baseline-subt) | 13928 ± 1501 | 9650 ± 1053 | 9201 ± 1090 | 6369 ± 1090 |
| Serum insulin | Baseline (ng/mL) | 4.3 ± 0.8 | 8.4 ± 1.2 | 6.6 ± 1.1 | 8.4 ± 0.8 |
|  | AUC(0-120) (ng * h/dL, baseline-subt) | −57.3 ± 28.4 | 61.9 ± 53.7 | −3.0 ± 22.7 | 121.7 ± 52.4 |

As shown in FIG. 11 and TABLE 17, in an oral glucose tolerance test run under overnight fasted conditions at week 6 of the study, there were substantial differences between the groups throughout the observation period. The baseline blood glucose measurements were discussed above. Data collected following glucose administration were analyzed by integrating the area under the curve for the time course (AUC). AUC differed significantly between the groups as shown in TABLE 17 ($F(3,38)=5.62$, $p<0.005$). However, the only statistically significant post hoc comparison was the difference between Group 1 (cellulose-vehicle) and Group 4 (PGX-JANUVIA, $p<0.01$; all others $p>0.05$).

Figure 12:
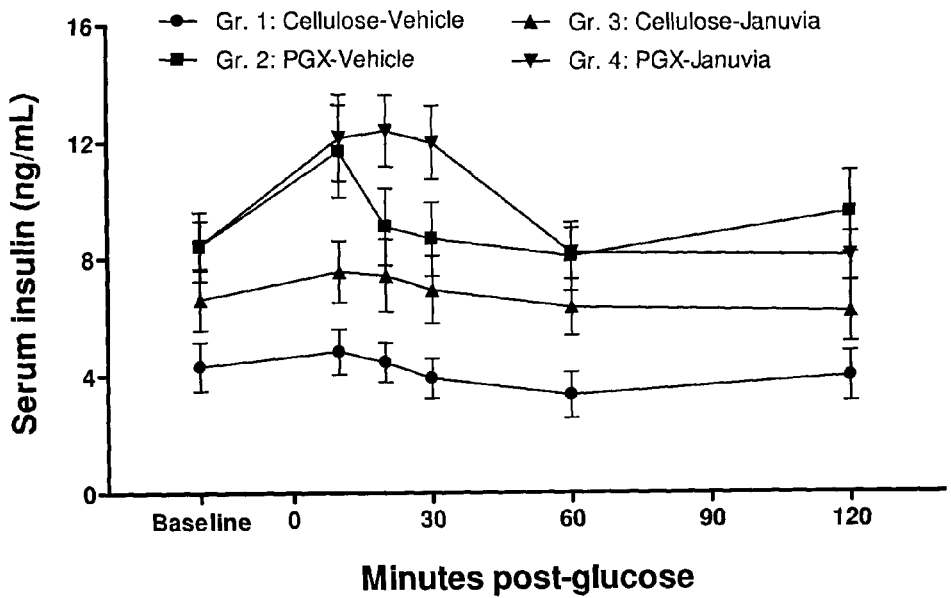
FIG. 12 graphically illustrates the serum insulin concentration (ng/mL) in blood samples obtained over a 2 hour period post-glucose administration in rats from Groups 1-4 after a 16-hour fasted OGTT test at week 6 of the study, as described in EXAMPLE 7.

FIG. 12 graphically illustrates the serum insulin concentration (ng/mL) in blood samples obtained over a 2 hour period post-glucose administration in rats from Groups 1-4 after a 16 hour fasted OGTT test at week 6 of the study. As shown in FIG. 12, serum insulin, measured from the same samples analyzed in FIG. 11, also showed clear differences between the groups. Insulin concentrations differed at baseline, as shown in TABLE 17 ($F(3,38)=3.44$, $p<0.05$). Compared to Group 1 (cellulose-Vehicle), groups fed PGX-containing diets (Group 2: PGX-vehicle and Group 4: PGX-JANUVIA) both showed an increase in serum insulin, resulting in positive AUCs, however, only Group 4 (PGX-JANUVIA) showed a sustained increase in insulin concentrations, as shown in FIG. 12.

Lipid Analysis

Figure 13:
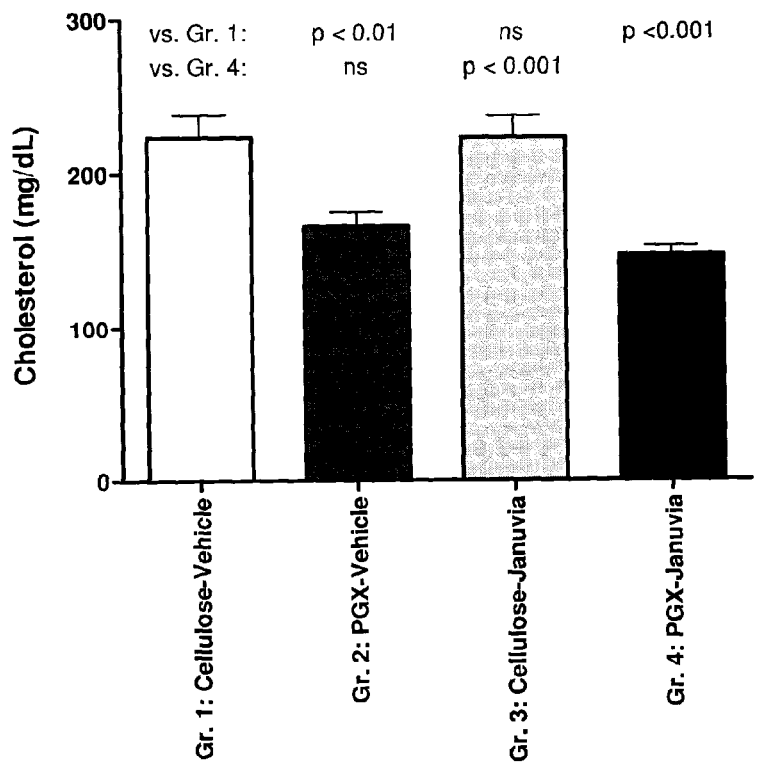
FIG. 13 graphically illustrates the total cholesterol measured in the blood samples obtained from the rats from Groups 1-4 at week 7, as described in EXAMPLE 7.

The lipid content of a terminal blood sample from each rat was analyzed at week seven. FIG. 13 graphically illustrates the total cholesterol measured in the blood samples obtained from the rats from Groups 1-4 at week 7. As shown in FIG. 13, total cholesterol differed significantly by group ($F(3,38)=13.47$, $p<0.0001$). Compared to Group 1 (cellulose-vehicle), both Group 2 (PGX-vehicle) and Group 4 (PGX-JANUVIA) showed lower blood cholesterol ($p<0.01$ and $p<0.001$, respectively). Treatment with JANUVIA alone was not effective to lower blood cholesterol (Group 1 vs. Group 3, $p>0.05$).

Clinical Chemistry

A terminal blood sample from each rat at week seven was analyzed for clinical chemistry parameters. The results are shown below in TABLE 18.

TABLE 18

Clinical Chemistry

|  | Group 1: Cellulose-Vehicle | Group 2: PGX-Vehicle | Group 3: Cellulose-JANUVIA | Group 4: PGX-JANUVIA | Reference Range |
|---|---|---|---|---|---|
| Creatine kinase (IU/L) | 98.8 ± 25.6 | 71.6 ± 7.8 | 76.3 ± 12.8 | 88.8 ± 6.6 | not available |
| Calcium (mg/dL) | 11.0 ± 0.2 | 11.6 ± 0.2 | 11.2 ± 0.2 | 11.4 ± 0.1 | 6 to 10.6 |
| Phosphorus (mg/dL) | 6.2 ± 0.1 | 6.3 ± 0.3 | 6.0 ± 0.2 | 6.3 ± 0.1 | 5.9 to 8.3 |
| Potassium (mEq/L) | 91.3 ± 1.3 | 94.1 ± 0.8 | 92.8 ± 0.5 | 97.7 ± 1.0 | 79 to 111 |

JANUVIA) had significantly higher baseline insulin concentrations ($p<0.05$). Although Group 3 (cellulose-JANUVIA) tended to have higher baseline insulin concentrations than Group 1, this difference did not reach statistical significance ($p>0.05$).

Insulin AUC values tended to differ between groups, as shown in TABLE 20, although the overall effect was statistically marginal ($F(3,38)=2.85$, $p=0.052$). As further shown in FIG. 12 and TABLE 17, serum insulin concentrations initially rose (peaking at 10 minutes post-glucose), but then decreased below baseline in Group 1 (cellulose-vehicle). AUC values for Group 3 (cellulose-JANUVIA) remained near baseline, resulting in an AUC of approximately zero (see TABLE 17). Groups 2 (PGX-vehicle) and 4 (PGX- As shown in TABLE 18, serum creatine kinase activity did not differ significantly between the groups. Serum calcium concentrations were above the reference range, although it is noted that the reference range was established with non-obese Sprague Dawley rats. Serum calcium did not differ significantly by group. Serum chloride differed significantly between groups, with Group 4 having the highest concentration, followed by Group 2 ($F(3,34)=8.79$, $p<0.0005$) (data not shown). However, the implications of this result are unclear, as all group means were within the reference range. Serum potassium concentrations were below the reference range (see TABLE 18), although they are physiologically normal, and the groups did not differ significantly. All group average sodium concentrations were below the reference range, and differed significantly between groups (F(3,34)=8.68, p<0.0005), with Group 4 having the highest concentration, followed by Group 2 (data not shown).

Target Organ Effects

A summary of microscopic findings is provided below in TABLE 19.

TABLE 19

Summary of Histopathology Findings

| Tissue/Finding | Group Average Score or Percent | | | | Group Incidence | | | |
|---|---|---|---|---|---|---|---|---|
| | 1 | 2 | 3 | 4 | 1 | 2 | 3 | 4 |
| LIVER | | | | | | | | |
| vacuolation, hepatocytes, microvesicular | 3.1 | 2.5 | 2.6 | 1.8 | 8/8 | 11/11 | 9/9 | 11/11 |
| vacuolation, hepatocytes, macrovesicular | 0.9 | 0.8 | 0.9 | 0.9 | 7/8 | 9/11 | 7/9 | 10/11 |
| Sudan black positive hepatocytes | 3.1 | 2.5 | 2.8 | 1.8 | 8/8 | 11/11 | 9/9 | 11/11 |
| Cystic hepatocytes degeneration with fibrosis | 0.0 | 0.0 | 0.1 | 0.0 | 0/8 | 0/11 | 1/9 | 0/11 |
| hepatic focal infarction | 0.3 | 0.0 | 0.2 | 0.0 | 1/8 | 0/11 | 1/9 | 0/11 |
| KIDNEY | | | | | | | | |
| mesangial expansion | 2.3 | 1.4 | 2.1 | 1.2 | 8/8 | 10/11 | 9/9 | 9/11 |
| dilatation, tubules | 3.0 | 2.1 | 2.8 | 1.3 | 8/8 | 11/11 | 9/9 | 10/11 |
| degeneration/regeneration, tubules | 2.5 | 1.6 | 2.3 | 0.7 | 8/8 | 11/11 | 9/9 | 8/11 |
| dilation, renal pelvis | 2.0 | 1.9 | 2.3 | 1.9 | 6/8 | 10/11 | 9/9 | 8/10 |
| mineralization, renal pelvis | 0.1 | 0.2 | 0.2 | 0.1 | 1/8 | 2/11 | 2/9 | 1/10 |
| inflammation, renal pelvis | 0.0 | 0.0 | 0.8 | 0.1 | 0/8 | 0/11 | 2/9 | 1/10 |
| PANCREAS | | | | | | | | |
| hypertrophy, islets | 3.1 | 3.9 | 3.8 | 3.1 | 8/8 | 11/11 | 9/9 | 11/11 |
| mononuclear cell infiltrate, islets | 1.0 | 1.0 | 1.0 | 0.7 | 8/8 | 11/11 | 9/9 | 8/11 |
| islet cell degeneration | 1.6 | 1.1 | 1.4 | 0.8 | 8/8 | 11/11 | 9/9 | 9/11 |
| fibrosis, islets | 2.0 | 1.3 | 2.1 | 1.5 | 8/8 | 11/11 | 9/9 | 11/11 |
| hemorrhage/hemosiderin, islets | 1.1 | 1.0 | 1.1 | 1.4 | 8/8 | 11/11 | 9/9 | 11/11 |
| percent of islet area containing positive insulin positive cells | 39 | 47 | 40 | 53 | NA | NA | NA | NA |

NA = Not applicable
Severity Scores: 0 = within normal limits; 1 = minimal; 2 = mild; 3 = moderate; 4 = marked; 5 = severe Pancreas Overview: The pancreas demonstrated the following changes: islet hypertrophy, mononuclear cell infiltrates within islets, islet cell degeneration, islet fibrosis, and islet hemosiderin/hemorrhage. Islet hypertrophy was present in all animals regardless of treatment, but the amount of hypertrophy was higher in animals treated with PGX alone (Group 2) and JANUVIA alone (Group 3) as compared to Group 1 (control) and Group 4 (PGX and JANUVIA). While groups 2 and 3 had the greatest amount of hypertrophy, the percent of islet area containing insulin-positive cells was highest in the Group 4 animals. The severity of islet cell degeneration and islet fibrosis was reduced in the animals treated with PGX alone (Group 2) and with the combination of PGX and JANUVIA (Group 4) as compared with the control group (Group 1) and JANUVIA alone (Group 3). The incidence and severity of mononuclear cell infiltrates was reduced in the combination group (Group 4) as compared to the other groups, while the severity of hemorrhage/hemosiderin was slightly increased in this same group.

Figure 14:
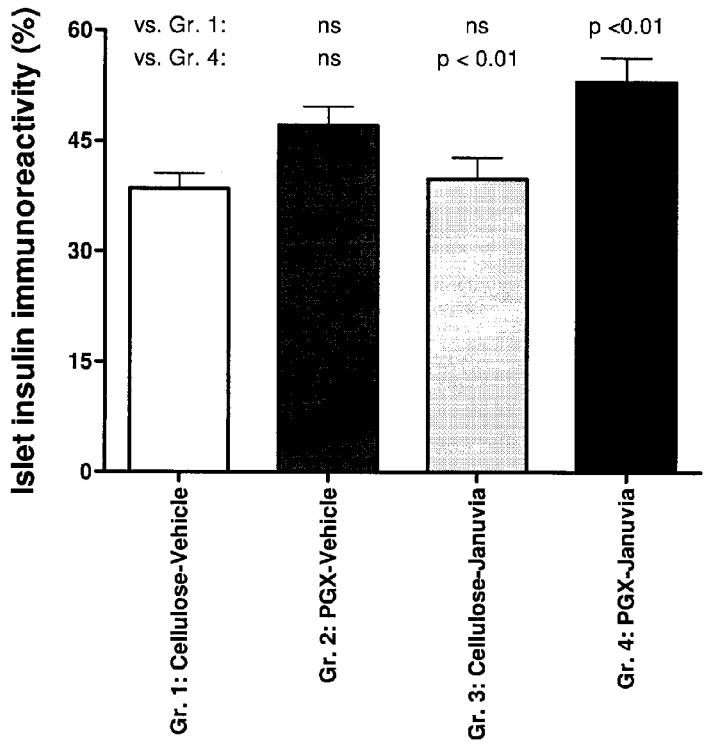
FIG. 14 graphically illustrates the beta cell mass, measured as islet insulin immunoreactivity (%) in the rats from Groups 1-4 at week seven (during necropsy) of the study, as described in EXAMPLE 7.

FIG. 14 graphically illustrates the beta cell mass, measured as islet insulin immunoreactivity (%) in the rats from Groups 1-4 at week seven (during necropsy) of the study. As shown in FIG. 14, pancreatic beta cell mass varied as a function of treatment (F(3,37)=5.70, p<0.005). Rats fed the PGX-containing diet tended to have a greater insulin-immunoreactive area than rats fed the cellulose-containing diet. While JANUVIA by itself did not change the insulin-immunoreactive area, it tended to increase the effect of PGX (Group 1: cellulose-vehicle vs. Group 2: PGX-vehicle or Group 3: cellulose-JANUVIA, p>0.05); Group 1 vs. Group 4: PGX-JANUVIA, p<0.01; Group 4 vs. Group 2, p>0.05; Group 4 vs. Group 3, p<0.01).

Figure 15:
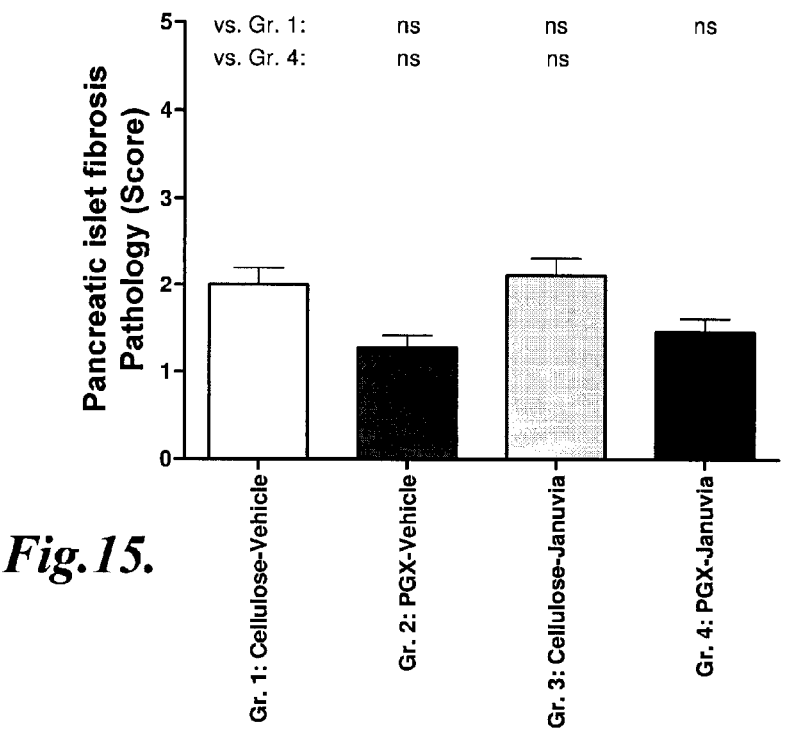
FIG. 15 graphically illustrates the pancreatic islet fibrosis pathology scores on a scale of 0 (pathology absent) to 5 (severe pathology) using tissue sections stained with hematoxylin and eosin from rats in Groups 1-4 at week seven (during necropsy) of the study, as described in EXAMPLE 7.

FIG. 15 graphically illustrates the pancreatic islet fibrosis pathology scores on a scale of 0 (pathology absent) to 5 (severe pathology) using tissue sections stained with hematoxylin and eosin from rats in Groups 1-4 at week seven (during necropsy) of the study. As shown in FIG. 15, pancreatic islet fibrosis was generally minimal or mild (1 or 2). Group scores differed significantly (K(4)=12.62, p<0.01, Kruskal-Wallis test). While the only group difference that reached statistical significance in post hoc testing was the difference between Group 2 (PGX-vehicle) and Group 3 (Cellulose-JANUVIA), which showed an increased severity as compared to the control, PGX tended to decrease the severity of fibrosis, both alone, and in combination with JANUVIA.

As shown in TABLE 22, pancreatic hemorrhage and deposits of hemosiderin were generally minimal, and did not vary by treatment (K(4)=5.75, p~0.12, Kruskal-Wallis).

Figure 16:
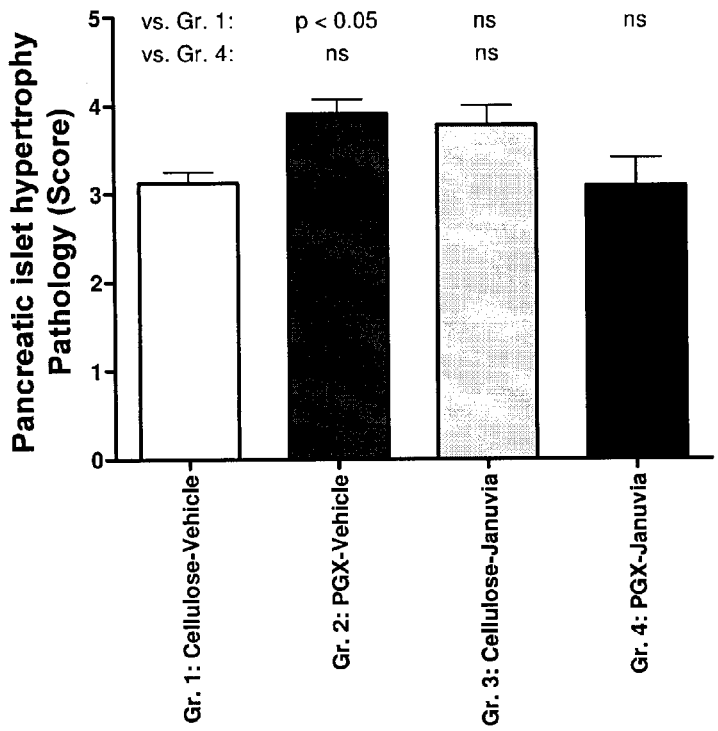
FIG. 16 graphically illustrates the pancreatic islet hypertrophy pathology scores on a scale of 0 (pathology absent) to 5 (severe pathology) using tissue sections from rats in Groups 1-4 at week seven (during necropsy) of the study, as described in EXAMPLE 7.

FIG. 16 graphically illustrates the pancreatic islet hypertrophy pathology scores on a scale of 0 (pathology absent) to 5 (severe pathology) using tissue sections from rats in Groups 1-4 at week seven (during necropsy) of the study. As shown in FIG. 16, pancreatic islet hypertrophy, measured as a histopathology score, was generally moderate (3) to marked (4). Pathology scores differed significantly between groups (K(4)=9.47, p<0.05; Kruskal-Willis). However, while Group 2 and Group 3 tended to have higher scores than Group 1 (both p>0.05, Dunn's test), Group 4 had scores comparable to Group 1 (p>0.05, Dunn's test).

Figure 17:
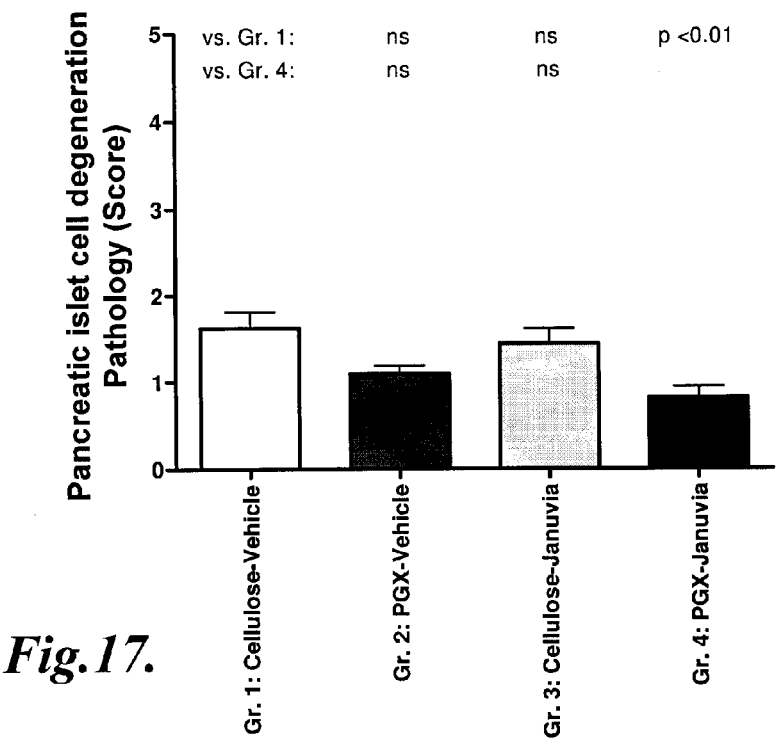
FIG. 17 graphically illustrates the pancreatic islet cell degeneration pathology scores on a scale of 0 (pathology absent) to 5 (severe pathology) using tissue sections from rats in Groups 1-4 at week seven (during necropsy) of the study, as described in EXAMPLE 7.

FIG. 17 graphically illustrates the pancreatic islet cell degeneration pathology scores on a scale of 0 (pathology absent) to 5 (severe pathology) using tissue sections from rats in Groups 1-4 at week seven (during necropsy) of the study. As shown in FIG. 17, the pathology scores for pancreatic islet cell degeneration tended to parallel the differences seen in beta cell mass (compare FIG. 17 with FIG. 14). JANUVIA alone produced little or no decrease in pathology (Group 1 vs. Group 3, p>0.05). PGX alone produced a trend toward a decrease, but without statistical significance (Group 1 v. Group 2, p>0.05). However, the combination of PGX and JANUVIA produced a statistically significant decrease in pancreatic islet cell degeneration (Group 1 vs. Group 4, p<0.01).

As shown above in TABLE 19, pancreatic islet mononuclear cell infiltration was generally scored as minimal. Although a statistically significant main effect of treatment was observed (K(4)=8.06, p<0.05; Kruskal-Wallis), no significant group differences were seen in post hoc testing (all p>0.05, Dunn's test).

Kidney:

Overview: In the kidney, there were a variety of changes, some of which were affected by treatment. Within glomeruli, there was increased mesangial matrix (mesangial expansion). This glomerular change was lowest in severity in the animals treated with a combination of PGX and JANUVIA (Group 4), followed closely by the animals treated with PGX alone (Group 2). Groups 1 (control) and 3 (JANUVIA alone) had comparable severities of these changes. Tubular changes included tubular dilatation and tubular degeneration and regeneration. Again, the lowest average scores for both parameters were seen in Group 4 (combination group). While the incidence of these changes was 100% for Groups 1, 2 and 3, the incidence in Group 4 animals was 10/11 and 8/11 for dilatation and degeneration/regeneration, respectively. Group 2 (PGX alone) also had lower scores for both parameters as compared to Groups 1 and 3. Renal pelvis dilatation was observed in all treatment groups generally with comparable incidence and severity except for Group 3. This treatment group had a slightly higher incidence and severity of renal pelvic dilatation. Renal pelvis dilatation (hydronephrosis) has been reported in both lean and obese Zucker rats. Marsh et al., "Cardiovascular dysfunction in Zucker obese and Zucker diabetic fatty rats: role of hydronephrosis," *Am J Physiol Heart Circ Physiol* 293(1):H292-8 (2007).

Figure 18:
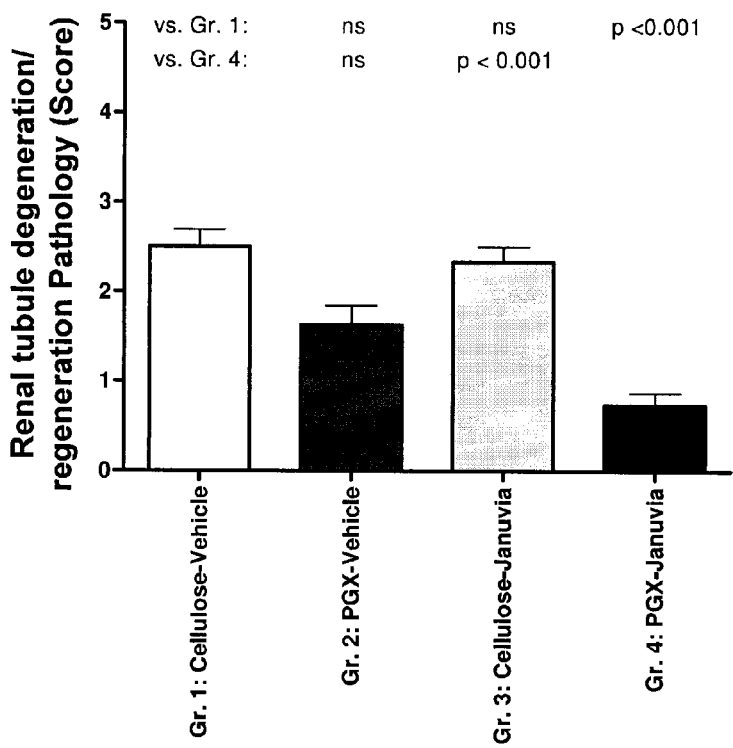
FIG. 18 graphically illustrates the renal tubule degeneration/regeneration pathology scores on a scale of 0 (pathology absent) to 5 (severe pathology) using tissue sections from rats in Groups 1-4 at week seven (during necropsy) of the study, as described in EXAMPLE 7.

FIG. 18 graphically illustrates the renal tubule degeneration/regeneration pathology scores on a scale of 0 (pathology absent) to 5 (severe pathology) using tissue sections from rats in Groups 1-4 at week seven (during necropsy) of the study. As shown in FIG. 18, renal tubule degeneration/regeneration scores generally varied from minimal (1) to mild (2). Group scores varied with treatment (K(4)=25.40, p<0.0001). PGX-containing diet alone tended to reduce pathology, but the difference did not reach statistical significance. While JANUVIA alone did not reduce pathology (Group 1 vs. Group 3), the combination of JANUVIA with PGX produced an effect that neither treatment alone produced (Group 1 vs. Group 4, PGX-JANUVIA, p<0.001, Dunn's test). This effect tended to be greater than the effect of PGX alone, and was significantly greater than the effect of JANUVIA alone (Group 2 vs. Group 4, p>0.05; Group 3 vs. Group 4, p<0.001, both by Dunn's test).

Figure 19:
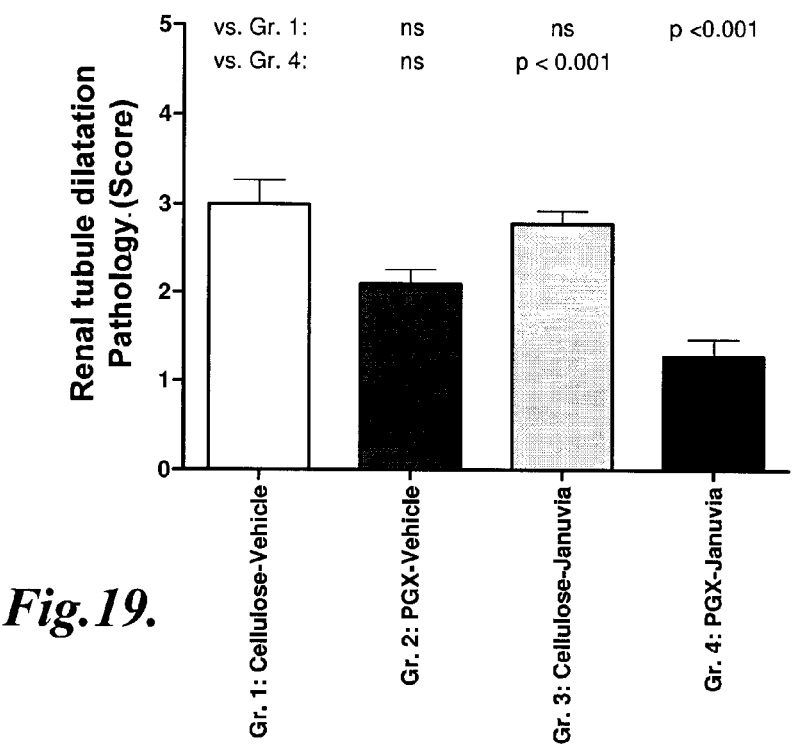
FIG. 19 graphically illustrates the renal tubule dilatation pathology scores on a scale of 0 (pathology absent) to 5 (severe pathology) using tissue sections from rats in Groups 1-4 at week seven (during necropsy) of the study, as described in EXAMPLE 7.

FIG. 19 graphically illustrates the renal tubule dilatation pathology scores on a scale of 0 (pathology absent) to 5 (severe pathology) using tissue sections from rats in Groups 1-4 at week seven (during necropsy) of the study. As shown in FIG. 19, renal tubule dilatation scores followed a pattern similar to tubule degeneration/regeneration scores (compare FIG. 19 with FIG. 18). Group scores varied with treatment (K(4)=22.89, p<0.0001). PGX-containing diet alone tended to reduce pathology, but the difference did not reach statistical significance (Group 1, Cellulose-vehicle vs. Group 2, PGX-vehicle, p>0.05, Dunn's test). While JANUVIA alone did not reduce pathology (Group 1 vs. Group 3, Cellulose-JANUVIA, p>0.05, Dunn's test), the combination of JANUVIA with PGX produced an effect that neither treatment alone produced (Group 1 vs. Group 4, PGX-JANUVIA, p<0.001, Dunn's test). This effect tended to be greater than the effect of PGX alone, and was significantly greater than the effect of JANUVIA alone (Group 2 vs. Group 4, p>0.05; Group 3 vs. Group 4, p<0.001, both by Dunn's test).

Figure 20:
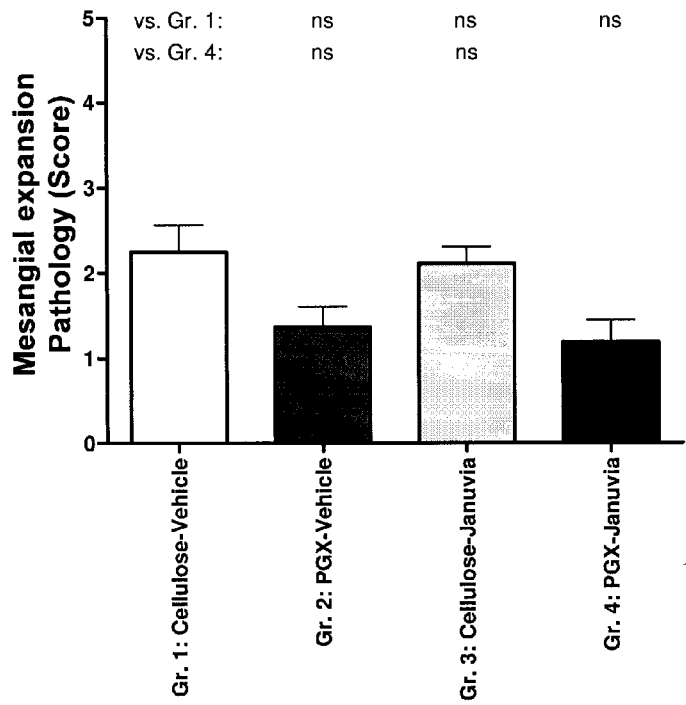
FIG. 20 graphically illustrates the mesangial expansion pathology scores on a scale of 0 (pathology absent) to 5 (severe pathology) using tissue sections from rats in Groups 1-4 at week seven (during necropsy) of the study, as described in EXAMPLE 7.

FIG. 20 graphically illustrates the mesangial expansion pathology scores on a scale of 0 (pathology absent) to 5 (severe pathology) using tissue sections from rats in Groups 1-4 at week seven (during necropsy) of the study. As shown in FIG. 20, mesangial expansion scores followed a pattern similar to tubule degeneration/regeneration scores (compare FIG. 20 with FIG. 18). However, despite a statistically significant main effect (K(4)=10.92, p<0.05), no group differences reached statistical significance on post hoc testing (all p>0.05; Dunn's test).

Figure 21:
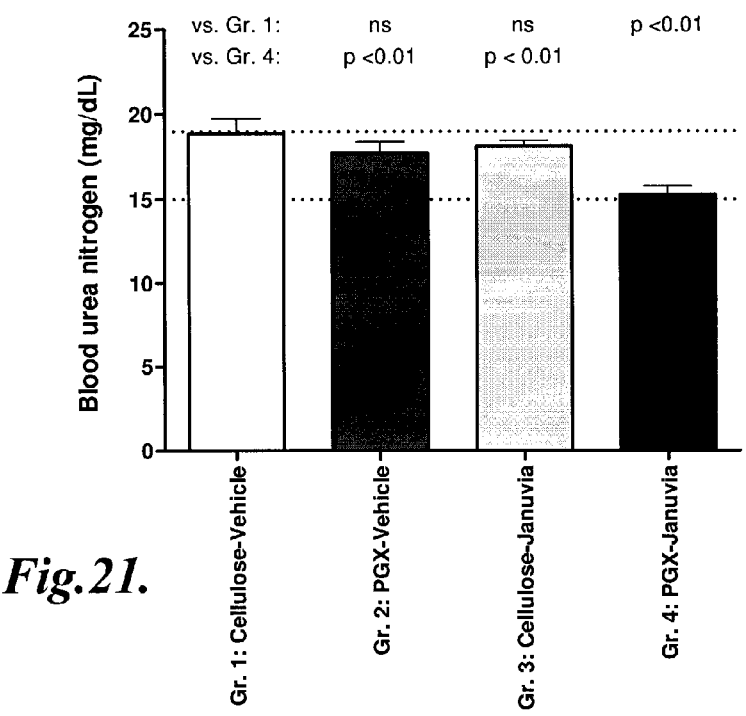
FIG. 21 graphically illustrates the blood urea nitrogen (BUN) levels (mg/dL) measured from a terminal blood sample obtained from rats in Groups 1-4 at week seven of the study, as described in EXAMPLE 7.

FIG. 21 graphically illustrates the blood urea nitrogen (BUN) levels (mg/dL) measured from a terminal blood sample obtained from rats in Groups 1-4 at week seven of the study. As shown in FIG. 21, blood urea nitrogen was generally within a reference range established for Sprague-Dawley rats (shown in dotted lines in FIG. 21). However, groups differed significantly (F(3,38)=6.53, p<0.005). PGX alone and JANUVIA alone tended to decrease BUN, but the effect did not reach statistical significance (Group 1 vs. Group 2 and Group 1 vs. Group 3, p>0.05). In contrast, the combination of PGX and JANUVIA decreased BUN significantly (Group 1 vs. Group 4, p<0.01). In addition, the effect of the combination differed from either PGX or JANUVIA alone (Group 4 vs. Group 2 and Group 4 vs. Group 3, both p<0.01).

As shown above in TABLE 19, renal pelvis dilatation was generally scored as mild, and scores did not differ significantly between groups. As further shown in TABLE 19, scores for pelvis inflammation were generally 0 (within normal limits) or 1 (minimal), and did not vary significantly between groups. Scores for renal pelvis mineralization were also generally within normal limits and did not vary between groups (see TABLE 19). Serum creatinine, measured from a terminal blood sample, was generally low, as shown in TABLE 19, and did not differ significantly between groups.

Liver

In the liver, all treatment groups displayed microvesicular and macrovesicular hepatocyte vacuolation. These vacuoles were Sudan black positive consistent with the presence of lipid (hepatic lipidosis). All animals displayed microvesicular hepatocyte vacuolation. However, the severity of this change was reduced in the Group 4 animals as compared to the other treatment groups, and slightly reduced in Groups 2 and 3 as compared to Group 1. Macrovesicular hepatocyte vacuolation was not severe, and while present in all treatment groups, was not observed in all animals. The large vacuoles seen in macrovesicular vacuolation, are considered to likely be the result of fusion of small (microvesicular) vacuoles. There was no noticeable difference in the incidence or severity of macrovesicular vacuolation between any of the treatment groups. The reduced severity of Sudan Black positive hepatocytes in the Group 4 animals, as compared to the other treatment groups, was attributable to the reduction in microvesicular vacuolation. Other observations, consistent with changes seen in animals with hepatic lipidosis of moderate to severe severity, included the following: areas of infarction in one animal in Group 1 (mild in severity) and one animal in Group 3 (mild in severity); and minimal cystic hepatocyte degeneration in one animal in Group 3.

Figure 22:
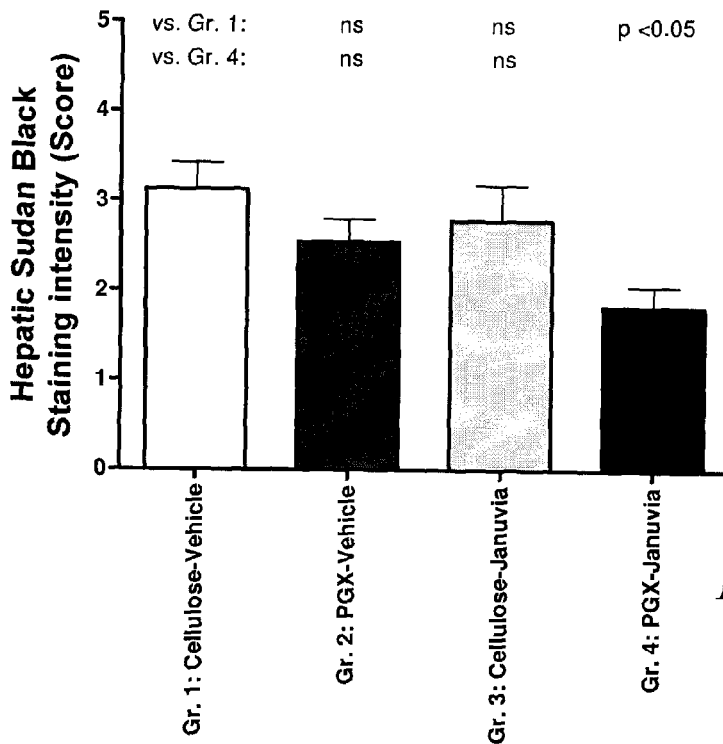
FIG. 22 graphically illustrates the staining intensity of Sudan Black staining on a scale of 0 (no staining) to 5 (intense staining) using liver tissue sections from rats in Groups 1-4 at week seven (during necropsy) of the study, as described in EXAMPLE 7.

FIG. 22 graphically illustrates the staining intensity of Sudan Black staining on a scale of 0 (no staining) to 5 (intense staining) using liver tissue sections from rats in Groups 1-4 at week seven (during necropsy) of the study. Sudan Black staining of vacuoles indicates the presence of lipid in these vacuoles (hepatic lipidosis). As shown in FIG. 22, treatment produced statistically significant changes in staining scores (K(4)=9.33, p<0.05). Both PGX and JANUVIA tended to reduce the severity of steatosis, but the effect did not reach statistical significance. However, the combination produced a statistically significant reduction (Group 1 vs. Group 4, PGX-JANUVIA, p<0.05, Dunn's test).

Figure 23:
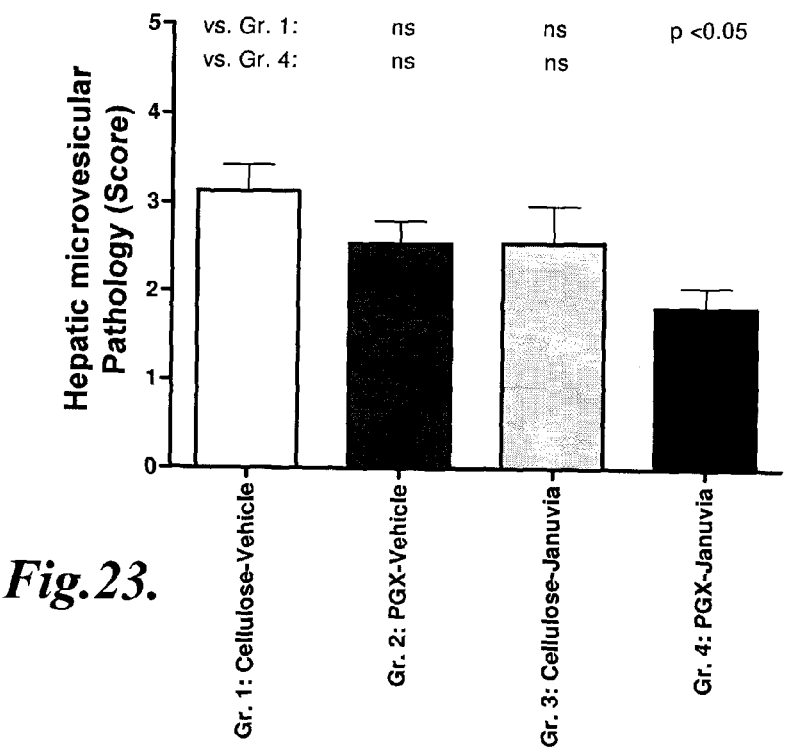
FIG. 23 graphically illustrates the hepatic vacuolation (microvesicular) pathology scores on a scale of 0 (pathology absent) to 5 (severe pathology) using tissue sections from rats in Groups 1-4 at week seven (during necropsy) of the study, as described in EXAMPLE 7.

FIG. 23 graphically illustrates the hepatic vacuolation (microvesicular) pathology scores on a scale of 0 (pathology absent) to 5 (severe pathology) using tissue sections from rats in Groups 1-4 at week seven (during necropsy) of the study. As shown in FIG. 23, microvesicular hepatic vacuolation differed significantly by treatment (K(4)=8.70, p<0.05, Kruskal-Wallis). Both PGX and JANUVIA tended to reduce the severity of steatosis, but the effect did not reach statistical significance. However, the combination of PGX and JANUVIA produced a statistically significant reduction (Group 1 vs. Group 4, PGX-JANUVIA, p<0.05; Dunn's test).

Figure 24:
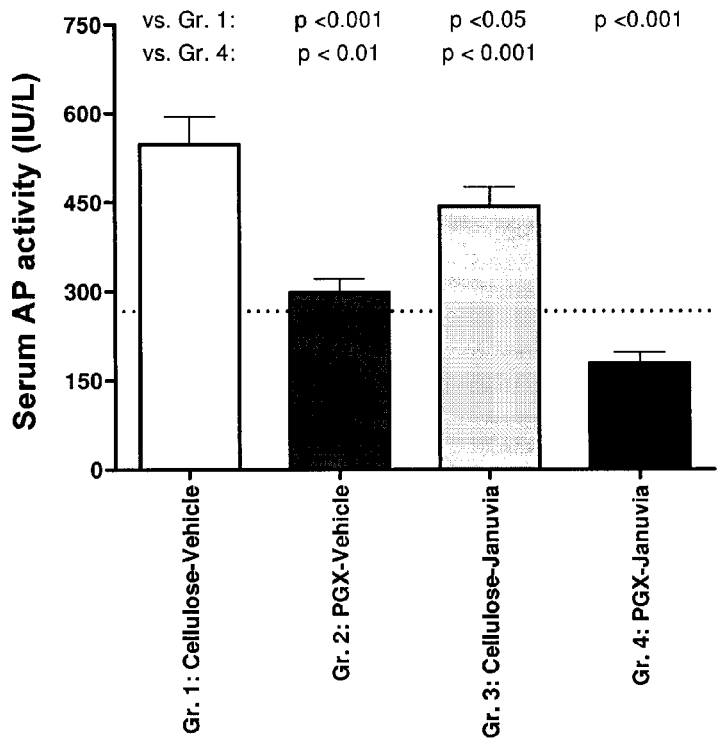
FIG. 24 graphically illustrates the alkaline phosphatase activity (IU/L) measured in a terminal blood sample obtained from rats in Groups 1-4 at week seven of the study, as described in EXAMPLE 7.

FIG. 24 graphically illustrates the alkaline phosphatase activity (IU/L) measured in a terminal blood sample obtained from rats in Groups 1-4 at week seven of the study. As shown in FIG. 24, serum alkaline phosphatase activity, measured in a terminal blood sample, was generally high, exceeding the reference range established with Sprague-Dawley rats (shown as the region below the dotted line in FIG. 24). Treatment groups differed significantly (F(3,38)=29.53, p<0.0001). Both PGX and JANUVIA alone significantly reduced alkaline phosphatase activity (Group 1 vs. Group 2, p<0.001; Group 1 vs. Group 3, p<0.05). The combination of PGX and JANUVIA further reduced activity to within the reference range. Combination-treated animals differed significantly from control (Group 1 vs. Group 4, p<0.001) and from both individual treatments (Group 2 vs. Group 4, p<0.01; Group 3 vs. Group 4, p<0.001).

Figure 25:
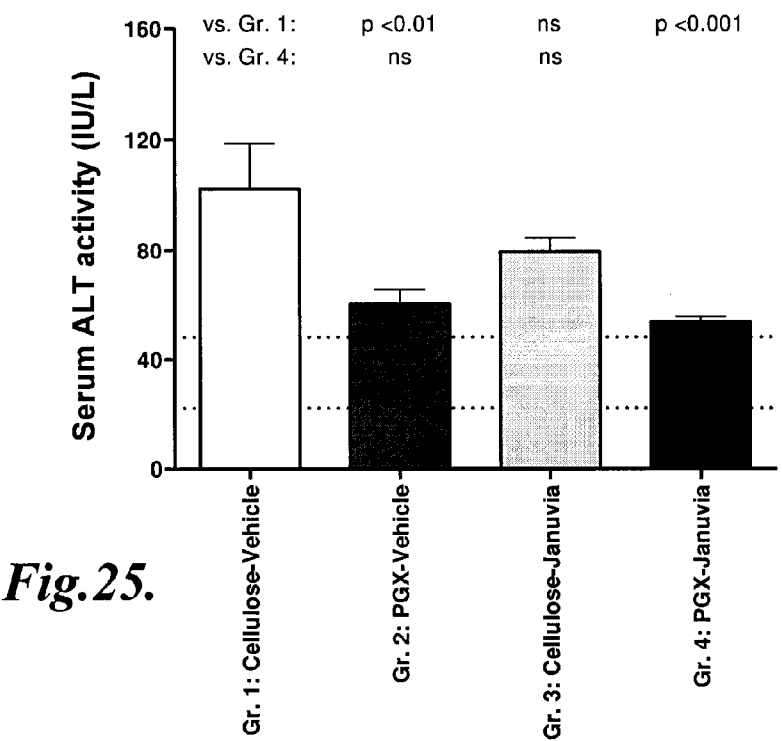
FIG. 25 graphically illustrates the serum alanine aminotransferase activity (ALT/SGPT) (IU/L) measured in a terminal blood sample obtained from rats in Groups 1-4 at week seven of the study, as described in EXAMPLE 7.

FIG. 25 graphically illustrates the serum alanine aminotransferase activity (also known as serum glutamic-pyruvic transaminase) (ALT/SGPT) (IU/L) measured in a terminal blood sample obtained from rats in Groups 1-4 at week seven of the study. As shown in FIG. 25, serum alanine aminotransferase activity (ALT/SGPT) was generally high, exceeding the reference range (shown as the region between the dotted lines in FIG. 25). The main effect of treatment was statistically significant (F(3,38)=7.76, p<0.0005). JANUVIA tended to decrease ALT activity, and PGX produced a significant decrease (Group 1 vs. Group 3, p>0.05; Group 1 vs. Group 2, p<0.01). The combination of PGX and JANUVIA tended to produce a greater decrease than either alone (Group 1 vs. Group 4, p<0.001; Group 4 vs. Group 2 or Group 3, p>0.05).

Figure 26:
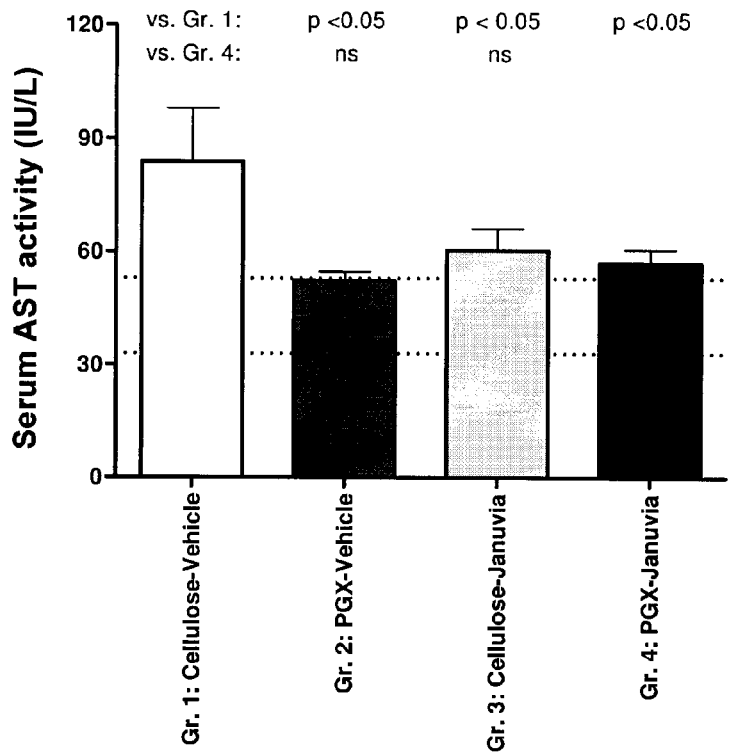
FIG. 26 graphically illustrates the level of serum aspartate aminotransferase activity (AST/SGOT) (IU/L) measured in a terminal blood sample obtained from rats in Groups 1-4 at week seven of the study, as described in EXAMPLE 7.

FIG. 26 graphically illustrates the level of serum aspartate aminotransferase (also known as serum glutamic-oxaloacetic transaminase) activity (AST/SGOT) (IU/L) measured in a terminal blood sample obtained from rats in Groups 1-4 at week seven of the study. As shown in FIG. 26, serum aminotransferase (AST) activity was generally high, exceeding the reference range (shown as the region between the dotted lines in FIG. 26). The main effect of treatment was statistically significant (F(3,38)=3.81, p<0.05). All three treatment groups reduced AST activity to approximately the top of the reference range, differing significantly from Group 1 (Group 1 vs. Group 2, 3, or 4, all p<0.05).

Figure 27:
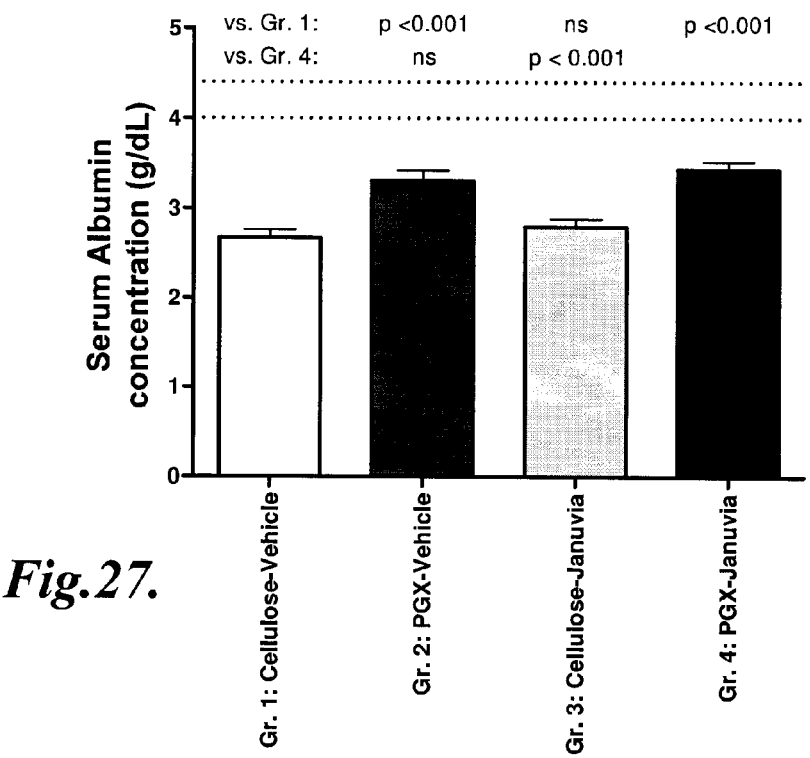
FIG. 27 graphically illustrates the albumin concentration (g/dL) measured in a terminal blood sample obtained from rats in Groups 1-4 at week seven of the study, as described in EXAMPLE 7.

FIG. 27 graphically illustrates the albumin concentration (g/dL) measured in a terminal blood sample obtained from rats in Groups 1-4 at week seven of the study. As shown in FIG. 27, circulating albumin concentrations were generally below the reference range (shown as the region between the dotted lines in FIG. 27), consistent with observations in other unrelated studies of rats with and without metabolic disease. As shown in FIG. 27, groups differed significantly (F(3,38)=14.47, p<0.0001). JANUVIA did not increase albumin concentrations (Group 1 vs. Group 3, p>0.05); however, both PGX and the combination of PGX and JANUVIA did (Group 1 vs. Group 2, p<0.05; Group 1 vs. Group 4, p<0.01).

Figure 28:
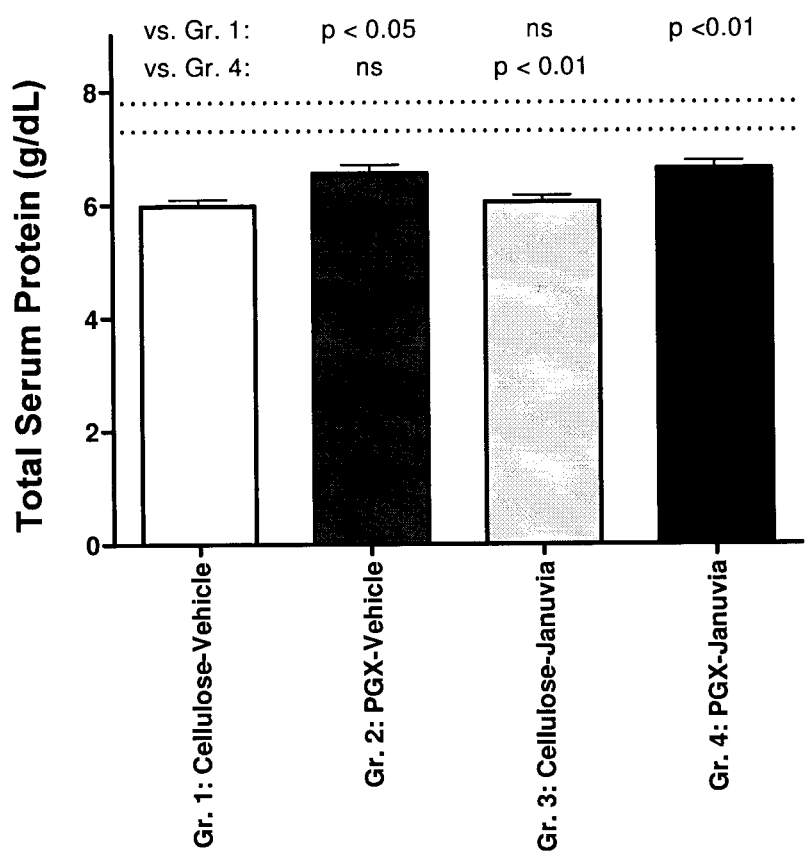
FIG. 28 graphically illustrates the total circulating protein concentration (g/dL) measured in a terminal blood sample obtained from rats in Groups 1-4 at week seven of the study, as described in EXAMPLE 7.

FIG. 28 graphically illustrates the total circulating protein concentration (g/dL) measured in a terminal blood sample obtained from rats in Groups 1-4 at week seven of the study. As shown in FIG. 28, the total circulating protein concentrations showed a pattern of effects very similar to albumin (compare FIG. 28 with FIG. 27). Groups differed significantly (F(3,38)=6.23, p<0.005). JANUVIA did not increase total protein concentrations (Group 1 vs. Group 3, p>0.05); however, both PGX and the combination of PGX and JANUVIA did (Group 1 vs. Group 2, p<0.05; Group 1 vs. Group 4, p<0.01).

As shown above in TABLE 19, cystic hepatocyte degeneration with fibrosis, scored from hematoxylin and eosin slides, was generally scored within normal limits (0; TABLE 19), and the main effect was not statistically significant. Hepatic focal infarction was generally scored within normal limits (0; TABLE 19), and the main effect was not statistically significant. As further shown in TABLE 19, circulating globulin concentrations were generally similar, and the groups did not differ significantly. Total bilirubin concentrations were generally low (TABLE 19), with each group including observations below the detection limit. A significant main effect was observed (F(3,34)=3.83, p<0.05), but no pair of groups differed significantly in post hoc testing (all p>0.05).

Summary of Results

TABLE 20

Summary of Significant Findings

| Parameter Measured | PGX only | JANUVIA only | Combination of PGX and JANUVIA | General Comments regarding parameter |
|---|---|---|---|---|
| Lean Mass (terminal) | significant increase | trend toward increase | significant increase; also significantly greater than PGX or JANUVIA alone | decreased by cachexia |

TABLE 20-continued

Summary of Significant Findings

| Parameter Measured | PGX only | JANUVIA only | Combination of PGX and JANUVIA | General Comments regarding parameter |
|---|---|---|---|---|
| Food consumption (all weeks) | significant decrease | significant decrease | significant decrease, also significantly lower than PGX or JANUVIA alone | decreased by PGX fiber, sometimes increased in diabetes |
| Non-fasted blood glucose (week 6) | significant decrease | no significant effect | significant decrease, also significantly lower than PGX or JANUVIA alone | increased in diabetes |
| Fasted blood glucose (week 6) | significant decrease | no significant effect | significant decrease, also significantly lower than PGX or JANUVIA alone | can be increased in diabetes |
| Hemoglobin glycosylation (week 6) | significant decrease | significant decrease | significant decrease, also significantly lower than PGX or JANUVIA alone | increased in diabetes |
| OGTT glucose AUC (week 6) | trend toward decrease | trend toward decrease | significant decrease, not significant v PGX or JANUVIA alone | increased in diabetes |
| OGTT insulin baseline (week 6) | significant increase | trend toward increase | significant increase, not significant v PGX or JANUVIA alone | increased with insulin resistance, then decreased with chronic diabetes |
| OGTT insulin AUC (week 6) | trend toward increase | trend toward increase | significant increase, not significant v PGX or JANUVIA alone | increased with insulin resistance, then decreased with chronic diabetes |
| total cholesterol (week 7) | significant decrease | no significant change | significant decrease; also significantly lower than PGX or JANUVIA alone | increased with dyslipidemia |
| serum chloride (week 7) | no significant change | no significant change | significant increase, also significantly higher than PGX or JANUVIA alone | significance unclear |
| pancreatic beta cell mass (terminal) | trend toward increase | no significant change | significant increase, also significantly higher than JANUVIA alone (but not PGX) | decreased with chronic diabetes |
| pancreatic islet hypertrophy (terminal) | significant increase | trend toward increase | no significant change, not significant v PGX or JANUVIA alone | increased with diabetes |
| pancreatic islet cell degeneration (terminal) | trend toward decrease | trend toward decrease | significant decrease, not significant v. PGX or JANUVIA alone | increased with diabetes |
| renal tubule degeneration/regeneration (terminal) | trend toward decrease | no significant change | significant decrease; also significantly lower than JANUVIA alone (but not PGX) | increased with diabetes |
| renal tubule dilatation (terminal) | trend toward decrease | no significant change | significant decrease, also significantly lower than JANUVIA alone (but not PGX) | increased with diabetes |
| blood urea nitrogen (terminal) | trend toward decrease | trend toward decrease | significant decrease, also significantly lower than PGX or JANUVIA alone | increase with renal damage, increased protein consumption |
| Hepatic Sudan Black Staining (terminal) | trend toward decrease | trend toward decrease | significant decrease, not significant v. either PGX or JANUVIA alone | increased with hepatic steatosis |
| Hepatic microvesicular vacuolation (terminal) | trend toward decrease | trend toward decrease | significant decrease, not significant v either PGX or JANUVIA alone | increased with hepatic damage |
| Serum alkaline phosphatase (terminal) | significant decrease | significant decrease | significant decrease, also significantly lower than PGX or JANUVIA alone | increased with hepatic damage, other diseases |
| Serum ALT/SGPT (terminal) | significant decrease | trend toward decrease | significant decrease, not significant v either PGX or JANUVIA alone | increased with hepatic damage, activity/diet changes |

TABLE 20-continued

Summary of Significant Findings

| Parameter Measured | PGX only | JANUVIA only | Combination of PGX and JANUVIA | General Comments regarding parameter |
|---|---|---|---|---|
| Serum AST/SGOT (terminal) | significant decrease | trend toward decrease | significant decrease, not significant v either PGX or JANUVIA alone | increased with hepatic damage, activity/diet changes |
| Serum albumin (terminal) | significant increase | no significant change | significant increase, also significantly higher than JANUVIA alone (but not PGX) | decreased with loss of hepatic function |
| total serum protein (terminal) | significant increase | no significant change | significant increase, also significantly higher than JANUVIA alone (but not PGX) | decreased with loss of hepatic function |

Note:
Results in Table 23 are described with reference to the cellulose control.

EXAMPLE 8

This Example demonstrates the effects of PGX and metformin (GLUCOPHAGE), or PGX and JANUMET (combination of sitagliptin and metformin), alone or in combination, in the Zucker FA/FA Rat Model fed a high fat diet.

Background/Rationale:

As a follow up to the study described in EXAMPLE 7; this study was designed to determine the effects of PGX, GLUCOPHAGE and JANUMET, alone or in combination, compared to controls (cellulose and vehicle, respectively), on measures of metabolic disease and disease mechanism (glycemic control, peptide hormones, enzyme activity, histology and histopathology) in the rat model Zucker FA/FA: ZDF/Crl-Lepr$^{fa/fa}$ rat, described in EXAMPLE 7.

Methods and Materials

Test Materials

A granulated dietary fiber composition, PGX was prepared as described in Example 1. PGX was incorporated into a basic rat chow (D11725) at 5% w/w by Research Diets, New Brunswick, N.J. Cellulose fiber was incorporated into a basic rat chow (D11725) at 5% w/w as a control.

Metformin (GLUCOPHAGE—850 mg) and a combination of metformin and sitagliptin (JANUMET—50 mg sitagliptin/1000 mg metformin)) were purchased as prescription tablets.

Dosing solutions of metformin (20 mg metformin/mL) and sitagliptin/metformin (1 mg/mL sitagliptin, 20 mg metformin/mL) were prepared by homogenizing GLUCOPHAGE and JANUMET drug tablets, respectively, in distilled water and separating particulate matter by centrifugation. Dosing solutions were prepared fresh weekly. Following formulation, solutions were stored refrigerated.

Quality Control

Before the beginning of the dosing studies, dosing solutions were analyzed. Using JANUMET and GLUCOPHAGE tablets as a reference, well-homogenized samples of fresh dosing solution were analyzed to verify concentration. Samples from the top, middle and bottom of containers of dosing solution were analyzed to verify homogeneity. Finally, well-homogenized samples of 10 day old dosing solutions were also analyzed to verify stability.

During the study, aliquots of each preparation of dosing solution were stored at −80° C. After the conclusion of the study, these stored samples were analyzed to verify the concentration of the test article.

Study Design

Animals 66 young adult (7-8 week old) male rats (Zucker ZDF/Crl-Lepr$^{fa/fa}$), were obtained from Charles River Laboratories, Kingston, N.Y. The rats were housed in cages which conformed to size standards in Guide for the Care and Use of Laboratory Animals (Nat'l Res. Council, 1996). Bedding was changed at least twice per week. The animals were maintained at a temperature range of 18-22° C., humidity 44-68%, and a photoperiod of 12 hour light/dark cycle. The rats were acclimated for 12 days prior to the start of the study. Each animal was given a sequential number and was uniquely identified with a stainless steel ear tag or other appropriate, permanent method. Morbidity and mortality checks were carried out twice daily during the study.

Test Diets

Diets containing 45% fat and either 5% cellulose (w:w) or 5% PGX (w:w) (based on Research Diets formula D12451) were available ad libitum, except for the fasted tests. Filtered tap water was available ad libitum.

GLUCOPHAGE and JANUMET were administered by oral gavage (formulated at 20 mg metformin/mL and 1 mg sitagliptin/mL+20 mg metformin/mL, as base and as labeled, respectively, in water for dosing at 10 mL/kg). Gavage treatments were administered in the morning, with samples and data collected after treatment. Dosing volumes were calculated on the basis of each week's body weights.

Study Phases

The study was divided into an acclimation phase (the days from delivery to first dose; referred to as week 0); a test article administration phase (six full weeks, numbered 1-6 below), and a final takedown phase (week 7). TABLE 21 shows the measurements that were carried out during the various phases of the study.

TABLE 21

Study Phases and Measurements

| Week | Phase | Regular Measures | Single Measurements |
|---|---|---|---|
| 0 | Acclimation | body weight; food consumption; fed/fasted glucose testing | HbA1c |
| 1 | Test article | body weight; food consumption; fed/fasted glucose testing | none |

TABLE 21-continued

Study Phases and Measurements

| Week | Phase | Regular Measures | Single Measurements |
|---|---|---|---|
| 2 | Test article | body weight; food consumption; fed/fasted glucose testing | none |
| 3 | Test article | body weight; food consumption; fed/fasted glucose testing | HbA1c |
| 4 | Test article | body weight; food consumption; fed/fasted glucose testing | none |
| 5 | Test article | body weight; food consumption; fed/fasted glucose testing | none |
| 6 | Test article | body weight; food consumption; fed/fasted glucose testing | HbA1c; Fasted oral glucose tolerance test |
| 7 | Takedown | body weight; food consumption | glucose-loaded peptide analysis; fasted peptide analysis; lipid analysis; clinical chemistry; tissue and fluid harvesting for analysis |

After acclimation, rats were allocated to treatment groups according to weight (in a stratified random fashion), as shown in TABLE 22.

TABLE 22

Study Groups

| Group | Fiber (diet) | Gavage |
|---|---|---|
| 1 (control) | Cellulose | Vehicle (water) |
| 2 (PGX alone) | PGX | Vehicle (water) |
| 3 (GLUCOPHAGE/control) | Cellulose | 200 mg/kg/day metformin (as base: GLUCOPHAGE) |
| 4 (GLUCOPHAGE/PGX) | PGX | 200 mg/kg/day metformin (as base: GLUCOPHAGE) |
| 5 (JANUMET/control) | Cellulose | 10 mg/kg/day sitagliptin, 200 mg/kg/day metformin (as labeled; JANUMET) |
| 6 (JANUMET/PGX) | PGX | 10 mg/kg/day sitagliptin, 200 mg/kg/day metformin (as labeled; JANUMET) |

Regular Study Measures

Rats were weighed once each week, as shown in TABLE 21. Food was weighed three times per week, and spillage was determined twice per week. These values were used to determine daily average food consumption for each week following acclimation. Glucose concentrations were determined using a hand-held glucose meter (e.g., Bayer Asencia Elite). Blood was collected via tail nick following gavage dosing; one sample was collected when food was available for the previous 24 hours (non-fasted), and one sample was collected on another day when food was not available overnight (16 h fasted). The target time for sample collection was one hour after gavage dosing.

Oral Glucose Tolerance Test (OGTT)

A fasted (16 h) OGTT was conducted after gavage dosing. After baseline samples were collected, glucose was administered by gavage (1 g/kg, PO). Blood samples were collected via tail nick at 10, 20, 30, 60, and 120 minutes after glucose administration. Blood glucose concentrations were determined using a hand-held glucose meter. The remainder of the sample was allowed to clot, and centrifuged to separate serum (target volume, 80 µL). Serum samples were frozen for insulin analysis. The target time for the start of the procedure (baseline sample collection) was one hour after gavage dosing.

Glucose-Loaded Peptide Analysis

Rats were fasted overnight and given their regular gavage treatment in the morning. After baseline samples were collected, glucose was administered by gavage (2 g/kg, PO). Blood samples (target volume: 80 µL plasma) were collected via tail nick at 15, 30, 60, and 90 minutes after glucose administration. Blood was collected into anticoagulant tubes (e.g., $K_3$EDTA). Peptidase inhibitors (diprotin A, AEBSF and Sigma protease inhibitor cocktail, to final concentrations of 34 µg/ml, 1 mg/ml and 1% v:v; target volumes: 2%, 2.5% and 1% v:v, respectively) were used. Plasma was separated by centrifugation and frozen for peptide analysis. The target time for the start of the procedure (baseline sample collection) was one hour after gavage dosing.

Lipid Determinations, Plasma DPPIV Activity and Clinical Chemistry (Necropsy)

Rats were fasted overnight and given their regular gavage treatments in the morning. Rats were anesthetized with isoflurane, and a blood sample was collected via cardiac puncture. No peptidase inhibitors were used. A portion of this sample was tested for lipid concentrations (total, LDL, and HDL cholesterol and triglycerides) using an analyzer (e.g., Polymer Technology Systems CardioChek, PA). Blood was diluted with two volumes of saline prior to analysis. Plasma was separated by centrifugation and flash-frozen for DPPIV activity determination. The remainder was prepared for comprehensive clinical chemistry analysis.

Tissue Collection (Necropsy)

Following sample collection, a limited necropsy was performed. A section of ileum (approximately one inch, collected one inch rostral to the cecum) was rinsed in chilled saline and flash frozen; this sample was analyzed for DPPIV mRNA. One kidney was flash-frozen for DPPIV mRNA analysis; one liver lobe was flash frozen for DPPIV activity and mRNA analysis. One or two small wedges of liver lobe (ca. 100 mg) were cut before flash-freezing. The pancreas (collected as a pancreatic pluck, with associated tissue including the remainder of the intestine), one liver lobe and one kidney were post-fixed for staining with hematoxylin and eosin. The pancreas was also processed using insulin immunohistochemistry for beta cell determination; and one liver lobe was snap-frozen for staining with Sudan Black. The remainder of the carcass was analyzed for lean mass, fat mass and bone content by dual energy X-ray absorptiometry (i.e., DEXA).

Hemoglobin Glycosylation Measurements

The extent of hemoglobin glycosylation was determined using a clinical analyzer (e.g., Bayer DCA2000). Blood samples for analysis were collected via tail nick.

Statistical Methods

Data was analyzed by an appropriate analysis of variance method (one-way ANOVA, two-way repeated measures ANOVA or Kruskal-Wallis test). All six treatment groups were treated as a single factor.

Results

Body Weight, Body Composition and Food Consumption

Figure 29:
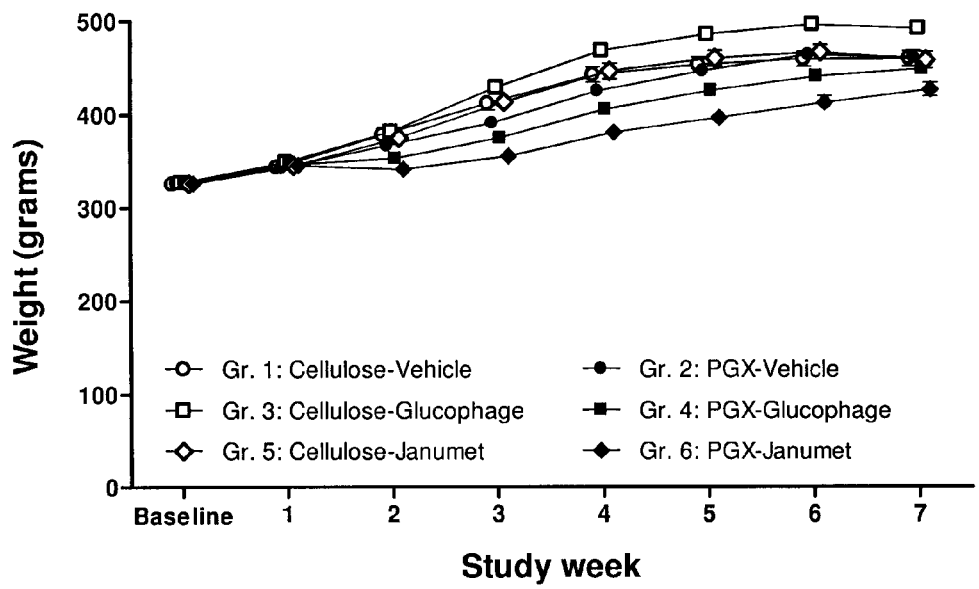
FIG. 29 graphically illustrates the body weight (grams) of the rats in Groups 1-6 measured weekly over the course of the 7 week study, as described in EXAMPLE 8.

FIG. 29 graphically illustrates the body weight (grams) of the rats in Groups 1-6 measured weekly over the course of the 7 week study. As shown in FIG. 29, all groups gained weight over the course of the study. However, groups fed PGX-containing diet (5%, w:w) tended to gain less weight. Weight gain was decreased by treatment with GLUCOPHAGE (200 mg/kg metformin as base, qd, by gavage) or JANUMET (a fixed combination of 10 mg/kg sitagliptin as base and 200 mg/kg metformin as the hydrochloride salt, qd, by gavage) in combination with PGX. However, in combination with cellulose (control fiber, 5% w:w), JANUMET did not change weight gain, and GLUCOPHAGE increased weight gain.

Body weights were analyzed at baseline and at the final measurement (week 7). As shown in FIG. 29 and TABLE 23, baseline body weights did not differ between groups. Week 7 body weights differed significantly ((F(5,65)=8.75, p<0.0001). Post hoc testing showed Group 6 (PGX-JANUMET) to have significantly lower body weights than all other groups (p<0.05 to p<0.001 by Newman-Keuls test). Group 3 (cellulose-GLUCOPHAGE) body weights were significantly higher than all other groups (p<0.01 to p<0.001). No other comparisons reached statistical significance.

Body composition was measured using dual-energy X-ray absorptiometry (DEXA) at the end of the study (i.e., after a limited necropsy for histopathology samples). The primary endpoints were fat mass, lean mass and bone mineral content. Tissue composition (% body fat) and fat-free mass were also reported, but the information in these measures was redundant with other measures.

Figure 30:
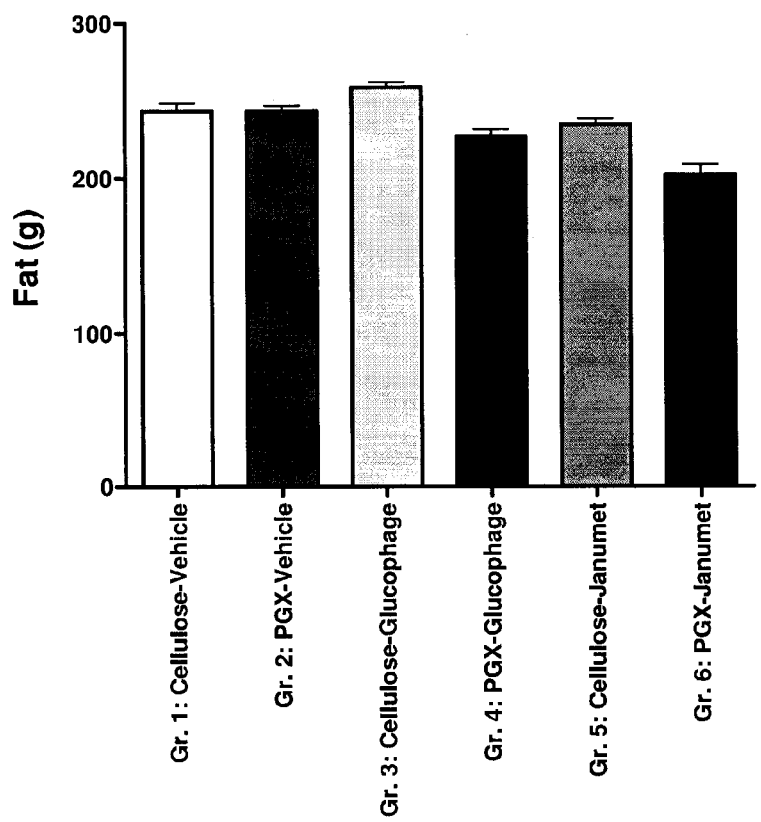
FIG. 30 graphically illustrates the fat mass (grams) of the rats in Groups 1-6 measured at week 7 of the study, as described in EXAMPLE 8.

FIG. 30 graphically illustrates the fat mass (grams) of the rats in Groups 1-6 measured at week 7 of the study. As shown in FIG. 30, fat mass tended to parallel the results seen in terminal body weight (compare FIG. 29 and FIG. 30). Fat mass differed significantly between groups (F(5,59)=17.61, p<0.0001). Group 6 had significantly lower fat mass than all other groups (p<0.001). Group 3 had significantly higher fat mass than Group 4 (PGX-GLUCOPHAGE), Group 5 (Cellulose-JANUMET) and Group 6 (JANUMET-PGX). No other comparisons reached statistical significance.

As shown below in TABLE 23, tissue composition (% body fat) differed significantly between groups (F(5,59)=4.86, p<0.005). Significant post hoc differences were a subset of those seen for fat mass (compare with FIG. 30). Group 6 (JANUMET-PGX) differed significantly from all other groups (p<0.05 to p<0.01). No other differences reached statistical significance for tissue composition.

Figure 31:
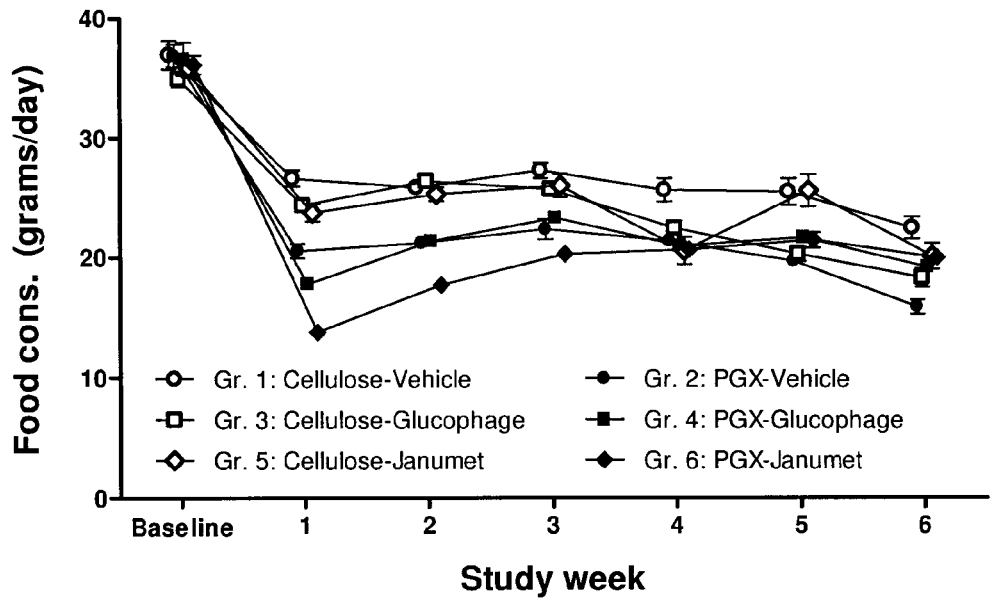
FIG. 31 graphically illustrates the food consumption (grams/day) of the rats in Groups 1-6 measured weekly over the course of the 7 week study, as described in EXAMPLE 8.

FIG. 31 graphically illustrates the food consumption (grams/day) of the rats in Groups 1-6 measured weekly over the course of the 7 week study. For analysis, food consumption values were averaged for each rat (shown in TABLE 23). As shown in FIG. 31, groups fed a PGX-containing diet tended to consume less than groups fed the cellulose-containing diet. All groups showed a decrease from baseline consumption during the first week of the study. The most substantial decreases were associated with a slight rebound, while all groups showed a gradual decrease. Statistically significant differences were observed between PGX-fed groups and cellulose-fed groups (p<0.01 to p<0.001). In addition, among cellulose-fed groups, both GLUCOPHAGE and JANUMET decreased food consumption (p<0.01) vs. vehicle. This effect was not observed among PGX-fed groups. This difference is striking when considered in combination with body weights. Group 5 showed relatively low food consumption with vehicle-like body weight. Group 3 showed relatively low food consumption with the highest final body weights of any group. While not wishing to be bound by any particular theory, this pattern could be explained by changed metabolic efficiency, with the change reversed by feeding of PGX fiber.

TABLE 23

Body Weight, Tissue Composition and Food Consumption

|  | Group 1: Cellulose-Vehicle | Group 2: PGX-Vehicle | Group 3: Cellulose-GLUCOPHAGE | Group 4: PGX-GLUCOPHAGE | Group 5: Cellulose-JANUMET | Group 6: PGX-JANUMET |
|---|---|---|---|---|---|---|
| Baseline body weight (g) | 325.3 ± 5.2 | 325.6 ± 5.1 | 326.6 ± 5.6 | 327.9 ± 6.5 | 325.5 ± 4.3 | 325.9 ± 4.1 |
| Week 7 body weight (g) | 459.7 ± 8.0 | 461.2 ± 7.1 | 492.5 ± 4.3 | 448.8 ± 6.7 | 458.4 ± 8.8 | 426.8 ± 7.3 |
| Tissue composition (% fat) | 66.9 ± 0.9 | 66.6 ± 0.8 | 67.1 ± 0.8 | 65.1 ± 0.8 | 65.9 ± 0.4 | 62.2 ± 1.1 |
| Fat free mass (g) | 120.4 ± 3.6 | 121.9 ± 3.9 | 126.9 ± 3.5 | 121.7 ± 3.0 | 121.5 ± 3.1 | 122.0 ± 3.3 |
| Mean food consumption (g/day) | 25.5 ± 0.6 | 20.2 ± 0.3 | 22.9 ± 0.4 | 20.7 ± 0.2 | 23.5 ± 0.8 | 19.0 ± 0.4 |

As further shown in TABLE 23, fat-free mass, a composite of lean mass and bone mineral mass, did not differ significantly between groups. It is further noted that lean mass and bone mineral content did not differ significantly between groups (data not shown).

Glucose Homeostasis: Continuing Measures

Figure 32:
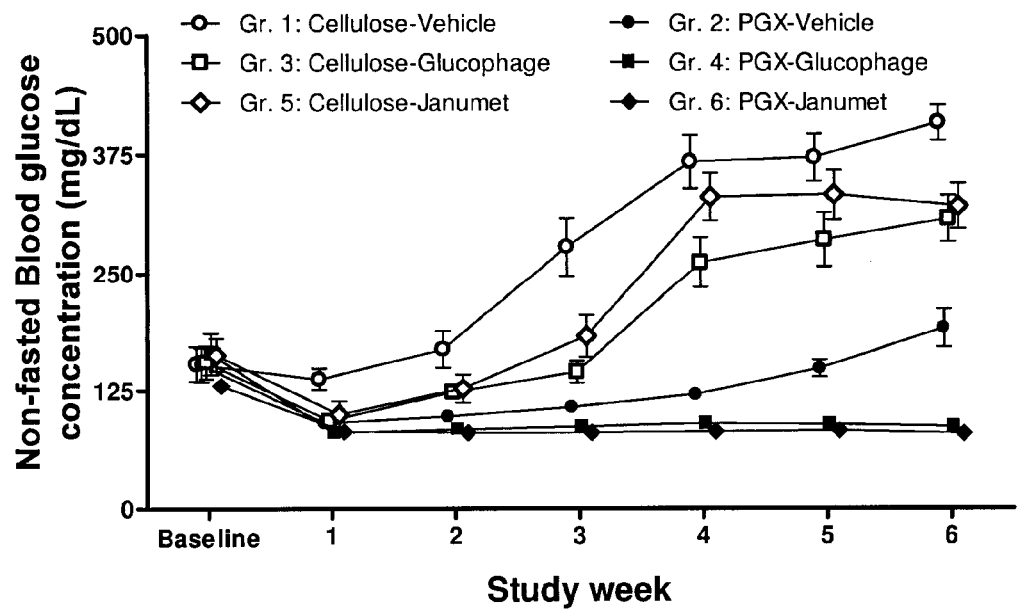
FIG. 32 graphically illustrates the level of non-fasted blood glucose (mg/dL) of the rats in Groups 1-6 measured at weekly intervals over the course of the 7 week study, as described in EXAMPLE 8.

FIG. 32 graphically illustrates the level of non-fasted blood glucose (mg/dL) of the rats in Groups 1-6 measured at weekly intervals over the course of the 7 week study. As shown in FIG. 32, non-fasted blood glucose, measured at weekly intervals throughout the study, showed clear differences between groups. All cellulose-fed groups showed a progressive increase in blood glucose, which was reduced slightly by GLUCOPHAGE and JANUMET. Rats fed PGX and treated with vehicle showed a slight increase, while groups fed PGX and treated with GLUCOPHAGE or JANUMET maintained low blood glucose concentrations.

Statistical analysis of blood glucose concentrations, as shown below in TABLE 24, were conducted using data from baseline and the last measurement, as was done for body weight.

TABLE 24

Glucose Homeostasis-Continuing Measures

|  |  | Group 1: Cellulose-Vehicle | Group 2: PGX-Vehicle | Group 3: Cellulose-GLUCOPHAGE | Group 4: PGX-GLUCOPHAGE | Group 5: Cellulose-JANUMET | Group 6: PGX-JANUMET |
|---|---|---|---|---|---|---|---|
| Non-fasted blood glucose (mg/dL) | Baseline | 153.3 ± 18.6 | 152.5 ± 18.3 | 155.3 ± 17.4 | 163.9 ± 22.0 | 163.0 ± 17.5 | 130.1 ± 6.5 |
|  | Week 6 | 408.5 ± 18.5 | 191.2 ± 20.2 | 307.7 ± 24.4 | 86.91 ± 4.6 | 321.0 ± 23.5 | 79.4 ± 2.1 |
| 16 h fasted blood glucose (mg/dL) | Baseline | 95.3 ± 5.1 | 97.6 ± 2.4 | 92.0 ± 3.8 | 94.5 ± 3.2 | 87.6 ± 3.8 | 94.5 ± 4.3 |
|  | Week 6 | 331.9 ± 18.3 | 187.1 ± 20.7 | 261.0 ± 34.0 | 88.6 ± 4.2 | 271.3 ± 24.8 | 84.9 ± 3.0 |
| Hemoglobin glycosylation (%) | Baseline | 4.1 ± 0.1 | 4.0 ± 0.1 | 4.0 ± 0.1 | 4.1 ± 0.1 | 4.2 ± 0.1 | 4.0 ± 0.1 |
|  | Week 6 | 6.4 ± 0.2 | 4.4 ± 0.1 | 4.5 ± 0.2 | 3.8 ± 0.1 | 5.5 ± 0.4 | 3.7 ± 0.0 |

As shown in TABLE 24, baseline non-fasted blood glucose concentrations did not differ significantly between groups. As further shown in TABLE 24, Week 6 non-fasted blood glucose concentrations differed significantly between groups ($F(5,65)=56.73$, $p<0.0001$). All group differences were statistically significant except for the comparisons of GLUCOPHAGE and JANUMET-treated groups, whether fed cellulose (Group 3 vs. Group 5) or PGX (Group 4 vs. Group 6).

Fasted blood glucose (food withdrawn the previous night, about 16 h before blood sampling) was also measured at weekly intervals throughout the study. As shown in TABLE 24, baseline fasted blood glucose concentrations did not differ significantly between groups. However, clear differences between groups were apparent in the fasted blood glucose concentrations measured at week 6.

Figure 33:
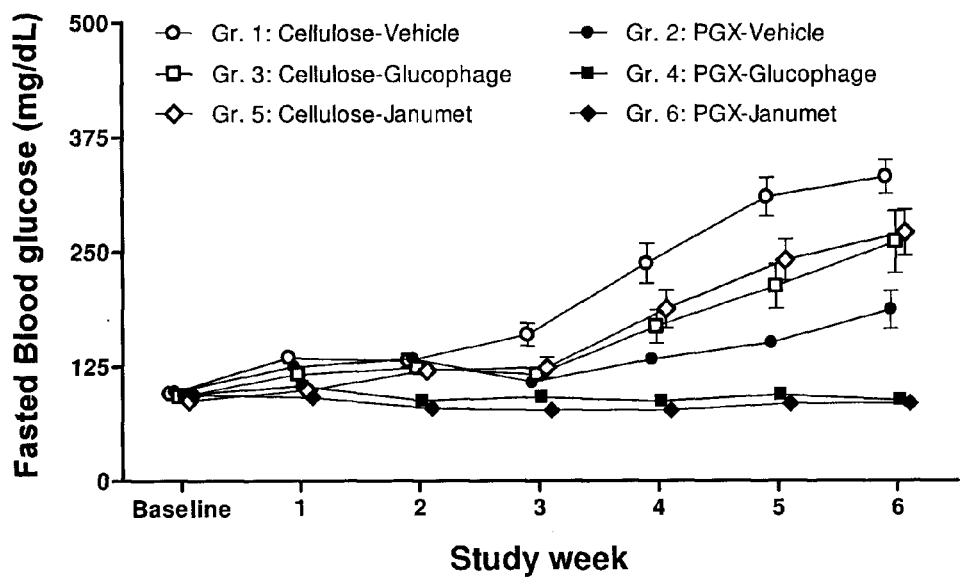
FIG. 33 graphically illustrates the level of fasted blood glucose (mg/dL) of the rats in Groups 1-6 measured at weekly intervals over the course of the 7 week study, as described in EXAMPLE 8.

FIG. 33 graphically illustrates the level of fasted blood glucose (mg/dL) of the rats in Groups 1-6 measured at weekly intervals over the course of the 7 week study. As shown in FIG. 33, blood glucose levels were lower than those observed in non-fasted conditions, and did not decrease for any group; otherwise the group trends were similar (compare FIG. 32 and FIG. 33). Week 6 fasted glucose concentrations differed significantly between groups (TABLE 24) $F(5,59)=24.33$, $p<0.0001$). All group differences were statistically significant except for the comparisons of GLUCOPHAGE and JANUMET-treated groups, whether fed cellulose (Group 3 vs. Group 5) or PGX (Group 4 vs. Group 6).

Figure 34:
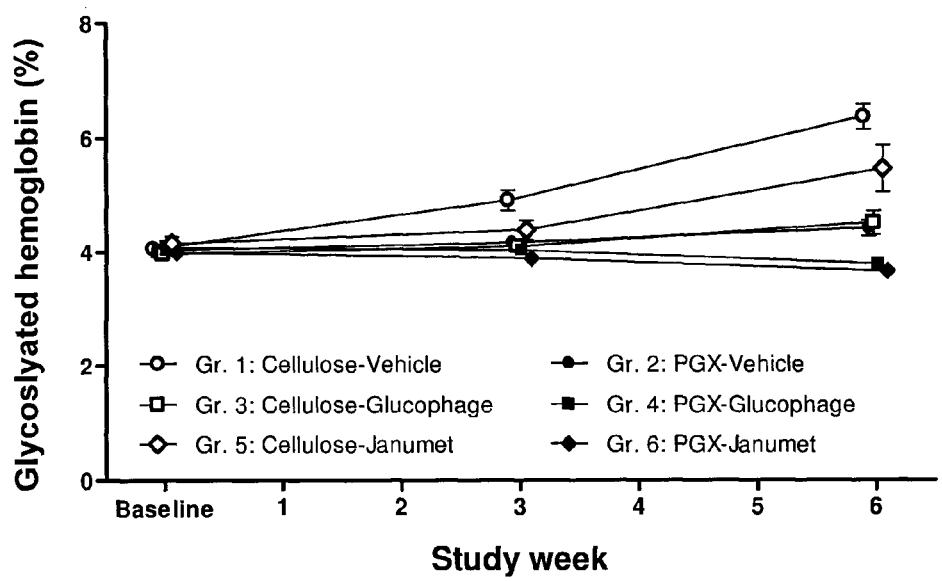
FIG. 34 graphically illustrates the amount (%) of glycosylated hemoglobin in blood samples obtained from the rats in Groups 1-6, as determined at baseline, week 3 and week 6 of the study, as described in EXAMPLE 8.

FIG. 34 graphically illustrates the amount (%) of glycosylated hemoglobin in blood samples obtained from the rats in Groups 1-6, as determined at baseline, week 3 and week 6 of the study. As shown in FIG. 34 and TABLE 24, baseline measurements of hemoglobin glycosylation did not differ significantly between the groups. However, as further shown in TABLE 24 and FIG. 34, hemoglobin glycosylation generally increased over the course of the study, a result that is consistent with observations of increasing blood glucose concentrations under both fasting and non-fasting conditions. As measured at week 6, hemoglobin glycosylation differed significantly between the groups, as shown in TABLE 24 and FIG. 34 ($F(5,52)-36.49$, $p<0.0001$). All group differences were statistically significant except for the comparisons of GLUCOPHAGE and JANUMET-treated groups fed PGX (Group 4 vs. Group 6) and the comparison of Group 2 (PGX-Vehicle) vs. Group 3 (Cellulose-Vehicle).

Glucose Homeostasis-OGTT Measures

Figure 35:
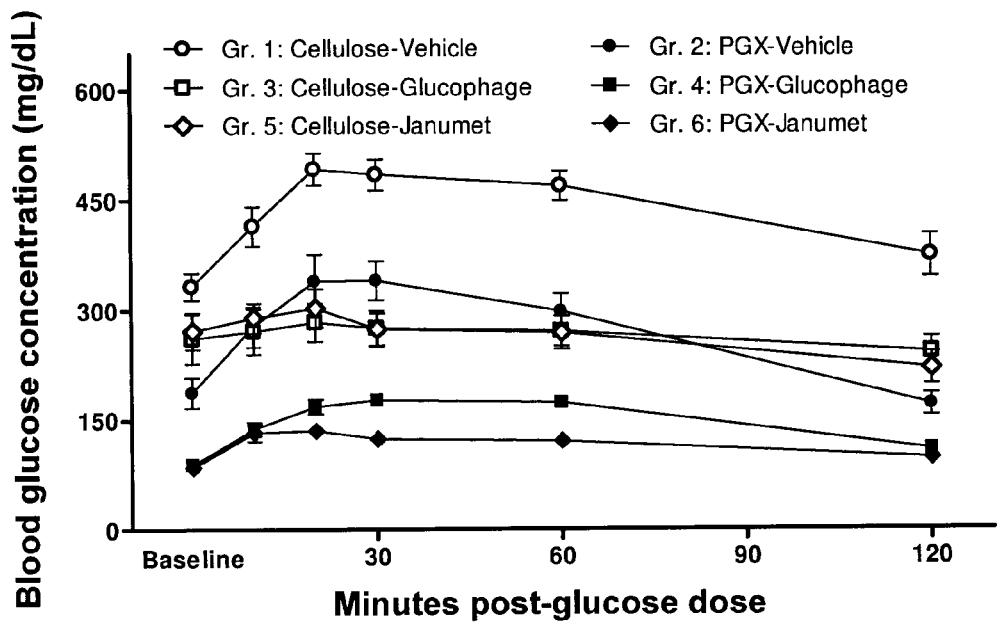
FIG. 35 graphically illustrates the concentration of blood glucose (mg/dL) measured over a two hour time period post-glucose administration in a 16 hour fasted oral glucose tolerance test carried out in the rats in Groups 1-6, as described in EXAMPLE 8.

In an oral glucose tolerance test run under overnight fasted conditions at week 6, there were substantial differences observed between groups throughout the observation period, as shown in FIG. 35 and TABLE 28. FIG. 35 graphically illustrates the concentration of blood glucose (mg/dL) measured over a two hour time period post-glucose administration in a 16 hour fasted oral glucose tolerance test carried out in the rats in Groups 1-6. TABLE 25 provides the measurements of the OGTT test. Data collected following glucose administration were analyzed by integration to area under the curve for the time course following subtraction of the baseline (AUC).

TABLE 25

Glucose Homeostasis-OGTT Measures

|  |  | Group 1: Cellulose-Vehicle | Group 2: PGX-Vehicle | Group 3: Cellulose-GLUCOPHAGE | Group 4: PGX-GLUCOPHAGE | Group 5: Cellulose-JANUMET | Group 6: PGX-JANUMET |
|---|---|---|---|---|---|---|---|
| blood glucose | Baseline (μg/dL) | 331.9 ± 18.3 | 187.1 ± 20.7 | 261.0 ± 34.0 | 88.6 ± 4.2 | 271.3 ± 24.8 | 84.9 ± 3.0 |
|  | $AUC_{(0-120)}$ (μg * h/dL, baseline-subtracted) | 12699 ± 1302 | 9236 ± 1209 | 439 ± 1872 | 7431 ± 424 | −1134 ± 1564 | 3722 ± 617 |
| serum insulin | Baseline (ng/dL) | 21.9 ± 4.9 | 50.2 ± 6.0 | 65.5 ± 12.6 | 21.7 ± 2.9 | 35.5 ± 8.0 | 12.4 ± 1.7 |
|  | $AUC_{(0-120)}$ (ng * h/dL, baseline-subtracted) | −46.8 ± 73.1 | −304.3 ± 229.9 | −833.0 ± 379.1 | −28.0 ± 249.4 | −165.9 ± 294.2 | 497.2 ± 144.0 |
| CISI Score |  | 0.20 ± 0.04 | 0.12 ± 0.02 | 0.08 ± 0.01 | 0.46 ± 0.06 | 0.15 ± 0.02 | 0.86 ± 0.15 |

As shown in FIG. 35 and TABLE 25, AUC differed significantly between groups (F(5,57)=17.28, p<0.0001). All groups differed significantly in post hoc testing except for comparisons between GLUCOPHAGE and JANUMET (Group 3 vs. Group 5; Group 4 vs. Group 6), between Group 3 (Cellulose-GLUCOPHAGE) and Group 6 (PGX-JANUMET) and between Group 1 (Cellulose-vehicle) and Group 2 (PGX-vehicle).

Figure 36:
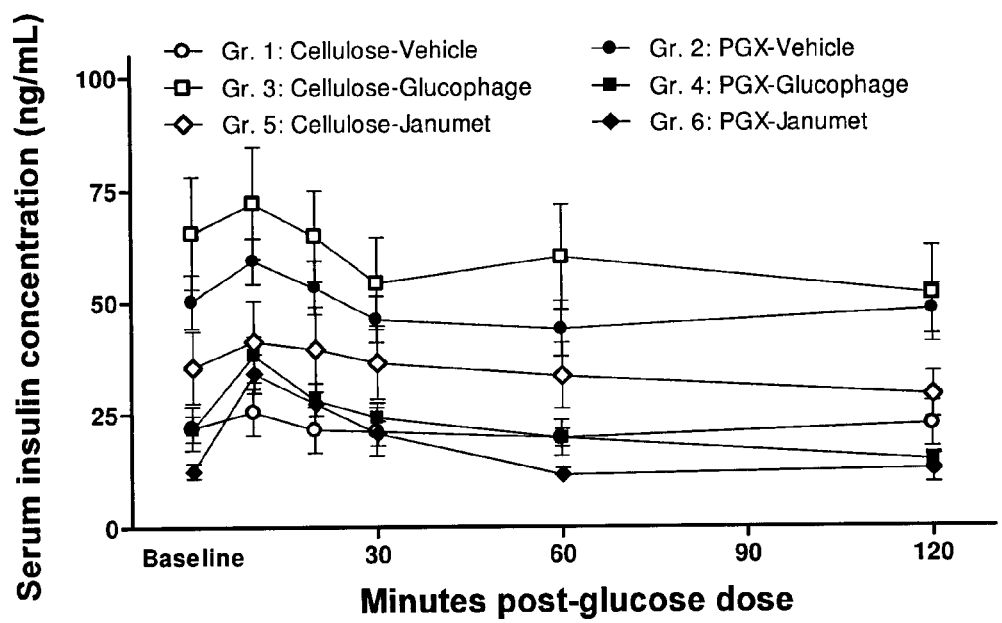
FIG. 36 graphically illustrates the serum insulin concentration (ng/dL) in blood samples obtained over a two hour time period post-glucose administration in a 16 hour fasted oral glucose tolerance test carried out at week 6 of the study in the rats in Groups 1-6, as described in EXAMPLE 8.

FIG. 36 graphically illustrates the serum insulin concentration (ng/dL) in blood samples obtained over a two hour time period post-glucose administration in a 16 hour fasted oral glucose tolerance test carried out at week 6 of the study in the rats in Groups 1-6. As shown in FIG. 36, clear differences were observed between the groups. The pattern of insulin concentrations was consistent with a combination of varying degrees of basal insulin resistance, observed as higher baseline concentrations, and pancreatic dysfunction, observed as blunted insulin baselines and responses (i.e., lower AUC values). Based on baseline and AUC measures, the pattern shown in TABLE 26 was observed:

TABLE 26

Pattern of Serum Insulin Concentration

| Group | Baseline | AUC | physiological significance |
|---|---|---|---|
| 6 (PGX-JANUMET) | low | high | more normal |
| 4 (PGX-GLUCOPHAGE) | low | high | more normal |
| 2 (PGX-Vehicle) | high | intermediate | intermediate |
| 3 (Cellulose-GLUCOPHAGE) | high | intermediate | intermediate |
| 5 (Cellulose-JANUMET) | high | low | more pathological |
| 1 (Cellulose-Vehicle) | low | low | more pathological |

As shown in TABLE 26, baseline insulin concentrations differed significantly (F(5,59)=8.28, p<0.0001). Of the differences listed above, the difference between Groups 4 and 2 and between Groups 3 and 5 reached statistical significance (p<0.05); the others did not. As further shown in TABLE 26, insulin AUC values also differed significantly (F(5,59)=3.02, p<0.05). However, none of the post hoc comparisons above reached statistical significance.

Figure 37:
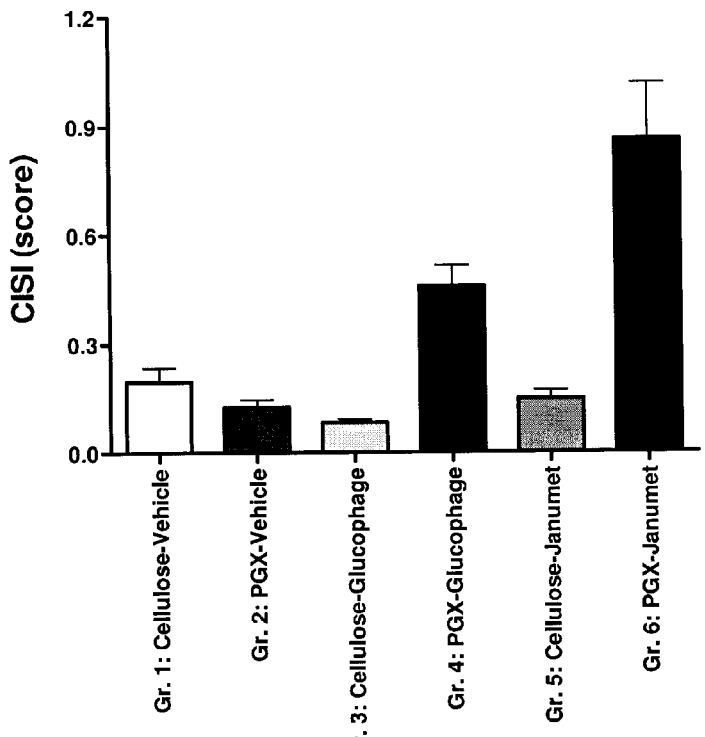
FIG. 37 graphically illustrates the composite insulin sensitivity index (CISI) score calculated from the serum insulin concentrations shown in FIG. 36, as described in EXAMPLE 8.

As shown in TABLE 26, composite insulin sensitivity index (CISI) scores were calculated to summarize the oral glucose tolerance test, as shown in FIG. 37. These scores differed significantly by group (F(5,57)=17.61, p<0.0001). Group 6 (PGX-JANUMET) and Group 4 (PGX-GLUCOPHAGE) were significantly higher than from all other groups; however, no other comparisons reached statistical significance (all p>0.05).

Lipid Analysis

Figure 38:
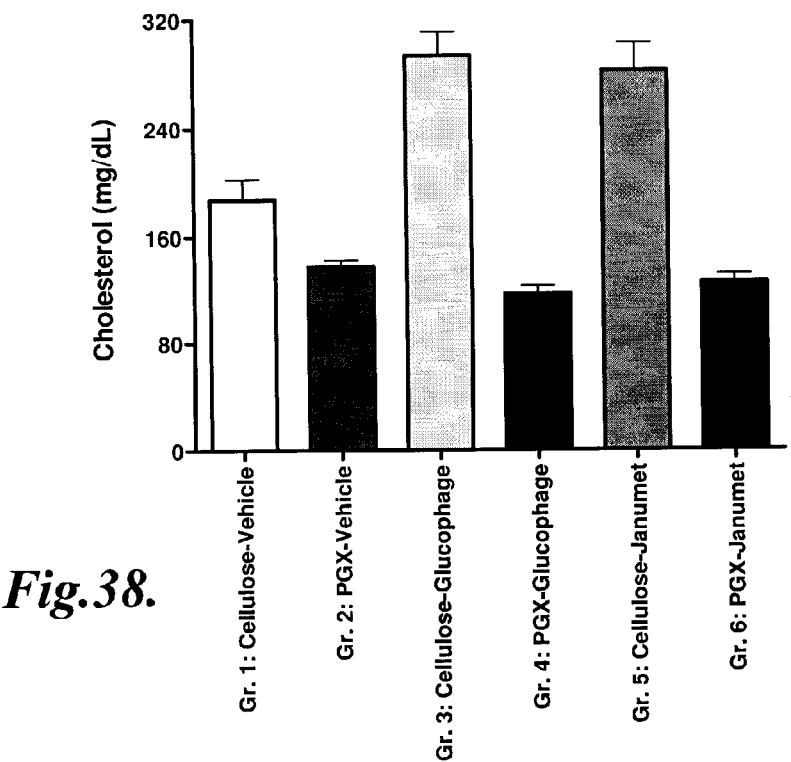
FIG. 38 graphically illustrates the total cholesterol measured in the blood samples obtained from the rats from Groups 1-6 at week seven, as described in EXAMPLE 8.

The lipid content of a terminal blood sample from each rat was analyzed at week seven. FIG. 38 graphically illustrates the total cholesterol measured in the blood samples obtained from the rats from Groups 1-6 at week seven. As shown in FIG. 38, total cholesterol differed significantly by group (F(5,44)=47.75, p<0.0001). Compared to groups fed cellulose, groups fed PGX showed lower blood cholesterol (e.g., Group 1, Cellulose-vehicle vs. Group 2, PGX-vehicle, p<0.01). Groups fed cellulose-containing diet and treated with either GLUCOPHAGE (Group 3) or JANUMET (Group 5) showed increased cholesterol (both p<0.001 vs. Group 1). In contrast, in groups fed PGX-containing diet, these treatments produced a trend toward lower cholesterol concentrations (Group 4, PGX-GLUCOPHAGE or Group 6, PGX-JANUMET vs. Group 2, PGX-Vehicle, p>0.05).

Clinical Chemistry

A terminal blood sample from each rat at week seven was analyzed for clinical chemistry parameters. The results are shown in TABLE 27.

TABLE 27

| | Group 1: Cellulose-Vehicle | Group 2: PGX-Vehicle | Group 3: Cellulose-GLUCOPHAGE | Group 4: PGX-GLUCOPHAGE | Group 5: Cellulose-JANUMET | Group 6: PGX-JANUMET | Reference Range |
|---|---|---|---|---|---|---|---|
| Creatine kinase (IU/L) | 225.7 ± 42.5 | 271.5 ± 77.9 | 207.6 ± 86.2 | 121.1 ± 13.8 | 220.1 ± 78.2 | 175.6 ± 27.0 | not available |
| Calcium (mg/dL) | 10.5 ± 0.1 | 11.0 ± 0.1 | 10.4 ± 0.6 | 10.8 ± 0.1 | 10.6 ± 0.2 | 10.7 ± 0.1 | 6 to 10.6 |
| Phosphorus (mg/dL) | 6.6 ± 0.3 | 6.6 ± 0.1 | 6.3 ± .2 | 6.7 ± 0.3 | 6.3 ± 0.3 | 6.6 ± 0.2 | 5.9 to 8.3 |
| Potassium (mEq/L) | 4.3 ± 0.1 | 4.1 ± 0.1 | 4.7 ± 0.5 | 4.3 ± 0.1 | 4.4 ± 0.3 | 4.3 ± 0.1 | 5.2-7.8 |

As shown in TABLE 27, serum creatine kinase activity did not differ significantly between groups. Serum calcium concentrations did not differ significantly by group, although these values were slightly higher than the reference range established for non-obese Sprague-Dawley rats. Serum potassium concentrations also did not differ significantly by group. Serum chloride differed significantly between groups, however, the values were all within the reference range (data not shown).

Target Organ Effects

A summary of microscopic findings is provided below in TABLE 28.

TABLE 28

Summary of Histopathology Findings

| Tissue/Finding | Group Average Score or Percent | | | | | | Group Incidence | | | | | |
|---|---|---|---|---|---|---|---|---|---|---|---|---|
| | 1 | 2 | 3 | 4 | 5 | 6 | 1 | 2 | 3 | 4 | 5 | 6 |
| LIVER | | | | | | | | | | | | |
| lipidosis, hepatocytes, macrovesicular | 1.0 | 0.8 | 1.2 | 0.8 | 1.6 | 0.4 | 10/10 | 8/10 | 10/10 | 6/10 | 10/10 | 4/10 |
| lipidosis, hepatocytes, microvesicular | 3.4 | 2.0 | 3.8 | 1.2 | 3.6 | 1.0 | 10/10 | 10/10 | 10/10 | 9/10 | 10/10 | 8/10 |
| KIDNEY | | | | | | | | | | | | |
| mesangial expansion | 2.7 | 1.5 | 1.6 | 0.9 | 1.6 | 1.5 | 10/10 | 10/10 | 10/10 | 9/10 | 10/10 | 10/10 |
| dilatation, tubules | 3.0 | 1.6 | 2.3 | 1.4 | 2.5 | 2.7 | 10/10 | 9/10 | 10/10 | 10/10 | 10/10 | 10/10 |
| degeneration/regeneration, tubules | 1.9 | 0.8 | 1.8 | 1.0 | 2.2 | 1.1 | 10/10 | 8/10 | 10/10 | 9/10 | 10/10 | 8/10 |
| dilatation, renal pelvis | 1.6 | 2.1 | 1.2 | 1.3 | 2.0 | 1.1 | 8/10 | 10/10 | 7/10 | 7/10 | 9/10 | 6/10 |
| mineralization, renal pelvis | 0.6 | 0.8 | 0.1 | 0.3 | 0.1 | 0.3 | 4/10 | 7/10 | 1/10 | 2/10 | 1/10 | 3/10 |
| inflammation, renal pelvis | 0.0 | 0.0 | 0.0 | 0.0 | 0.2 | 0.0 | 0/10 | 0/10 | 0/10 | 0/10 | 1/10 | 0/10 |
| PANCREAS | | | | | | | | | | | | |
| hypertrophy, islets | 3.8 | 4.1 | 4.4 | 3.3 | 4.1 | 3.8 | 10/10 | 10/10 | 10/10 | 10/10 | 10/10 | 10/10 |
| mononuclear cell infiltrate, islets | 1.0 | 1.0 | 1.3 | 1.3 | 1.3 | 1.0 | 10/10 | 10/10 | 10/10 | 10/10 | 10/10 | 10/10 |
| islet cell degeneration | 2.6 | 2.4 | 2.5 | 1.5 | 2.0 | 1.9 | 10/10 | 10/10 | 10/10 | 10/10 | 10/10 | 10/10 |
| fibrosis, islets | 2.5 | 2.4 | 2.9 | 1.7 | 2.1 | 2.1 | 10/10 | 10/10 | 10/10 | 10/10 | 10/10 | 10/10 |
| hemorrhage/hemoiderin, islets | 1.1 | 1.0 | 1.2 | 0.8 | 1.1 | 0.9 | 10/10 | 10/10 | 10/10 | 8/10 | 10/10 | 9/10 |
| percent of islet area containing positive insulin positive cells (%) | 52.3 | 57.4 | 53.0 | 68.7 | 46.8 | 78.5 | NA | NA | NA | NA | NA | NA |

Figure 39:
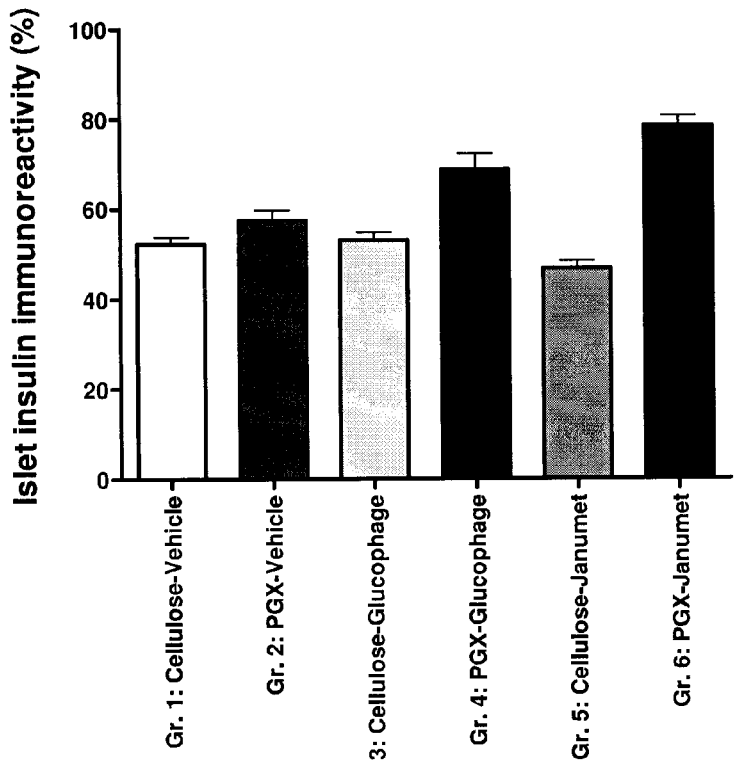
FIG. 39 graphically illustrates the beta cell mass, measured as islet insulin immunoreactivity (%) in the rats from Groups 1-6 at week seven (during necropsy) of the study, as described in EXAMPLE 8.

NA = Not applicable
Severity Scores: 0 = within normal limits; 1 = minimal; 2 = mild; 3 = moderate; 4 = marked; 5 = severe Pancreas A clear treatment-related difference was seen with the percent of islet area containing insulin-positive cells in the pancreas. Specifically, for vehicle, GLUCOPHAGE, or JANUMET with cellulose, the percentages were 52%, 53% and 47% respectively. PGX treatment resulted in higher percentages when combined with vehicle (57%), GLUCOPHAGE (69%), or JANUMET (79%), thereby demonstrating a synergistic effect on insulin production when combined with PGX. FIG. 39 graphically illustrates the beta cell mass, measured as islet insulin immunoreactivity (%) in the rats from Groups 1-6 at week seven (during necropsy) of the study. As shown in FIG. 39, pancreatic beta cell mass varied as a function of treatment (F(5,59)=28.53, p<0.0001). Rats fed PGX-containing diet tended to have greater insulin-immunoreactive area than rats fed cellulose-containing diet, and this difference was increased by administration of GLUCOPHAGE or JANUMET. In rats fed cellulose-containing diet, GLUCOPHAGE showed no clear effect and JANUMET tended to decrease insulin-immunoreactive area. All post hoc comparisons reached statistical significance except for the differences between Group 1 (Cellulose-vehicle) and Group 2 (PGX-vehicle); Group 3 (cellulose-GLUCOPHAGE) and Group 5 (cellulose-JANUMET), and the difference between Groups 2 and 3 and the difference between Groups 3 and 5.

Figure 40:
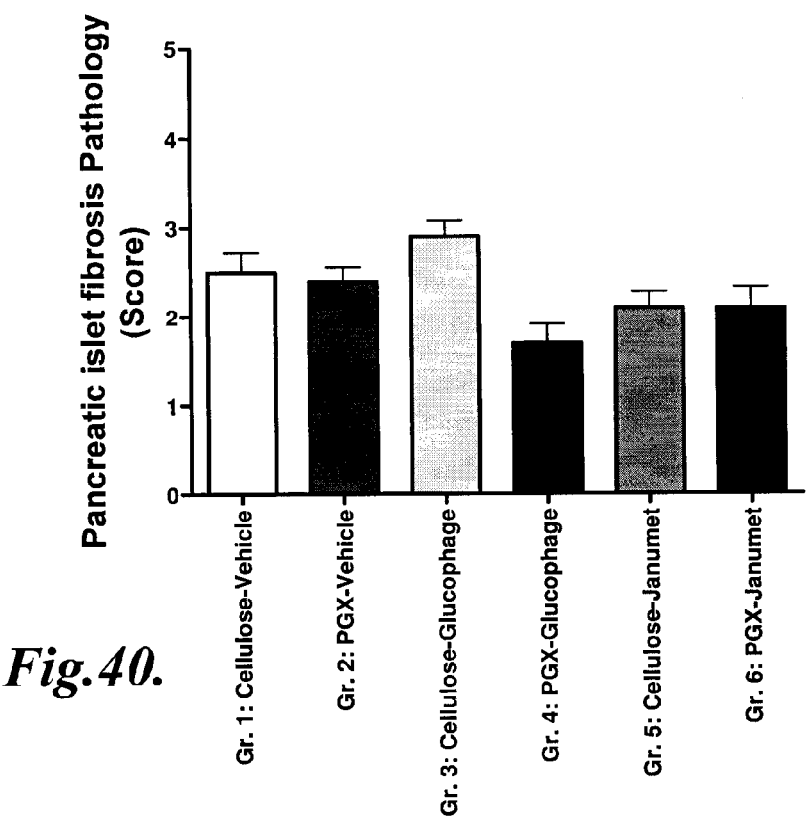
FIG. 40 graphically illustrates the pancreatic islet fibrosis scores on a scale of 0 (pathology absent) to 5 (severe pathology) using tissue sections stained with hematoxylin and eosin from rats in Groups 1-6 at week seven (during necropsy) of the study, as described in EXAMPLE 8.

FIG. 40 graphically illustrates the pancreatic islet fibrosis scores on a scale of 0 (pathology absent) to 5 (severe pathology) using tissue sections stained with hematoxylin and eosin from rats in Groups 1-6 at week seven (during necropsy) of the study. As shown in FIG. 40, pancreatic islet fibrosis was generally mild or moderate (2 or 3). Group scores differed significantly (K(6)=16.31, p<0.01; Kruskal-Wallis test). The amount of islet fibrosis was slightly lower for vehicle and cellulose as compared to GLUCOPHAGE and cellulose (2.5 and 2.9, respectively). There was a reduction with JANUMET and cellulose (2.1), as compared to either vehicle or GLUCOPHAGE with cellulose. However, the only significant difference observed in post hoc testing was the difference between Group 3 (cellulose-GLUCOPHAGE) and Group 4 (PGX-GLUCOPHAGE, p<0.01).

Figure 41:
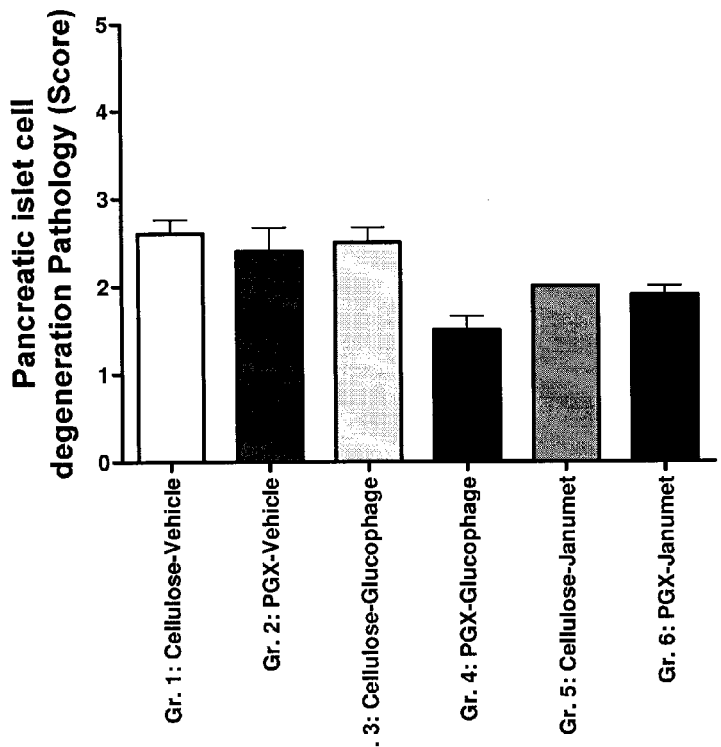
FIG. 41 graphically illustrates the pancreatic islet cell degeneration scores on a scale of 0 (pathology absent) to 5 (severe pathology) in rats in Groups 1-6 at week seven (during necropsy) of the study, as described in EXAMPLE 8.

FIG. 41 graphically illustrates the pancreatic islet cell degeneration scores on a scale of 0 (pathology absent) to 5 (severe pathology) in rats in Groups 1-6 at week seven (during necropsy) of the study. As shown in FIG. 41, scores for pancreatic islet cell degeneration tended to parallel the results seen for beta cell mass (compare FIG. 41 and FIG. 39). Pancreatic islet cell degeneration, including vacuolation and apoptosis, was reduced by treatment with JANUMET and Cellulose (2.0) as compared to Vehicle and Cellulose (2.6). When PGX was used instead of cellulose, there was a very minor decrease with vehicle (2.4), and a greater decrease when combined with GLUCOPHAGE (1.5) as compared to the comparable cellulose treatment. PGX and JANUMET had no greater reduction in the islet cell degeneration as compared with cellulose and JANUMET. Scores differed significantly between groups (K(6)=22.74, p<0.005). However, the only differences that reached statistical significance in post hoc testing were the differences between Group 4 and Groups 1 (p<0.01), 2 (p<0.05), and 3 (p<0.01).

As shown in TABLE 28, pancreatic islet hypertrophy was present in all animals regardless of treatment and was generally moderate (3) or marked (4). Pathology scores did not differ significantly between groups. As further shown in TABLE 28, pancreatic mononuclear cell infiltrates, and pancreatic hemorrhage and hemosiderin were generally scored as minimal and did not differ between groups.

Kidney

In the kidney, there were a variety of changes typical of those seen in the Zucker rat diabetes model. With vehicle and GLUCOPHAGE, PGX led to reduced severity of mesangial matrix expansion in the kidney, as compared to cellulose. With JANUMET, there was a reduction of the severity of the mesangial change with both PGX and cellulose to levels comparable with vehicle and PGX combined. PGX with vehicle resulted in a reduction in both the tubular dilatation and tubular degeneration/regeneration in the kidney. GLUCOPHAGE combined with PGX also resulted in a lower score for tubular dilatation, and tubular degeneration/regeneration. However, only the score for tubular degeneration/regeneration was lower for JANUMET with PGX versus JANUMET with cellulose.

Figure 42:
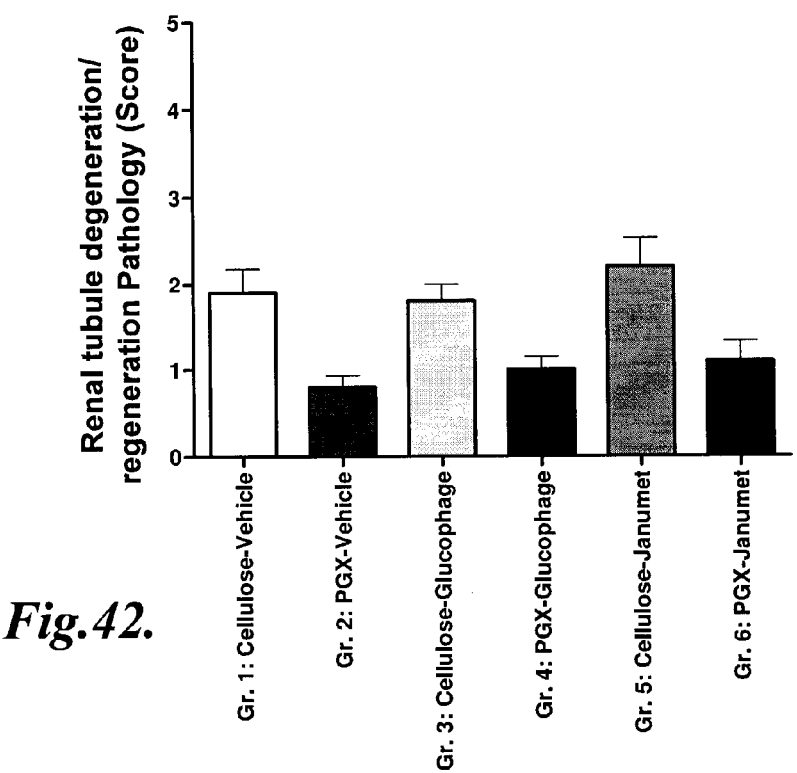
FIG. 42 graphically illustrates the renal tubule degeneration/regeneration pathology scores on a scale of 0 (pathology absent) to 5 (severe pathology) using tissue sections from rats in Groups 1-6 at week seven (during necropsy) of the study, as described in EXAMPLE 8.

FIG. 42 graphically illustrates the renal tubule degeneration/regeneration pathology scores on a scale of 0 (pathology absent) to 5 (severe pathology) using tissue sections from rats in Groups 1-6 at week seven (during necropsy) of the study. As shown in FIG. 42, renal tubule degeneration/regeneration scores generally varied from minimal to mild. Group scores varied with treatment (K(6)=21.89, p<0.0001). Generally, PGX-containing diet reduced pathology relative to cellulose-containing diet. However, the only differences that reached statistical significance on post hoc testing were Group 1 (cellulose-vehicle, p<0.05) vs. 2 (PGX-vehicle, p<0.05), Group 2 vs. Group 3 (cellulose-GLUCOPHAGE) and Group 2 vs. Group 5 (cellulose-JANUVIA, p<0.01).

Figure 43:
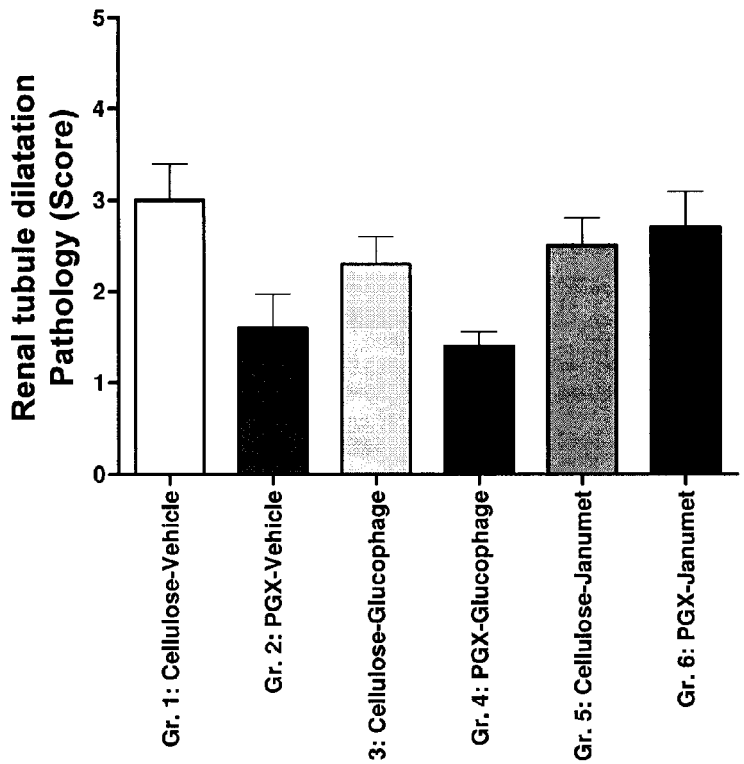
FIG. 43 graphically illustrates the renal tubule dilatation pathology scores on a scale of 0 (pathology absent) to 5 (severe pathology) using tissue sections from rats in Groups 1-6 at week seven (during necropsy) of the study, as described in EXAMPLE 8.

FIG. 43 graphically illustrates the renal tubule dilatation pathology scores on a scale of 0 (pathology absent) to 5 (severe pathology) using tissue sections from rats in Groups 1-6 at week seven (during necropsy) of the study. As shown in FIG. 43, pathology scores ranged from minimal to moderate. Group scores varied significantly (K(6)=14.04, p<0.05); however, the only statistically significant difference in post hoc testing was the difference between Groups 1 and 4 (PGX-GLUCOPHAGE, p<0.05).

Figure 44:
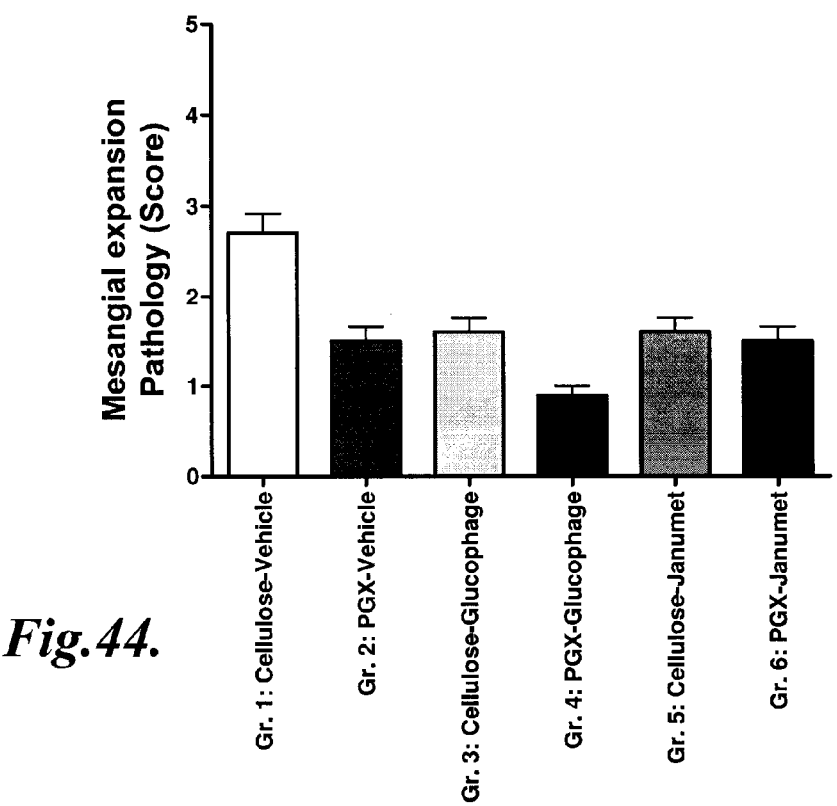
FIG. 44 graphically illustrates the mesangial expansion pathology scores on a scale of 0 (pathology absent) to 5 (severe pathology) using tissue sections from rats in Groups 1-6 at week seven (during necropsy) of the study, as described in EXAMPLE 8.

FIG. 44 graphically illustrates the mesangial expansion pathology scores on a scale of 0 (pathology absent) to 5 (severe pathology) using tissue sections from rats in Groups 1-6 at week seven (during necropsy) of the study. As shown in FIG. 44, mesangial expansion scores were mostly minimal, however, scores for Group 1 were mostly mild to moderate. Group scores differed significantly (K(6)=28.56, p<0.0001). On post hoc testing, Group 1 was significantly higher than Group 2 (p<0.05), Group 4 (p<0.001) and Group 6 (PGX-JANUVIA, p<0.01). In the vehicle treated animals, PGX led to reduced severity of this glomerular change as compared to cellulose (1.5 vs. 2.7, respectively). Similarly, in animals treated with GLUCOPHAGE, PGX treated resulted in a reduction in severity (0.9 vs. 1.6, for PGX and cellulose, respectively). With JANUMET, there was a reduction of the severity of the mesangial change with both PGX (1.5) and cellulose (1.6) to levels comparable with vehicle and PGX combined (1.5).

Figure 45:
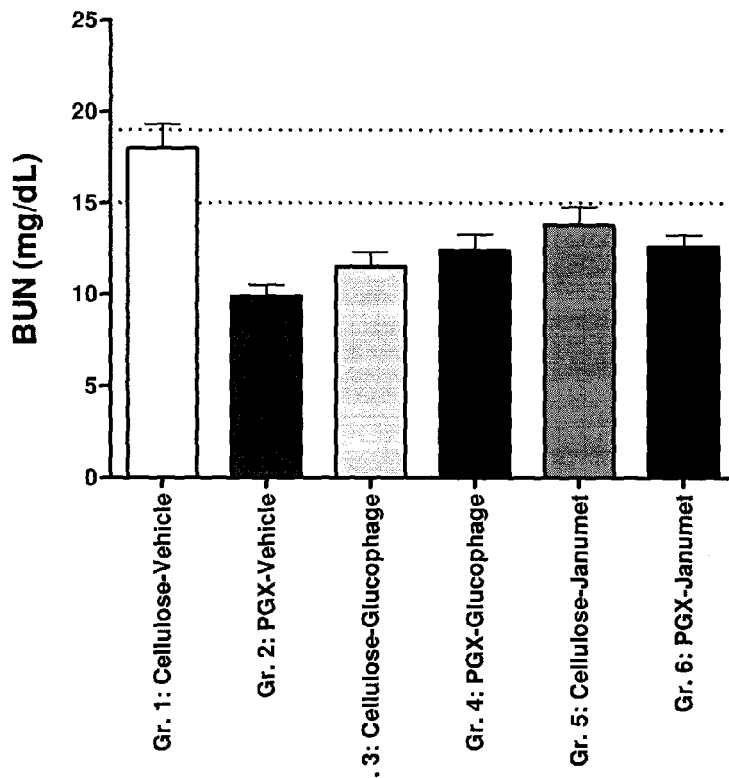
FIG. 45 graphically illustrates the blood urea nitrogen (BUN) levels (mg/dL) measured from a terminal blood sample obtained from rats in Groups 1-6 at week seven of the study, as described in EXAMPLE 8.

FIG. 45 graphically illustrates the blood urea nitrogen (BUN) levels (mg/dL) measured from a terminal blood sample obtained from rats in Groups 1-6 at week seven of the study. As shown in FIG. 45, blood urea nitrogen was generally below a reference range established for non-obese Sprague-Dawley rats (reference range is shown as the area between the dotted lines in FIG. 45). However, groups differed significantly (F(5,59)=9.13, p<0.0001). The pattern of results was similar to that seen for mesangial expansion (compare FIGS. 44 and 45). Group 1 was significantly higher than all other groups (p<0.01 to p<0.0001); no other comparison reached statistical significance except for Group 2 vs. Group 5 (p<0.05).

As shown in TABLE 28, renal pelvis dilatation was generally scored as minimal or mild, and scores did not differ significantly between groups. As further shown in TABLE 28, renal pelvis mineralization was generally scored as absent or minimal. Scores differed sufficiently to produce a significant main effect (K(6)=11.89, p<0.05). However, no post hoc comparison reached statistical significance (all p>0.05). As further shown in TABLE 28, renal pelvis inflammation was generally scored as absent, and scores did not differ significantly between groups.

Liver

Figure 46:
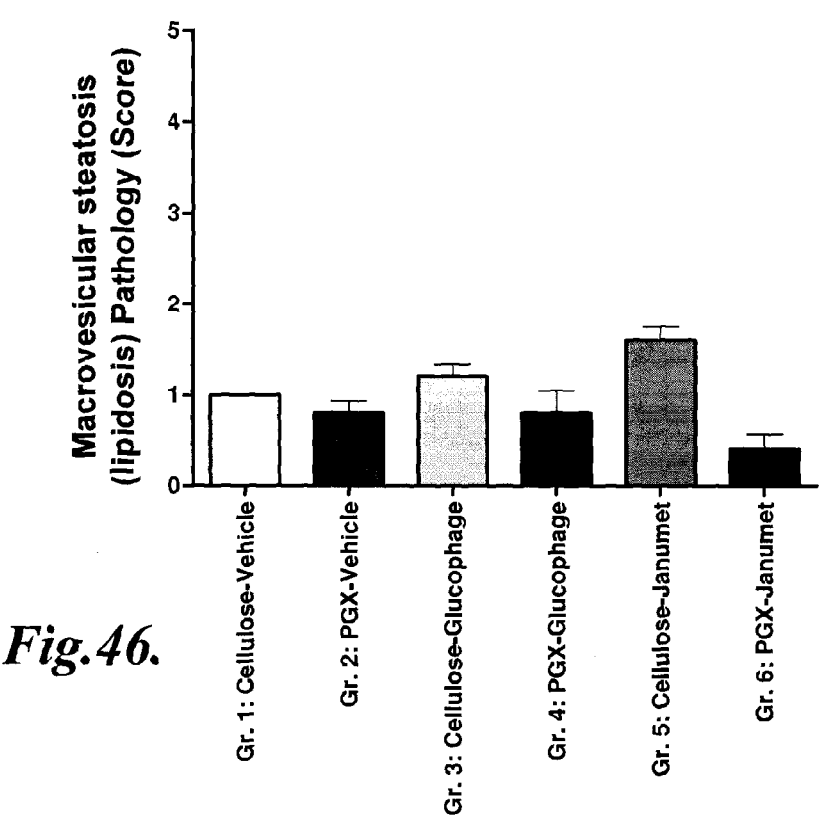
FIG. 46 graphically illustrates the macrovesicular steatosis (lipidosis) on a scale of 0 (pathology absent) to 5 (severe pathology) using liver tissue sections from rats in Groups 1-6 at week seven (necropsy) of the study, as described in EXAMPLE 8.

Overview: In the liver, all treatment groups displayed microvesicular and macrovesicular hepatocyte vacuoles. These vacuoles were Sudan Black positive, consistent with the presence of lipid (macrovesicular and microvesicular hepatic lipidosis). The severity and incidence of the microvesicular lipidosis was greater than that of macrovesicular lipidosis. GLUCOPHAGE and cellulose, or JANUMET and cellulose did not result in any improvement in the lipidosis scores as compared to the vehicle and cellulose treatment (3.4, 3.8, and 3.6, respectively). However, when PGX was used in combination with either vehicle, GLUCOPHAGE, or JANUMET, there was a notable reduction in the microvesicular lipidosis score (2.0, 1.2, and 1.0, respectively). Macrovesicular hepatocyte vacuolation was minimal to occasionally mild, and while present in all treatment groups, was not observed in all animals. The incidence was lower for the PGX treated groups versus the corresponding cellulose treated groups, and the lowest incidence and severity was seen in Group 6 (4 of 10 animals, with an average score of 0.4). FIG. 46 graphically illustrates the macrovesicular steatosis (lipidosis) on a scale of 0 (pathology absent) to 5 (severe pathology) using liver tissue sections from rats in Groups 1-6 at week seven (necropsy) of the study. As shown in FIG. 46, macrovesicular steatosis was generally scored as minimal. While groups differed significantly (K(6)=22.41, p<0.0005), the only post hoc comparisons that reached statistical significance were the differences between Group 6 (PGX-JANUMET) and Groups 3 (Cellulose-GLUCOPHAGE, p<0.05) and 5 (cellulose-JANUMET, p<0.001), with Group 6 lower than all other groups.

Figure 47:
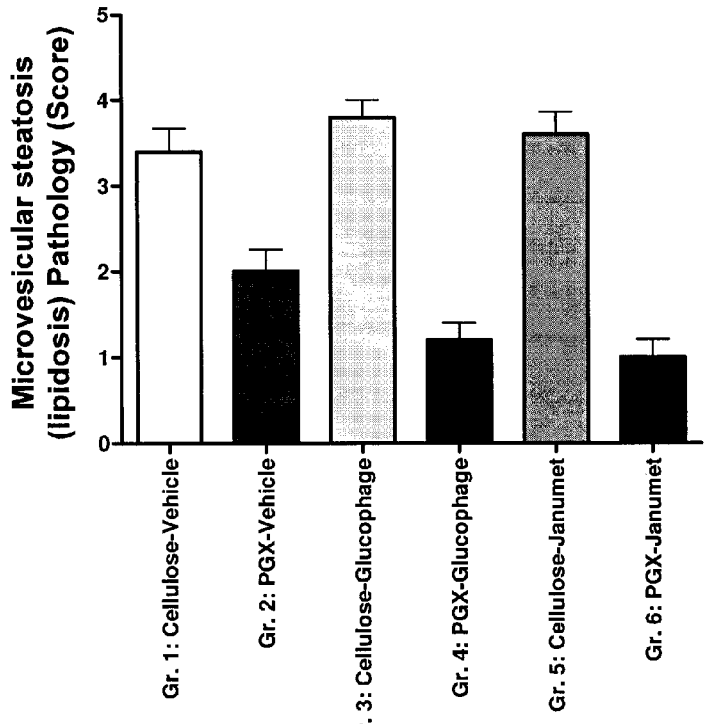
FIG. 47 graphically illustrates the microvesicular steatosis (lipidosis) pathology scores on a scale of 0 (pathology absent) to 5 (severe pathology) using tissue sections from rats in Groups 1-6 at week seven (during necropsy) of the study, as described in EXAMPLE 8.

FIG. 47 graphically illustrates the microvesicular steatosis (lipidosis) pathology scores on a scale of 0 (pathology absent) to 5 (severe pathology) using tissue sections from rats in Groups 1-6 at week seven (during necropsy) of the study. As shown in FIG. 47, microvesicular steatosis scores covered a wide range. Groups fed PGX-containing diet tended to have lower steatosis scores; the combination of PGX with either GLUCOPHAGE or JANUMET increased this effect. The main effect of treatment was statistically significant (K(6)=43.01, p<0.0001). While the differences between Groups 1 (cellulose-vehicle) and 2 (PGX-vehicle) did not reach statistical significance (p>0.05), the difference between Groups 3 and 4 (PGX-GLUCOPHAGE, p<0.001) and between Groups 5 (cellulose-JANUMET) and 6 (p<0.001) were significant.

Figure 48:
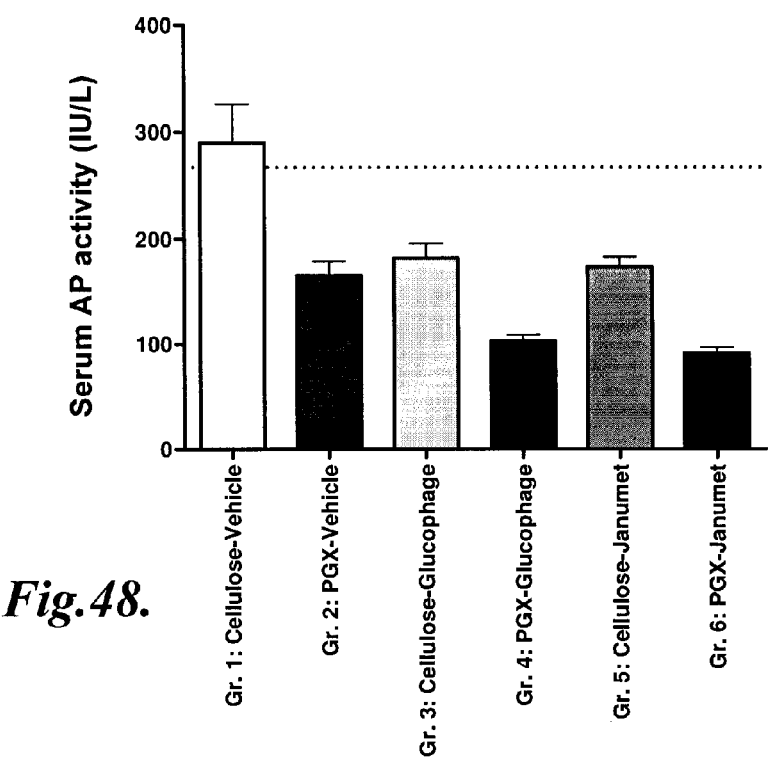
FIG. 48 graphically illustrates the alkaline phosphatase activity (IU/L) measured in a terminal blood sample obtained from rats in Groups 1-6 at week seven of the study, as described in EXAMPLE 8.

FIG. 48 graphically illustrates the alkaline phosphatase activity (IU/L) measured in a terminal blood sample obtained from rats in Groups 1-6 at week seven of the study. As shown in FIG. 48, serum alkaline phosphatase activity was generally within a reference range for non-obese Sprague-Dawley rats (region shown under the dotted line in FIG. 48); the exception was the double control group (Group 1). Relative to Group 1, PGX-containing diet, GLUCOPHAGE and JANUMET each reduced serum alkaline phosphatase activity; combination of PGX-containing diet with GLUCOPHAGE or JANUMET produced a greater reduction. The main effect of treatment was statistically significant (F(5,59)=16.53, p<0.0001). All post hoc comparisons reached statistical significance except for comparisons between single treatments (Group 2 vs. Group 3 or 5; Group 3 vs. 5) and between combination treatments (Group 4 vs. 6).

Figure 49:
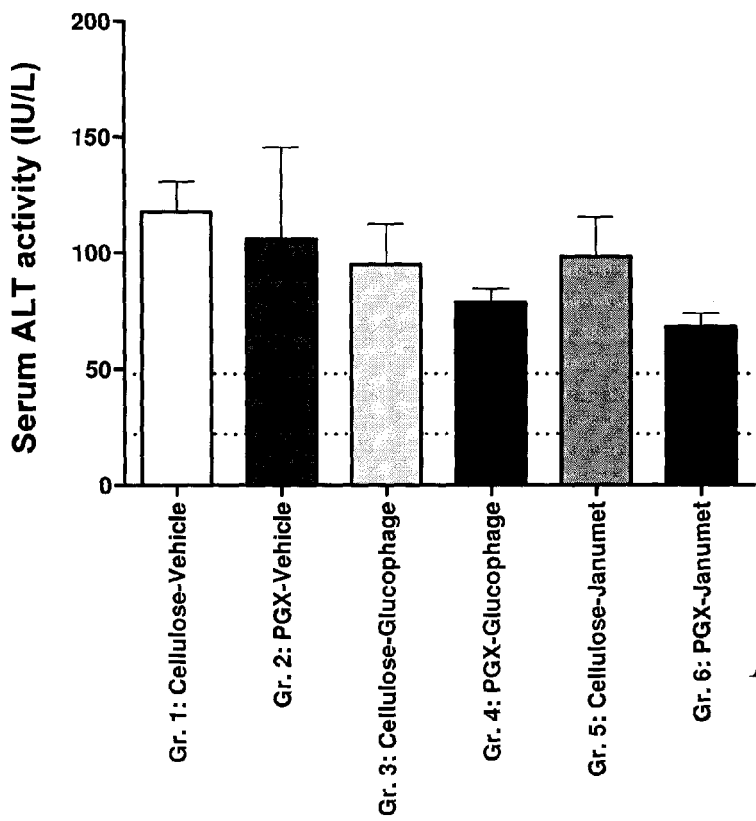
FIG. 49 graphically illustrates the serum alanine aminotransferase activity (ALT/SGPT) (IU/L) measured in a terminal blood sample obtained from rats in Groups 1-6 at week seven of the study, as described in EXAMPLE 8.

FIG. 49 graphically illustrates the serum alanine aminotransferase activity (also known as serum glutamic-pyruvic transaminase) (ALT/SGPT) (IU/L) measured in a terminal blood sample obtained from rats in Groups 1-6 at week seven of the study. As shown in FIG. 49, serum alanine aminotransferase activity was generally high, exceeding the reference range (shown as the region between the dotted lines in FIG. 49). The main effect of treatment did not reach statistical significance.

Figure 50:
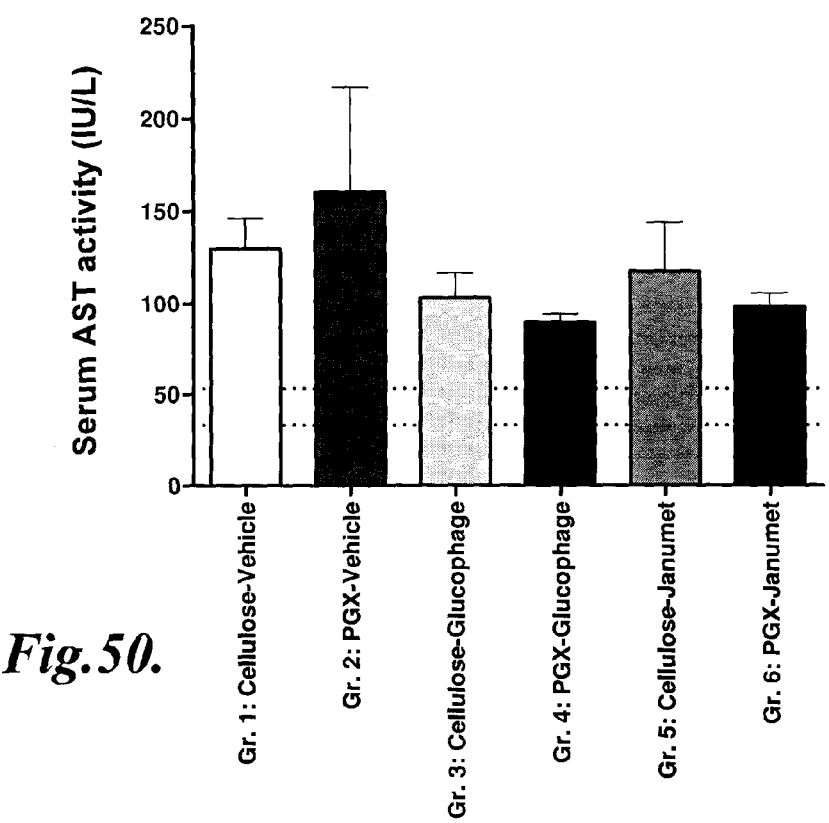
FIG. 50 graphically illustrates the level of serum aspartate aminotransferase activity (AST/SGOT) (IU/L) measured in a terminal blood sample obtained from rats in Groups 1-6 at week seven of the study, as described in EXAMPLE 8.

FIG. 50 graphically illustrates the level of serum aspartate aminotransferase (also known as serum glutamic oxaloacetic transaminase) activity (AST/SGOT) (IU/L) measured in a terminal blood sample obtained from rats in Groups 1-6 at week seven of the study. As shown in FIG. 50, serum aminotransferase activity was generally high, exceeding the reference range (shown as the region between the dotted lines in FIG. 50). The main effect of treatment did not reach statistical significance.

Figure 51:
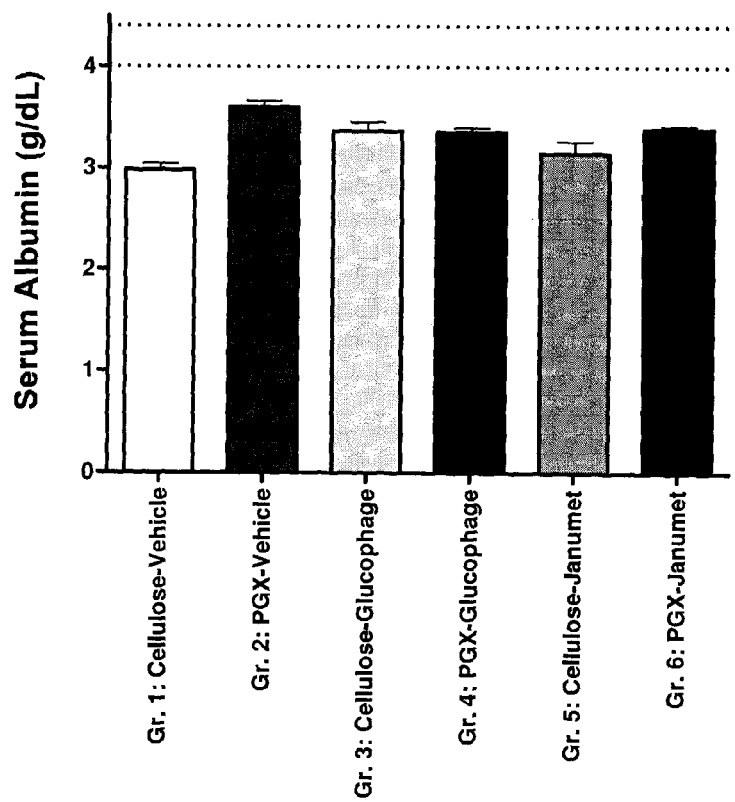
FIG. 51 graphically illustrates the albumin concentration (g/dL) measured in a terminal blood sample obtained from rats in Groups 1-6 at week seven of the study, as described in EXAMPLE 8.

FIG. 51 graphically illustrates the albumin concentration (g/dL) measured in a terminal blood sample obtained from rats in Groups 1-6 at week seven of the study. As shown in FIG. 51, circulating albumin concentrations were generally below the reference range (shown as the region between the dotted lines in FIG. 51), consistent with observations in other unrelated studies of rats with and without metabolic disease. Groups differed significantly ($F(5,59)=9.06$, $p<0.0001$). Group 1 showed significantly lower albumin concentrations than all other groups except Group 5 ($p<0.01$ to $p<0.001$). Group 2 showed significantly higher albumin concentrations than Group 5 ($p<0.001$); no other post hoc comparison reached statistical significance.

Figure 52:
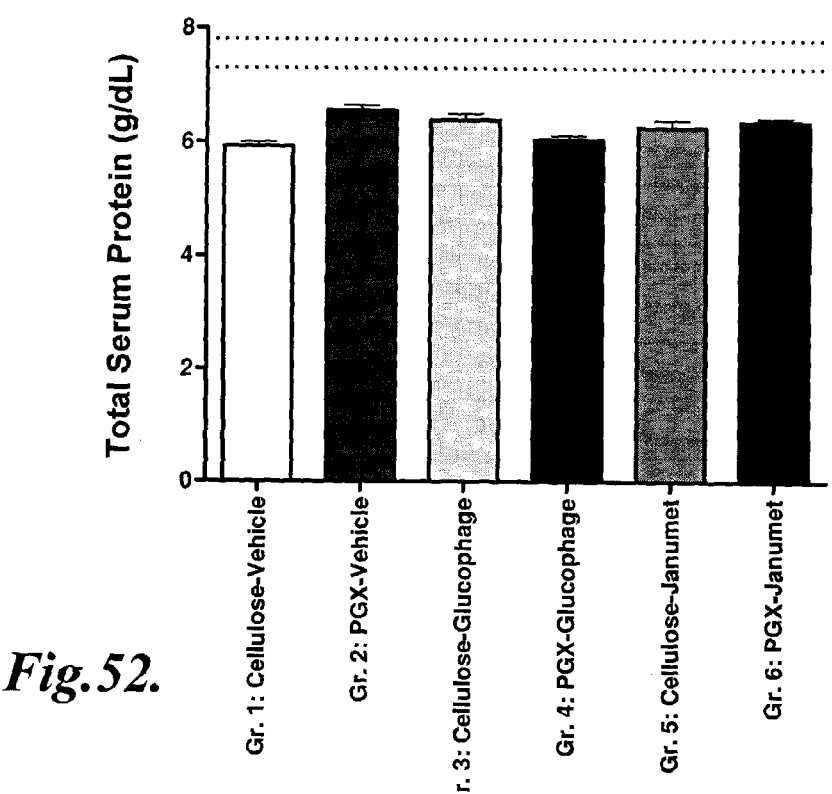
FIG. 52 graphically illustrates the total circulating protein concentration (g/dL) measured in a terminal blood sample obtained from rats in Groups 1-6 at week seven of the study, as described in EXAMPLE 8.

FIG. 52 graphically illustrates the total circulating protein concentration (g/dL) measured in a terminal blood sample obtained from rats in Groups 1-6 at week seven of the study. As shown in FIG. 52, the total circulating protein concentrations showed a pattern of effects very similar to albumin (compare FIGS. 51 and 52). The main effect of treatment was statistically significant ($F(5,59)=6.43$, $p<0.0001$). Group 1 showed significantly lower albumin concentrations than all other groups except Group 5 ($p<0.05$ to $p<0.001$). Group 2 showed significantly higher albumin concentrations than Group 5 ($p<0.01$); no other post hoc comparison reached statistical significance.

Figure 53:
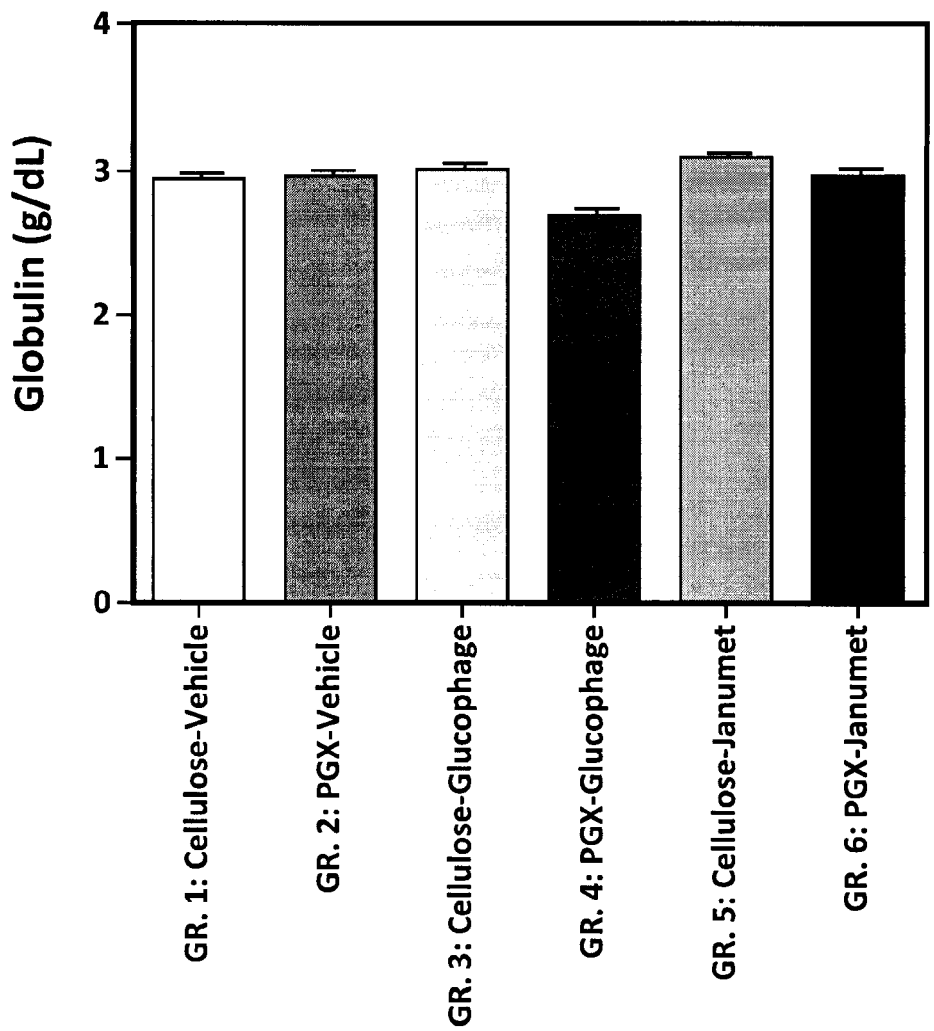
FIG. 53 graphically illustrates the circulating globulin concentrations (g/dL) measured in a terminal blood sample obtained from rats in Groups 1-6 at week seven of the study, as described in EXAMPLE 8.

FIG. 53 graphically illustrates the circulating globulin concentrations (g/dL) measured in a terminal blood sample obtained from rats in Groups 1-6 at week seven of the study. The results shown in FIG. 53 are very similar to the total circulating protein (compare FIGS. 52 and 53). However, values observed for Group 4 were lower than those for any other group. This resulted in a main effect ($F(5,59)=11.05$, $p<0.0001$) and significant post hoc comparisons with all other groups (all $p<0.001$). No other differences reached statistical significance.

It was also determined that total bilirubin concentrations were generally low, with each group including observations below the detection limit (data not shown). Despite the low concentrations, a significant main effect was observed ($F(5, 59)=5.84$, $p<0.0005$). Post hoc comparisons with Group 2 or Group 6 reached statistical significance ($p<0.05$ to $p<0.01$); no other comparison was significant.

SUMMARY OF RESULTS

TABLE 29

Summary of Significant Findings

| Parameters Measured | PGX only | GLUCOPHAGE only | Combination of PGX and GLUCOPHAGE | JANUMET only | Combination of PGX and JANUMET | General Comments regarding parameter |
|---|---|---|---|---|---|---|
| Body weight at end of study | trend towards decrease | increased | no effect | no effect | decrease when combined with PGX | increased in Zucker rats |
| Fat mass by DEXA | no effect | slight increase | no effect | no effect | decrease when combined with PGX | increased in Zucker rats |
| Food consumption (all weeks) | decreased | decreased | significant decrease, much greater when combined with PGX | decreased | significant decrease; decrease greater when combined with PGX | increased in Zucker Rats |
| Non-fasted blood glucose (week 6) | decreased | decreased | significant decrease, much greater decrease when combined with PGX | decreased | significant decreas, much greater decrease when combined with PGX | increased in Zucker rats |
| 16 hour Fasted blood glucose (week 6) | decreased | decreased | significant decrease, much greater decrease when combined with PGX | decreased | significant decrease, much greater decrease when combined with PGX | increased in older or fat-fed Zucker rats |
| Hemoglobin glycosylation (week 6) | decreased | decreased | significant decrease, much greater decrease when combined with PGX | decreased | significant decrease, much greater decrease when combined with PGX | increased with hyperglycemia |
| Composite insulin sensitivity index from OGTT (week 6): integrated measure of insulin release and insulin sensitivity | no effect | no effect | increase when combined with PGX | no effect | increase when combined with PGX | increase represents more normal function |

TABLE 29-continued

Summary of Significant Findings

| Parameters Measured | PGX only | GLUCOPHAGE only | Combination of PGX and GLUCOPHAGE | JANUMET only | Combination of PGX and JANUMET | General Comments regarding parameter |
|---|---|---|---|---|---|---|
| total cholesterol (week 7) | decreased | increased | decrease when combined with PGX | increased | decrease when combined with PGX | increased with dyslipidemia due to disease model and high fat diet |
| pancreatic beta cell mass (terminal) | trend toward increase | no effect | increased when combined with PGX | no effect | increase when combined with PGX | decreased with chronic diabetes |
| pancreatic islet cell degeneration | no effect | no effect | decrease when combined with PGX | slight decrease | slight decrease when combined with PGX | increased with chronic metabolic disease (e.g. diabetes) |
| renal tubule degeneration/regeneration (terminal) | decrease | no effect | decrease when combined with PGX | no effect | decrease when combined with PGX | increased with diabetes/nephropathy |
| Mesangial expansion | decrease | decrease | decrease when combined with PGX | decrease | decrease when combined with PGX | increases with nephropathy |
| blood urea nitrogen | decrease | decrease | decrease when combined with PGX | decrease | decrease when combined with PGX | increase with nephropathy, protein intake; decreases with hepatic dysfunction |
| Hepatic microvesicular vacuolation | decrease | no effect | decrease when combined with PGX | no effect | decrease when combined with PGX | increased with hepatic damage |
| Serum alkaline phosphatase | decrease | decrease | greater decrease when combined with PGX | decrease | greater decrease when combined with PGX | increased with hepatobiliary disease |
| Serum albumin | increase | increase | increase when combined with PGX | slight increase | increase when combined with PGX | decreased with loss of hepatic function |
| total serum protein | increase | increase | slight increase when combined with PGX | increase | increase when combined with PGX | decreased with loss of hepatic function |

While various embodiments of the invention has been illustrated and described, it will be appreciated that changes can be made therein without departing from the spirit and scope of the invention.

The embodiments of the invention in which an exclusive property or privilege is claimed are defined as follows:

1. A pharmaceutical composition comprising (i) a dietary fiber composition comprising from about 48% to about 90% (w/w) glucomannan, from about 5% to about 20% (w/w) xanthan gum, and from about 5% to about 30% (w/w) alginate; and (ii) at least one of metformin or sitagliptin or a combination thereof, wherein the pharmaceutical composition is effective to lower elevated blood glucose levels and total blood cholesterol levels in a subject significantly more than the dietary fiber composition alone or a composition consisting of at least one of metformin or sitagliptin or a combination thereof.

2. The pharmaceutical composition of claim 1, wherein the pharmaceutical composition comprises the dietary fiber composition and metformin.

3. The pharmaceutical composition of claim 1, wherein the pharmaceutical composition comprises the dietary fiber composition and sitagliptin.

4. The pharmaceutical composition of claim 1, wherein the pharmaceutical composition comprises the dietary fiber composition, metformin, and sitagliptin.

5. The pharmaceutical composition of claim 1, wherein the dietary fiber composition comprises from about 50% to about 80% (w/w) glucomannan, from about 10% to about 20% (w/w) xanthan gum, and from about 10% to about 20% (w/w) alginate.

6. The pharmaceutical composition of claim 1, wherein the dietary fiber composition is granulated.

7. The pharmaceutical composition of claim 1, wherein the dietary fiber composition further comprises at least one lipid or blend thereof, wherein the lipid or blend thereof comprises at least 20% (w/w) of the total dietary fiber composition.

8. The pharmaceutical composition of claim 1, wherein the pharmaceutical composition is contained in a capsule, compounded into a tablet, formulated into a powder, or a combination thereof.

9. A method for treating or ameliorating one or more symptoms associated with a metabolic disease or disorder, the method comprising co-administering to a subject in need thereof:

(i) a dietary fiber composition comprising from about 48% to about 90% (w/w) glucomannan, from about 5% to about 20% (w/w) xanthan gum, and from about 5% to about 30% (w/w) alginate; and (ii) an effective amount of at least one of metformin or sitagliptin or a combination thereof, wherein the method is effective to lower elevated blood glucose levels and total blood cholesterol levels in a subject significantly more than the dietary fiber composition alone or a composition consisting of at least one of metformin or sitagliptin or a combination thereof.

10. The method of claim 9, wherein the metabolic disease or disorder is metabolic syndrome or type II diabetes.

11. A combination of:
(i) a dietary fiber composition comprising from about 48% to about 90% (w/w) glucomannan, from about 5% to about 20% (w/w) xanthan gum, and from about 5% to about 30% (w/w) alginate; and
(ii) an effective amount of at least one of metformin and/or sitagliptin;

wherein the combination is for use in treating or ameliorating one or more symptoms associated with a metabolic disease or disorder in a subject and (i) and (ii) are for co-administration to the subject, and wherein the combination is effective to lower elevated blood glucose levels and total blood cholesterol levels in a subject significantly more than the dietary fiber composition alone or a composition consisting of at least one of metformin or sitagliptin or a combination thereof.

12. The combination of claim 11, wherein the metabolic disease or disorder is metabolic syndrome.

13. The pharmaceutical composition of claim 1, wherein a first unit dose comprises the dietary fiber composition and a second unit dose comprises at least one of metformin or sitagliptin or a combination thereof.

14. The pharmaceutical composition of claim 13, wherein the first unit dose is formulated into a powder and the second unit dose is contained in a capsule or compounded in a tablet.

15. The pharmaceutical composition of claim 6, wherein the dietary fiber composition further comprises at least one lipid or blend thereof, wherein the lipid or blend thereof comprises at least 20% (w/w) of the total dietary fiber composition.

16. The method of claim 9, wherein the dietary fiber composition comprises from about 50% to about 80% (w/w) glucomannan, from about 10% to about 20% (w/w) xanthan gum, and from about 10% to about 20% (w/w) alginate.

17. The method of claim 9, wherein the dietary fiber composition is granulated.

18. The method of claim 9, wherein the dietary fiber composition is administered to the subject in an amount of from about 1 g to about 50 g per day.

19. The method of claim 9, wherein the method comprises administering the dietary fiber composition at least once a day for a time period of at least two weeks.

20. The method of claim 9, wherein the method comprises co-administering the dietary fiber composition and metformin, and wherein the metformin is administered in an amount from about 50 mg to about 2000 mg per day for a time period of at least two weeks.

21. The method of claim 20, wherein the metformin is administered in an amount of about 1000 mg per day for a time period of at least two weeks.

22. The method of claim 9, wherein the method comprises co-administering the dietary fiber composition and metformin, and wherein the dietary fiber composition is administered to the subject (a) before the administration of metformin; (b) simultaneously with the administration of metformin; or (c) after the administration of metformin.

23. The method of claim 9, wherein the method comprises co-administering the dietary fiber composition and sitagliptin, and wherein the sitagliptin is administered in an amount of from about 5 mg to about 100 mg per day for a time period of at least two weeks.

24. The method of claim 9, wherein the method comprises co-administering the dietary fiber composition and sitagliptin, and wherein the dietary fiber composition is administered to the subject (a) before the administration of sitagliptin; (b) simultaneously with the administration of sitagliptin; or (c) after the administration of sitagliptin.

25. The method of claim 9, wherein the method comprises co-administering the dietary fiber composition, metformin and sitagliptin, and wherein the metformin and sitagliptin are co-administered in a single pharmaceutical composition and the dietary fiber composition is administered separately.

26. The method of claim 25, wherein the method comprises administering metformin in an amount of about 1000 mg per day for a time period of at least two weeks.

27. The method of claim 9, wherein the method comprises preserving pancreatic islet function by preserving islet cell mass and/or reducing pancreatic cell damage in the subject by administering the dietary fiber composition and metformin, sitagliptin, or a combination thereof.

28. The method of claim 9, wherein the method comprises increasing lean body mass in the subject by administering the dietary fiber composition and sitagliptin.

29. The method of claim 9, wherein the method comprises preserving liver function and/or reducing liver damage in the subject by administering the dietary fiber composition and sitagliptin.

30. The method of claim 9, wherein the method comprises preserving renal function and/or reducing kidney damage in the subject by administering the dietary fiber composition and sitagliptin.

31. The pharmaceutical composition of claim 1 for use in treating or ameliorating one or more symptoms associated with a metabolic disease or disorder in a subject.

32. The pharmaceutical composition of claim 31, wherein the metabolic disease or disorder is metabolic syndrome or type II diabetes.

33. The pharmaceutical composition of claim 1 for administration to the subject to provide an amount of the dietary fiber composition of from about 1 g to about 50 g per day.

34. The pharmaceutical composition of claim 1 for administration to the subject at least once a day for a time period of at least two weeks.

35. The pharmaceutical composition of claim 1 comprising metformin, for administration to the subject to provide from about 50 mg to about 2000 mg of the metformin per day for a time period of at least two weeks.

36. The pharmaceutical composition of claim 35 for administration to the subject to provide about 1000 mg of the metformin per day for a time period of at least two weeks.

37. The pharmaceutical composition of claim 1 comprising sitagliptin, for administration to the subject to provide from about 5 mg to about 100 mg of the sitagliptin per day for a time period of at least two weeks.

38. The pharmaceutical composition of claim 1 comprising metformin and sitagliptin, wherein the metformin and sitagliptin are for administration in a single pharmaceutical composition and the dietary fiber composition is for administration separately.

39. The combination of claim 11, wherein the dietary fiber composition comprises from about 50% to about 80% (w/w) glucomannan, from about 10% to about 20% (w/w) xanthan gum, and from about 10% to about 20% (w/w) alginate.

40. The combination of claim 11, wherein the dietary fiber composition is granulated.

41. The combination of claim 11, wherein the dietary fiber composition is for administration to the subject in an amount of from about 1 g to about 50 g per day.

42. The combination of claim 11, wherein the dietary fiber composition is for administration at least once a day for a time period of at least two weeks.

43. The combination of claim 11 comprising metformin, wherein the metformin is for administration in an amount of about 50 mg to about 2000 mg per day for a time period of at least two weeks.

44. The combination of claim 43, wherein the metformin is for administration in an amount of about 1000 mg per day for a time period of at least two weeks.

45. The combination of claim 11 comprising metformin, wherein the dietary fiber composition is for administration to the subject (a) before administration of the metformin; (b) simultaneously with administration of the metformin; or (c) after administration of the metformin.

46. The combination of claim 11 comprising sitagliptin, wherein the sitagliptin is for administration in an amount of from about 5 mg to about 100 mg per day for a time period of at least two weeks.

47. The combination of claim 11 comprising sitagliptin, wherein the dietary fiber composition is for administration to the subject (a) before administration of the sitagliptin; simultaneously with administration of the sitagliptin; or (c) after administration of the sitagliptin.

48. The combination of claim 11 comprising metformin and sitagliptin, wherein the metformin and sitagliptin are for administration in a single pharmaceutical composition and the dietary fiber composition is for administration separately.

* * * * *

UNITED STATES PATENT AND TRADEMARK OFFICE
CERTIFICATE OF CORRECTION

PATENT NO. : 9,669,051 B2  
APPLICATION NO. : 14/394337  
DATED : June 6, 2017  
INVENTOR(S) : R. J. Gahler et al.

Page 1 of 1

It is certified that error appears in the above-identified patent and that said Letters Patent is hereby corrected as shown below:

| Column | Line | Error |
|---|---|---|
| Drawing Sheets | Fig. 1 | "VICOSITY" should read --VISCOSITY-- |
| Drawing Sheets | Fig. 2 | "VICOSITY" should read --VISCOSITY-- |
| Drawing Sheets | Fig. 3 | "VICOSITY" should read --VISCOSITY-- |
| 29 | 14 | "Data was" should read --data were-- |
| 46 | 58 | "Data was" should read --data were-- |
| 57-58 | Table 29, Line 18 | "decreas, much" should read --decrease, much-- |

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*